US008431158B2

(12) United States Patent
Shoseyov et al.

(10) Patent No.: US 8,431,158 B2
(45) Date of Patent: Apr. 30, 2013

(54) COMPOSITIONS COMPRISING FIBROUS POLYPEPTIDES AND POLYSACCHARIDES

(75) Inventors: Oded Shoseyov, Karmei Yosef (IL); Shaul Lapidot, Kibbutz Tzora Doar-Na Shimshon (IL); Sigal Meirovitch, Tel-Aviv (IL); Daniel L. Siegel, Rechovot (IL)

(73) Assignees: Yissum Research Development Company of the Hebrew University of Jerusalem Ltd., Jerusalem (IL); CollPlant Ltd., Nes Ziona (IL)

( * ) Notice: Subject to any disclaimer, the term of this patent is extended or adjusted under 35 U.S.C. 154(b) by 139 days.

(21) Appl. No.: 12/744,703

(22) PCT Filed: Nov. 26, 2008

(86) PCT No.: PCT/IL2008/001542
§ 371 (c)(1),
(2), (4) Date: May 26, 2010

(87) PCT Pub. No.: WO2009/069123
PCT Pub. Date: Jun. 4, 2009

(65) Prior Publication Data
US 2010/0317588 A1 Dec. 16, 2010

Related U.S. Application Data

(60) Provisional application No. 60/996,581, filed on Nov. 26, 2007, provisional application No. 61/071,968, filed on May 28, 2008.

(51) Int. Cl.
*A61K 9/14* (2006.01)
(52) U.S. Cl.
USPC ........................................................ 424/484
(58) Field of Classification Search .................. 530/350; 435/69.1; 424/484
See application file for complete search history.

(56) References Cited

U.S. PATENT DOCUMENTS

2007/0099231 A1 5/2007 Elvin
2007/0275408 A1* 11/2007 Elvin .............................. 435/7.1

FOREIGN PATENT DOCUMENTS

| CN | 1390937 | 1/2003 |
|---|---|---|
| WO | WO 01/34091 | 5/2001 |
| WO | WO 2004/104042 | 12/2004 |
| WO | WO 2006/035442 | 4/2006 |
| WO | WO 2007/020449 | 2/2007 |
| WO | WO 2009/069123 | 6/2009 |

OTHER PUBLICATIONS

Levy et al., Engineering a bifunctional starch-cellulose cross-bridge protein, 2004, Biomaterials 25: 1841-1849.*

Response Dated Mar. 27, 2011 to Communication Pursuant to Article 94(3) EPC of Dec. 3, 2010 From the European Patent Office Re. Application No. 08853290.8.
Communication Relating to the Results of the Partial International Search Dated Apr. 21, 2009 From the International Searching Authority Re.: Application No. PCT/IL2008/001542.
International Search Report and the Written Opinion Dated Nov. 5, 2009 From the International Searching Authority Re.: Application No. PCT/IL2008/001542.
Office Action Dated Dec. 28, 2011 From the Israel Patent Office Re. Application No. 206004 and Its Translation Into English.
Communication Pursuant to Article 94(3) EPC Dated Dec. 3, 2010 From the European Patent Office Re. Application No. 08853290.8.
Abo et al. "Peptide Sequences for Sucrose Splitting and Glucan Binding Within Streptococcus Sobrinus Glucosyltransferase (Water-Insoluble Glucan Synthetase)", Journal of Bacteriology, 173(3): 989-996, Feb. 1991.
Ali et al. "Metal Catalyzed Oxidation of Tyrosine Residues by Different Oxidation Systems of Copper/Hydrogen Peroxide", Journal of Inorganic Biochemistry, 98: 173-184, 2004.
Gurley et al. "Upstream Sequences Required for Efficient Expression of a Soybean Heat Shock Gene", Molecular and Cellular Biology, 6(2): 559-565, Feb. 1986.
Hamel et al. "Nucleotide Sequence of a Brassica Napus Endochitinase Gene", Plant Physiology, 101: 1403, 1993.
Haynes et al. "Globular Proteins at Solid/Liquid Interfaces", Colloids and Surfaces B: Biointerfaces, 2: 517-566, 1994.
Hedrick et al. "Chitinase cDNA Cloning and mRNA Induction by Fungal Elicitor, Wounding, and Infection", Plant Physiology, 86: 182-186, 1988.
Honda et al. "Nucleotide Sequence of the Streptococcus Mutans GtfD Gene Encoding the Glucosyltransferase-S Enzyme", Journal of General Microbiology, 136: 2099-2105, 1990.
Jespersen et al. "Comparison of the Domain-Level Organization of Starch Hydrolases and Related Enzymes", Biochemical Journal, 280: 51-55, 1991.
Jones et al. "Isolation and Characterization of Genes Encoding Two Chitinase Enzymes From Serratia Marcescens", The EMBO Journal, 5(3): 467-473, 1986.
Kato et al. "The Hydrogen Peroxide/Copper Ion System, But Not Other Metal-Catalyzed Oxidation Systems, Produces Protein-Bound Dityrosine", Free Radical Biology & Medicine, 31(5): 624-632, 2001.
Klebl et al. "Molecular Cloning of A Cell Wall Exo-β-1,3-Glucanase From Saccharomyces Cerevisiae", Journal of Bacteriology, 171(11): 6259-6264, Nov. 1989.
Klee et al. "Agrobacterium-Mediated Plants Transformation and Its Further Applications to Plant Biology", Annual Review of Plant Physiology, 38: 467-486, 1987.
Kuranda et al. "Chitinase Is Required for Cell Separation During Growth of Saccharomyces Cerevisiae", The Journal of Biological Chemistry, 266(29): 19758-19767, Oct. 15, 1991.
Langer "Biomaterials in Drug Delivery and Tissue Engineering: One Laboratory's Experience", Accounts of Chemical Research, 33(2): 94-101, 2000.

(Continued)

*Primary Examiner* — Maryam Monshipouri

(57) ABSTRACT

Isolated polypeptides are disclosed comprising an amino acid sequence encoding a monomer of a fibrous polypeptide attached to a heterologous polysaccharide binding domain. Composites comprising same, methods of generating same and uses thereof are all disclosed.

14 Claims, 33 Drawing Sheets
(26 of 33 Drawing Sheet(s) Filed in Color)

OTHER PUBLICATIONS

Langer "Selected Advances in Drug Delivery and Tissue Engineering", Journal of Controlled Release, 62: 7-11, 1999.

Lawson et al. "Nucleotide Sequence and X-Ray Structure of Cyclodextrin Glycosyltransferase From Bacillus Circulans Strain 251, in A Maltose-Dependent Cystal Form", Journal of Molecular Biology, 236(Chap.2): 590-600, 1994.

Lazaris et al. "Spider Silk Fibers Spun From Soluble Recombinant Silk Produced in Mammalian Cells", Science, 295: 472-476, Jan. 18, 2002.

Lee et al. "Co- and Post-Translational Processing of the Hevein Preproprotein of Latex of the Rubber Tree (Hevea Brasiliensis)", The Journal of Biological Chemistry, 266(24): 15944-15948, Aug. 25, 1991.

Lehrer et al. "Ultraviolet Irradiation Effects in Poly-L-Tyrosine and Model Compounds. Identification of Bityrosine as A Photoproduct", Biochemistry, 6(3): 757-767, Mar. 1967.

Lerner et al. "The Gene for Stinging Nettle Lectin (Urtica Dioica Agglutinin) Encodes Both A Lectin and A Chitinase", The Journal of Biological Chemistry, 267(16): 11085-11091, Jun. 5, 1992.

Lim et al. "Cationic Hyperbranched Poly(Amino Ester): A Novel Class of DNA Condensing Molecule With Cationic Surface, Biodegradable Three-Dimensional Structure, and Tertiary Amine Groups in the Interior", Journal of the American Chemical Society, 123: 2460-2461, 2001.

Lucas et al "Amino-Terminal Sequence of Ethylene-Induced Bean Leaf Chitinase Reveals Similarities to Sugar-Binding Domains of Wheat Germ Agglutinin", The FEBS Letters, 193(2): 208-210, Dec. 1985.

Malencik et al. "Dityrosine Formation in Calmodulin: Cross-Linking and Polymerization Catalyzed by Arthromyces Peroxidase", Biochemistry, 35: 4375-4386, 1996.

Murray et al. "Dodon Usage in Plant Genes", Nucleic Acids Research, 17(2): 477-498, 1989.

Nazarov et al. "Porous 3-D Scaffolds From Regenerated Silk Fibroin", Biomacromolecules, 5: 718-726, 2004.

Neuhaus et al. "Plant Transformation by Microinjection Techniques", Physiologia Plantarum, 79: 213-217, 1990.

Nishizawa et al. "Rice Chitinase Gene: cDNA Cloning and Stress-Induced Expression", Plant Science, 76: 211-218, 1991.

Ohta "High-Efficiency Genetic Transformation of Maize by a Mixture of Pollen and Exogenous DNA", Proc. Natl. Acad. Sci. USA, 83; 715-719, Feb. 1986.

Ponstein et al. "A Novel Pathogen- and Wound-Inducible Tobacco (Nicotiana Tabacum) Protein With Antifungal Activity", Plant Physiology, 104: 109-118, 1994.

Potrykus "Gene Transfer to Plants: Assessment of Published Approaches and Results", Annual Review of Plant Physiology and Plant Molecular Biology, 42: 205-225, 1991.

Potter et al. "Regulation of A Hevein-Like Gene in Arabidopsis", Molecular Plant—Microbe Interactions, MPMI, 6(6): 680-685, 1993.

Raikhel et al. "Isolation and Characterization of A cDNA Clone Encoding Wheat Germ Agglutinin", Proc. Natl. Acad. Sci. USA, 84: 6745-6749, Oct. 1987.

Romero et al. "Sequence of the Streptococcus Pneumoniae Bacteriophage HB-3 Amidase Reveals High Homology With the Major Host Autolysin", Journal of Bacteriology, 172(9): 5064-5070, Sep. 1990.

Samac et al. "Isolation and Characterization of the Genes Encoding Basic and Acidic Chitinase in Arabidopsis Thaliana", Plant Physiology, 93: 907-914, 1990.

Sanford "Biolistic Plant Transformation", Physiologia Plantarum, 79: 206-209, 1990.

Scheller et al. "Production of Spider Silk Proteins in Tobacco and Potato", Nature Biotechnology, 19: 573-577, Jun. 2001.

Shareck et al. "Sequences of the Three Genes Specifying Xylanases in Streptomyces Lividans", Gene, 107: 75-82, 1991.

Shen et al. "Primary Sequence of the Glucanase Gene From Oerskovia Xanthineolytica", the Journal of Biological Chemistry, 266(2): 1058-1063, Jan. 15, 1991.

Shimamoto et al. "Fertile Transgenic Rice Plants Regenerated From Transformed Protoplasts", Nature, 338: 274-276, Mar. 16, 1989.

Shimoi et al. "Characterization of Rarobacter Faecitabidus Protease I, A Yeast-Lytic Serine Protease Having Mannose-Binding Activity", Journal of Biochemistry, 110: 608-613, 1991.

Shimoi et al. "Molecular Structure of Rarobacter Faecitabidus Protease I. A Yeast-Lytic Serine Protease Having Mannose-Binding Activity", The Journal of Biological Chemistry, 267(35): 25189-25195, Dec. 15, 1992.

Shiroza et al. "Sequence Analysis of the GtfB Gene From Streptococcus Mutans", Journal of Bacteriology, 169(9): 4263-4270, Sep. 1987.

Sidhu et al. "Streptomyces Griseus Protease C. A Novel Enzyme of the Chymotrypsin Superfamily", The Journal of Biological Chemistry, 269(31): 20167-20171, Aug. 5, 1994.

Sigurskjold et al. "Thermodynamics of Ligand Binding to the Starch-Binding Domain of Glucoamylase From Aspergillus Niger", European Journal of Biochemistry, 225: 133-144, 1994.

Smith et al. "Nucleotide Sequences of cDNA Clones Encoding Wheat Germ Agglutinin Isolectins A and D", Plant Molecular Biology, 13: 601-603, 1989.

Søgaard et al. "Site-Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-Amylase 1", The Journal of Biological Chemistry, 268(30): 22480-22484, Oct. 25, 1993.

Stanford et al. "Differential Expression Within a Family of Novel Wound-Induced Genes in Potato", Molecular and General Genetics, 215: 200-208, 1989. Abstract.

Studier et al. "Use of T7 RNA Polymerase to Direct Expression of Cloned Genes", Methods in Enzymology, 185(Art.6): 60-89, 1990.

Sun et al. "Cloning and DNA Sequencing of the Dextranase Inhibitor Gene (Dei) From Streptococcus Sobrinus", Journal of Bacteriology, 176(23): 7213-7222, Dec. 1994.

Svensson et al. "Sequence Homology Between Putative Raw-Starch Binding Domains From Different Starch-Degrading Enzymes", Biochemical Journal Letters, 264: 309-311, 1989.

Takamatsu et al. "Expression of Bacterial Chloramphenicol Acetyltransferase Gene in Tobacco Plants Mediated by TMV-RNA", The EMBO Journal, 6(2): 307-311, 1987.

Tomme et al. "Characterization and Affinity Applications of Cellulose-Binding Domains", Journal of Chromatography B, 715: 283-296, 1998.

Ueda et al. "Molecular Cloning and Nucleotide Sequence of the Gene Encoding Chitinase II From Aeromonas Sp. No. 10S-24", Journal of Fermentation and Bioengineering, 78(3): 205-211, 1994.

Ueda et al. "Sequence Analysis of the GtfC Gene From Streptococcus Mutans GS-5", Gene, 69: 101-109, 1988.

Uhrich et al. "Polymeric Systems for Controlled Drug Release", Chemical Reviews, 99: 3181-3198, 1999.

Vad et al. "Accumulation of Defense-Related Transcripts and Cloning of a Chitinase mRNA From Pea Leaves (Pisum Sativum L.) Inoculated With Ascochyta Pisi Lib.", Plant Science, 92: 69-79, 1993.

Villette et al. "Cyclomaltodextrin Glucanotransferase From Bacillus Circulans E 192", Biotechnology and Applied Biochemistry, 16: 57-63, 1992.

Von Eichel-Streiber et al. "Comparative Sequence Analysis of the Clostridium Difficile Toxins A and B", Molecular and General Genetics, 233: 260-268, 1992.

Wang et al. "A Novel Biogradable Gene Carrier Based on Polyphosphoester", Journal of the American Chemical Society, 123: 9480-9481, 2001.

Watanabe et al. "Structure of the Gene Encoding Chitinase D of Bacillus Circulans WL-12 and Possible Homology of the Enzyme to Other Prokaryotic Chitinases and Class III Plant Chitinases", Journal of Bacteriology, 174(2): 408-414, Jan. 1992.

Weis-Fogh "A Rubber-Like Protein in Insect Cuticle", Journal of Experimental Biology, 37(4): 889-907, 1960.

Weselake et al. "Inhibition of Alpha-Amylase-Catalyzed Starch Granule Hydrolysis by Cycloheptaamylose", Cereal Chemistry, 60(2): 98-101, 1983.

Wren et al. "Nucleotide Sequence of Clostridium Difficile Toxin A Gene Fragment and Detection of Toxigenic Strains by Polymerase Chain Reaction", FEMS Microbiology Letters, 70: 1-6, 1990.

Wright et al. "Primary Structure of Wheat Germ Agglutinin Isolectin 2. Peptide Order Deduced From X-Ray Structure", Biochemistry, 23: 280-287, 1984.

Wright et al. "Sequence Variability in Three Wheat Germ Agglutinin Isolectins: Products of Multiple Genes in Polyploid Wheat", Journal of Molecular Evolution, 28: 327-336, 1989.

Yahata et al. "Structure of the Gene Encoding β-1,3-Glucanase Al of Bacillus Circulans WL-12", Gene, 86: 113-117, 1990.

Yamagami et al. "The Complete Amino Acid Sequence of Chitinase-A From the Seeds of Rye (Secale Cereal)", Bioscence, Biotechnology, and Biochemistry, 58(2): 322-329, 1994.

Yanai et al. "Purification of Two Chitinases From Rhizopus Oligosporus and Isolation and Sequencing of the Encoding Genes", Journal of Bacteriology, 174(22): 7398-7406, Nov. 1992.

Yang et al. "Structure and Microporous Formation of Cellulose/Silk Fibroin Blend Membranes. I. Effect of Coagulants", Journal of Membrane Science, 177: 153-161, 2000.

Yother et al. "Structural Properties and Evolutionary Relationships of PspA, A Surface Protein of Strptococcus Pneumoniae, as Revealed by Sequence Analysis", Journal of Bacteriology, 174(2): 601-609, Jan. 1992.

Lewis et al. "Expression and Purification of A Spider Silk Protein: A New Strategy for Producing Repetitive Proteins", Protein Expression and Purification, 7: 400-406, 1996.

Díaz et al. "EJ-1, A Temperate Bacteriophage of Streptococcus Pneumoniae Eith A Myoviridae Morphotype", Journal of Bacteriology, 174(17): 5516-5525, Sep. 1992.

Duvic et al. "Purification and Characterization of A β-1,3-Glucan Binding Protein From Plasma of the Crayfish Pacifastacus Leniusculus", the Journal of Biological Chemistry, 265(16): 9327-9332, Jun. 5, 1990.

García et al. "Modular Organization of the Lytic Enzymes of Streptococcus Pneumoniae and Its Bacteriophages", Gene, 86: 81-88, 1990.

García et al. "Molecular Evolution of Lytic Enzymes of Streptococcus Pneumoniae and Its Bacteriophages", Proc. Natl. Acad. Sci. USA, 85: 914-918, Feb. 1988.

García et al. "Nucleotide Sequence and Expression of the Pneumococcal Autolysin Gene Fron Its Own Promoter in *Escherichia coli*", Gene, 43: 265-272, 1986.

Seki et al. "Horseshoe Crab (1,3)-β-D-Glucan-Sensitive Coagulation Factor G. A Serine Protease Zymogen Heterodimer With Similarities to β-Glucan-Binding Proteins", The Journal of Biological Chemistry, 269(2): 1370-1374, Jan. 14, 1994.

Shosejov et al. "Sp1 as A Thermostable Protein Scaffold Building Block for Self-Assembly of Composite Materials", Symposium DD: From Biological Materilas to Biomimetic Material Synthesis, XP002546728, [Online], MRS Spring Meeting San Francisco, CA, USA, Mar. 24-28, 2008, DD3.6, Mar. 26, 2008. Abstract.

Tsujibo et al. "Cloning, Sequence, and Expression of A Chitinase Gene From a Marine Bacterium, Alteromonas Sp. Strain O-7", Journal of Bacteriology, 175(1): 176-181, Jan. 1993.

Watanabe et al. "Gene Cloning of Chitinase A1 From Bacillus Circulans WL-12 Revealed Its Evolutionary Relationship to Serratia Chitinase and to the Type III Homology Units of Fibronectin", The Journal of Biological Chemistry, 265(26): 15659-15665, Sep. 15, 1990.

Yahata et al. "Structure of the Gene Encoding β-1,3-Glucanase A1 of Bacillus Circulans WL-12", Gene, 86: 113-117, 1990.

Barroso et al. "Nucleotide Sequence of Clostridium Difficile Toxin B Gene", Nucleic Acids Research, 18(13): 4004, May 25, 1990. EMBL Accession No. X53138.

Beerhues et al. "Primary Structure and Expression of mRNAs Encoding Basic Chitinase and 1,3-β-Glucanase in Potato", Plant Molecular Biology, 24: 353-367, 1994.

Belshaw et al. "Specificity of the Binding Domain of Glucoamylase 1", European Journal of Biochemistry, 211: 717-724, 1993.

Bitter et al. "Expression and Secretion Vectors for Yeast", Methods in Enzymology, 153: 516-544, 1987.

Booth et al. "The Use of A 'Universal' Yeast Expression Vector to Produce An Antigenic Protein of Mycobacterium Leprae", Immunology Letters, 19: 65-70, 1988.

Boraston et al. "Carbohydrate-Binding Modules: Fine-Tuning Polysaccharide Recognition", Biochemical Journal, 382: 769-781, 2004.

Brisson et al. "Expression of a Bacterial Gene in Plants by Using A Viral Vector", Nature, 310: 511-514, Aug. 9, 1984.

Broekaert et al. "Antimicrobial Peptides From Amaranthus Caudatus Seeds With Sequence Homology to the Cysteine/Glycine-Rich Domain of Chitin-Binding Proteins", Biochemistry, 31: 4308-4314, 1992.

Broekaert et al. "Wound-Induced Accumulation of mRNA Containing A Hevein Sequence in Laticifers of Rubber Tree (Hevea Brasiliensis)", Proc. Natl. Acad. Sci. USA, 87: 7633-7637, Oct. 1990.

Broglie et al. "Ethylene-Regulated Gene Expression: Molecular Cloning of the Genes Encoding An Endochitinase From Phaseolus Vulgaris ", Proc. Natl. acad. Sci. USA, 83: 6820-6824, Sep. 1986.

Broglie et al. "Functional Analysis of DNA Sequences Responsible for Ethylene Regulation of a Bean Chitinase Gene in Transgenic Tobacco", The Plant Cell, 1: 599-607, Jun. 1989.

Broglie et al. "Light-Regulated Expression of a Pea Ribulose-1,5-Bisphosphate Carboxylase Small Subunit Gene in Transformed Plant Cells", Science, 224: 838843, May 25, 1984.

Chen et al. "Isolation and Characterization of A Novel Chitosan-Binding Protein From Non-Headling Chinese Cabbage Leaves", Journal of Integrative Plant Biology, 47(4): 452-456, 2005.

Clarke et al. "Wound-Induced and Developmental Activation of A Poplar Tree Chitinase Gene Promoter in Transgenic Tobacco", Plant Molecular Biology, 25: 799-815, 1994.

Coruzzi et al. "Tissue-Specific and Light-Regulated Expression of A Pea Nuclear Gene Encoding the Small Subunit of Ribulose-1,5-Bisphosphate Carboxylase", The EMBO Journal, 3(8): 1671-1684, 1984.

Davis et al. "Populus Chitinase Genes: Structure, Organization, and Similarity of Translated Sequences to Herbaceous Plant Chitinases", Plant Molecular Biology, 17: 631-639, 1991.

De Block et al. "Expression of Foreign Genes in Regenerated Plants and in Their Progeny", The EMBO Journal, 3(8): 1681-1689, 1984.

Diaz et al. "EJ-1, A Temperate Bacteriophage of *Streptococcus Pneumoniae* Eith A Myoviridae Morphotype", Journal of Bacteriology, 174(17): 5516-5525, Sep. 1992.

Duvic et al. "Purification and Characterization of a β-1,3-Glucan Binding Protein From Plasma of the Crayfish Pacifastacus Leniusculus ", the Journal of Biological Chemistry, 265(16): 9327-9332, Jun. 5, 1990.

Fahnestock et al. "Production of Synthetic Spider Daragline Silk Protein in Pichia Pastoris ", Applied Microbiology and Biotechnology, 47: 33-39, 1997.

Fahnestock et al. "Synthetic Spider Dragline Silk Proteins and Their Production in *Escherichia Coli*", Applied Microbiology and Biotechnology, 47: 23-32, 1997.

Favier et al. "Mechanical Percolation in Cellulose Whisker Nanocomposites", Polymer Engineering and Science, 37(10): 1732-1739, Oct. 1997.

Ferretti et al. "Nucleotide Sequence of a Glucosyltransferase Gene From *Streptococcus Sobrinus* MFe28", Journal of Bacteriology, 169(9): 4271-4278, Sep. 1987.

Fromm et al. "Stable Transformation of Maize After Gene Transfer by Electroporation", Nature, 319: 791-793, Feb. 27, 1987.

Fukuda et al. "Specific Inhibition by Cyclodextrins of Raw Starch Digestion by Fungal Glucoamylase", Bioscience, Biotechnology, and Biochemistry, 56(4): 556-559, 1992.

Garcia et al. "Modular Organization of the Lytic Enzymes of *Streptococcus Pneumoniae* and Its Bacteriophages", Gene, 86: 81-88, 1990.

Garcia et al. "Molecular Evolution of Lytic Enzymes of *Streptococcus Pneumoniae* and Its Bacteriophages", Proc. Natl. Acad. Sci. USA, 85: 914-918, Feb. 1988.

Garcia et al. "Nucleotide Sequence and Expression of the Pneumococcal Autolysin Gene Fron Its Own Promoter in *Escherichia Coli*", Gene, 43: 265-272, 1986.

Gardella et al. "Expression of Human Parathyroid Hormone-(1-84) in *Escherichia Coli* as a Factor X-Cleavable Fusion Protein", The Journal of Biological Chemistry, 265(26): 15854-15859, Sep. 15, 1990.

Giffard et al. "Molecular Characterization of a Cluster of at Least Two Glucosyltransferase Genes in *Strptococcus Salivarius* ATCC 25975", Journal of General Microbiology, 137: 2577-2593, 1991.

Gilboa et al. "Transfer and Expression of Cloned Genes Using Retroviral Vectors", BioTechniques, 4(6): 504-512, 1986.

Gilkes et al. "Domains in Microbial β-1,4-Glycanases: Sequence Conservation, Function, and Enzyme Families", Microbiological Reviews, 55(2): 303-315, Jun. 1991.

Adams et al. "RecName: Full=Pro-Resilin; Flags: Precursor", Database UniProt [Online], XP002519331, Retrieved From EBI Accession No. UNIPROT:Q9V7U0, Database Accession No. Q9V7U0, May 1, 2000.

Adams et al. "The Genome Sequence of Drosophila Melanogaster", Science, XP000961051, 287(5461): 2185-2195, Mar. 24, 2000. p. 2185-2195.

Ardell et al. "Tentative Identification of A Resilin Gene in Drosophila Melanogaster ", Insect Biochemistry and Molecular Biology, XP002998361, 31(10): 965-970, Sep. 1, 2001. p. 965-970.

Elvin et al. "Synthesis and Properties of Crosslinked Recombinant Pro-Resilin", Nature, XP002407576, 437(7061): 999-1002, Oct. 13, 2005. p. 999-1002.

Kim et al. "High Yield Expression of Recombinant Pro-Resilin: Lactose-Induced Fermentation in *E. Coli* and Facile Purification", Protein Expression & Purification, 52: 230-236, 2007.

Levy et al. "Engineering a Bifunctional Starch-Cellulose Cross-Bridge Protein", Biomaterials, XP004485099, 25(10): 1841-1849, May 1, 2004. p. 1841-1849.

Levy et al. "Recombinant Cellulose Crosslinking Protein: A Novel Paper-Modification Biomaterial", Cellulose 9: 91-98, 2002.

Lyons et al. "Design and Facile Production of Recombinant Resilin-Like Polypeptides: Gene Construction and A Rapid Protein Purification Method", Protein Engineering, Design & Selection, 20(1): 25-32, Jan. 11, 2007.

Meirovitch et al. "Protein Engineering of Cellulose—Spider Silk Composite", Poster Abstract Presented at the MRS Spring Meeting Symposium T: The Nature of Design—Utilizing Biology's Portfolio, XP002519708, {Online], Apr. 10-13, 2007, p. 1-10, Apr. 10, 2007. Retrieved From the Internet. Abstract.

Noishiki et al. "Mechanical Properties of Silk Fibroin-Microcrystalline Cellulose Composite Films", Journal of Applied Polymer Science, 86: 3425-3429, 2002.

Outchkourov et al. "The Promoter—Terminator of Chrysanthemum RbcS1 Directs Very High Expression Levels in Plants", Planta, XP002519330, 216(6): 1003-1012, Apr. 2003. p. 1003-1012.

Shosejov et al. "Spl as A Thermostable Protein Scaffold Building Block for Self-Assembly of Composite Materials", Symposium DD: From Biological Materilas to Biomimetic Material Synthesis, XP002546728, [Online], MRS Spring Meeting San Francisco, CA, USA, Mar. 24-28, 2008, DD3.6, Mar. 26, 2008. Abstract.

Shoseyov et al. "Carbohydrate Binding Modules: Biochemical Properties and Novel Applications", Microbiology and Molecular Biology Reviews, XP002496582, 70(2): 283-295, Jun. 2006. p. 283-295.

Vendrely et al. "Biotechnological Production of Spider-Silk Proteins Enables New Applications", Macromolecular Bioscience, XP002546726, 7(4): 401-409, Apr. 10, 2007. p. 401-409.

\* cited by examiner

FIG. 2

COMPOSITIONS COMPRISING FIBROUS POLYPEPTIDES AND POLYSACCHARIDES

RELATED APPLICATIONS

This application is a National Phase of PCT Patent Application No. PCT/IL2008/001542 having International filing date of Nov. 26, 2008, which claims the benefit of U.S. Provisional Patent Application Nos. 61/071,968 filed on May 28, 2008 and 60/996,581 filed on Nov. 26, 2007. The contents of the above applications are all incorporated herein by reference.

FIELD AND BACKGROUND OF THE INVENTION

The present invention, in some embodiments thereof, relates to compositions comprising fibrous polypeptides and polysaccharides and uses of same.

The most extensively investigated biological polymers for use in material science are polysaccharides due to their abundance and extremely diverse mechanical properties.

The polysaccharide cellulose is the most common biopolymer on earth. Although it is mostly found in plant biomass, it is also produced by animals, fungi and bacteria. Cellulose is a crystalline assembly of cellobiose subunits which are made from glucose. Due to its crystalline structure, cellulose has high tensile strength and elasticity approaching that of synthetic carbon fibers, and it has a very favorable strength/weight ratio compared to, for example, steel. In plant cell walls, cellulose is found as a composite with other polysaccharides such as hemicellulose, pectin, lignin, enzymes and structural proteins. These molecules link the cellulose microfibrils improving the mechanism of load transfer when the cell is subjected to mechanical stress whilst enhancing physical protection against pathogen attack.

The unique properties of natural biocomposites have prompted many scientists to produce composites of cellulose and synthetic polymer matrixes. For example, Favier et al, [Polymer engineering and science 37(10): 1732-1739] produced cellulose-latex composites resulting in increased shear modulus by more than three orders of magnitude of the latex rubbery state. Such biocomposites have been produced for the automotive industries and for production of biodegradable plastics.

The use of cellulose binding domains (CBD) for cellulose fiber modification is a well established technology [Shoseyov et al, Microbiol Mol Biol Rev. 70(2):283-95]. Recently, CBD was used for production of novel cellulose-protein composite materials when recombinant CBD or CBD dimers, CBD-CBD fusion proteins (CCP), were bound to paper resulting in improved mechanical and water repelling properties [Levy et al., Cellulose 9: 91-98]. Furthermore, a recombinant CBD-starch binding domain (CSCP) demonstrated cross-bridging ability in different model systems composed of insoluble or soluble starch and cellulose [Levy et al., Cellulose 9: 91-98].

In addition to polysaccharide research, biopolymer research has focused in recent years on fibrous proteins due to their unique mechanical properties. These proteins are distinguished by their repetitive amino acid sequences that confer mechanical strength or flexibility. Among these proteins are mammalian collagen and elastin and the arthropod proteins, silkworm silk (*Bombyx morii*), spider dragline silk and resilin. The unique repetitive sequence of each protein confers its mechanical properties. For instance, spider silk is extremely strong while resilin and elastin are extremely elastic and resilient with a rubber-like nature.

Resilin is found in specialized cuticle regions in many insects, especially in areas where high resilience and low stiffness are required, or as an energy storage system. It is best known for its roles in insect flight and the remarkable jumping ability of fleas and spittlebugs. The protein was initially identified in 1960 by Weis-Fogh who isolated it from cuticles of locusts and dragonflies and described it as a rubber-like material.

Resilin displays unique mechanical properties that combine reversible deformation with very high resilience. It has been reported to be the most highly efficient elastic material known. The elastic efficiency of the material is purported to be 97%; only 3% of stored energy is lost as heat (U.S. Patent Application 20070099231). Resilin shares similar mechanical properties with elastin which is produced in connective tissues of vertebrates. In humans, elastin is usually found at sites where elasticity is required, such as the skin and cartilage (often in association with collagen). Elastin-collagen composites also serve as a major component in arterial walls where it allows the blood vessels to smooth the pulsatile flow of blood from the heart into a continuous and steady flow.

In spite of their functional analogy, the sequence homology between resilin and elastin is very low, apart from the high abundance of glycine in both proteins. Nevertheless, the elasticity of both proteins results from their architecture of randomly coiled, crosslinked polypeptide chains. Resilin is synthesized in the insect cytoplasm and subsequently secreted to the cuticle where peroxidase enzymes catalyze its polymerization via formation of di/tri tyrosine bridges, resulting in assembly of a natural protein-carbohydrate composite material with cuticular chitin. Two *Drosophila melanogaster* Resilin mRNA variants have been identified—CG15920-RA and CG15920-RB which differ in the truncation of their chitin binding domains (see FIG. 1A). The major components that were annotated are the 17-amino acid long elastic repeats and the 35 amino acid-long chitin binding domain of type R&R.

Recently, Elvin et al., 2005, [Nature. 437: 999-1002] successfully expressed and polymerized a synthetic, truncated resilin-like gene in *E. coli*. The synthetic gene consists of the 17 repeats of the native gene. The protein, once expressed, undergoes photochemical crosslinking which casts it into a rubber-like biomaterial. U.S. Patent Application 20070099231 discloses hybrid resilins comprising resilin and structural polypeptides.

Silk proteins are produced by a variety of insects and arachnids, the latter of which form the strongest silk polymers on earth. The spider spins as many as seven different kinds of silks, each one being optimized to its specific biological function in nature. Dragline silk, used as the safety line and as the frame thread of the spider's web, is an impressive material with a combination of tensile strength and elasticity. Its extraordinary properties are derived from its composition as a semicrystalline polymer, comprising crystalline regions embedded in a less organized "amorphous" matrix. The crystalline regions consist of antiparallel β-pleated sheets of polyalanine stretches that give strength to the thread, while the predominant secondary structure of the amorphous matrix is the glycine-rich helix which provides elasticity. Most dragline silks consist of at least two different proteins with molecular masses of up to several hundred kDa. On the basis of sequence similarities, dragline silk proteins have been grouped into spidroinl-like (MaSp1) and spidroin2-like (MaSp2) proteins.

As opposed to silkworm silk, isolation of silk from spiders is not industrially feasible. Spiders produce silk in small quantities, and their territorial behavior prevents large amounts thereof from being harvested in adjacent quarters.

Therefore, production of silk protein through recombinant DNA techniques is preferred. For such purposes, widespread use is made of synthetic genes based on a monomer consensus of the native spidroin sequences. These synthetic genes have been successfully expressed in the methyltropic yeast host, *Pichia pastoris*, in *E. coli* and in the tobacco and potato plants [Fahnestock S R., and Bedzyk L A Appl Microbiol biotechnol 47:33-39 (1997); Fahnestock S R., and Bedzyk L A, Appl Microbiol biotechnol 47:23-32 (1997), Sceller J. et al. Nature biotechnology 19:573-577 (2001)]. Through such means, laboratory scale amounts of silk-like protein powders are readily available. The final hurdle on the way to the production of manmade silks lies in the development of an appropriate spinning technology capable of converting these powders into high performance fibers. The tendency of these proteins to aggregate in-vitro, bypassing the protein folding process, acts as a significant limitation toward successfully producing functional silk. The assembly of the proteins from a liquid crystalline form into a solid silk string is extremely complex, and duplication of the operational function of spider spinning glands remains a major challenge.

Several attempts have been reported on the preparation of cellulose-silk fibroin composites which were prepared by molecular blending and regeneration of solubilized cellulose and silkworm silk [Freddi G, et al., (1995), J Appl Polymer Sci 56: 1537-1545; Yang, G, et al., (2000) J Membr Sci 210: 177-153]. Recently, Noishiki et al [Noishiki Y, Nishiyama Y, Wada M, Kuga S, Magoshi J. (2002) J Appl Polymer Sci 86: 3425-3429] prepared composite cellulose-silk films from solid cellulose whiskers and regenerated silkworm silk, resulting in notably improved mechanical strength, with breaking strength and ultimate strain about five times those of the constituent materials alone.

SUMMARY OF THE INVENTION

According to an aspect of some embodiments of the present invention there is provided an isolated polypeptide comprising an amino acid sequence encoding a monomer of a fibrous polypeptide attached to a heterologous polysaccharide binding domain, with the proviso that the polysaccharide binding domain is not a cellulose binding domain.

According to an aspect of some embodiments of the present invention there is provided an isolated polypeptide comprising an amino acid sequence encoding a resilin or spider-silk polypeptide attached to a heterologous polysaccharide binding domain.

According to an aspect of some embodiments of the present invention there is provided an isolated polynucleotide comprising a nucleic acid sequence encoding an isolated polypeptide comprising an amino acid sequence encoding a monomer of a fibrous polypeptide attached to a heterologous polysaccharide binding domain, with the proviso that the polysaccharide binding domain is not a cellulose binding domain.

According to an aspect of some embodiments of the present invention there is provided an isolated polynucleotide comprising a nucleic acid sequence encoding an isolated polypeptide comprising an amino acid sequence encoding a resilin or spider-silk polypeptide attached to a heterologous polysaccharide binding domain.

According to an aspect of some embodiments of the present invention there is provided a nucleic acid construct, comprising a nucleic acid sequence encoding resilin and a cis-acting regulatory element capable of directing an expression of the resilin in a plant.

According to an aspect of some embodiments of the present invention there is provided a nucleic acid construct, comprising a nucleic acid sequence encoding spider silk and a cis-acting regulatory element capable of directing an expression of the spider silk in a plant.

According to an aspect of some embodiments of the present invention there is provided a nucleic acid construct, comprising the isolated polynucleotides of the present invention.

According to an aspect of some embodiments of the present invention there is provided a cell comprising the nucleic acid constructs of the present invention.

According to an aspect of some embodiments of the present invention there is provided a plant cell comprising the nucleic acid constructs of the present invention.

According to an aspect of some embodiments of the present invention there is provided an isolated composite comprising a fibrous polypeptide and a polysaccharide, the fibrous polypeptide being resilin or spider silk.

According to an aspect of some embodiments of the present invention there is provided an isolated composite comprising a fibrous polypeptide and a polysaccharide, the fibrous polypeptide comprising a heterologous polysaccharide binding domain, the composite being non-immobilized.

According to an aspect of some embodiments of the present invention there is provided an isolated composite comprising at least two non-identical fibrous polypeptides, wherein a first fibrous polypeptide of the at least two non-identical fibrous polypeptide is an isolated polypeptide comprising an amino acid sequence encoding a monomer of a fibrous polypeptide attached to a heterologous polysaccharide binding domain, with the proviso that the polysaccharide binding domain is not a cellulose binding domain.

According to an aspect of some embodiments of the present invention there is provided an isolated composite comprising at least two non-identical fibrous polypeptides, wherein a first fibrous polypeptide of the at least two non-identical fibrous polypeptide is an isolated polypeptide comprising an amino acid sequence encoding a resilin or spider-silk polypeptide attached to a heterologous polysaccharide binding domain.

According to an aspect of some embodiments of the present invention there is provided a method of generating the isolated composites of the present invention, the method comprising contacting the fibrous polypeptide with the polysaccharide under conditions which allow binding between the fibrous polypeptide and the polysaccharide to generate the isolated composites of the present invention.

According to an aspect of some embodiments of the present invention there is provided a use of the isolated composite of the present invention for the manufacture of a medicament for the treatment of a cartilage or bone disease or condition.

According to an aspect of some embodiments of the present invention there is provided a use of the isolated composite of the present invention for the manufacture of a medicament for the treatment of urinary incontinence.

According to an aspect of some embodiments of the present invention there is provided a scaffold comprising the isolated composite of the present invention.

According to an aspect of some embodiments of the present invention there is provided a method of treating a cartilage or bone disease or condition, the method comprising administering to a subject in need thereof a therapeutically effective amount of the isolated composite of the present invention, thereby treating the cartilage disease or condition.

According to an aspect of some embodiments of the present invention there is provided a method of treating urinary incontinence, the method comprising administering to a subject in need thereof a therapeutically effective amount of the isolated composite of the present invention, thereby treating urinary incontinence.

According to an aspect of some embodiments of the present invention there is provided a pharmaceutical composition comprising the isolated composite of the present invention.

According to an aspect of some embodiments of the present invention there is provided a cosmetic composition comprising the isolated composite of the present invention.

According to some embodiments of the invention, the fibrous polypeptide is selected from the group consisting of resilin, elastin, spider silk, silk-worm silk, collagen and mussel byssus protein.

According to some embodiments of the invention, the fibrous polypeptide comprises resilin.

According to some embodiments of the invention, the fibrous polypeptide comprises spider silk.

According to some embodiments of the invention, the resilin comprises an amino acid sequence as set forth in SEQ ID NO: 8.

According to some embodiments of the invention, the resilin comprises an amino acid sequence as set forth in SEQ ID NO: 9

According to some embodiments of the invention, the polypeptide further comprises an amino acid sequence as set forth in SEQ ID NOs: 52 or 53.

According to some embodiments of the invention, the polysaccharide binding domain is selected from the group consisting of a chitin binding domain, a starch binding domain, a dextran binding domain, a glucan binding domain, a chitosan binding domain, an alginate binding domain and an hyaluronic acid binding domain.

According to some embodiments of the invention, the polysaccharide binding domain is selected from the group consisting of a chitin binding domain, a cellulose binding domain, a starch binding domain, a dextran binding domain, a glucan binding domain, a chitosan binding domain, an alginate binding domain and an hyaluronic acid binding domain.

According to some embodiments of the invention, the isolated polypeptide is as set forth in SEQ ID NOs: 11-13 and SEQ ID NOs. 32-36.

According to some embodiments of the invention, the spider silk comprises an amino acid sequence as set forth in SEQ ID NO: 16 or SEQ ID NO: 26.

According to some embodiments of the invention, the polynucleotide comprises a nucleic acid sequence selected from the group consisting of SEQ ID NO: 17-22, 24, 28 and 29.

According to some embodiments of the invention, the nucleic acid construct further comprises at least one cis-acting regulatory element.

According to some embodiments of the invention, the cis-acting regulatory element is a plant promoter.

According to some embodiments of the invention, the plant promoter is a rbcS1 promoter.

According to some embodiments of the invention, the nucleic acid construct further comprises a nucleic acid sequence encoding a vacuolar signal sequence.

According to some embodiments of the invention, the cis-acting regulatory sequence is a terminator sequence.

According to some embodiments of the invention, the terminator sequence is a rbcS1 sequence.

According to some embodiments of the invention, the cell is a plant cell.

According to some embodiments of the invention, the polysaccharide is selected from the group consisting of chitin, cellulose, starch, dextran, glucan, chitosan, alginate and hyaluronic acid.

According to some embodiments of the invention, the fibrous polypeptide comprises a polysaccharide binding domain.

According to some embodiments of the invention, the polysaccharide binding domain is a heterologous polysaccharide binding domain.

According to some embodiments of the invention, the polysaccharide binding domain comprises a chitin binding domain, a cellulose binding domain, a chitosan binding domain, an alginate binding domain, a starch binding domain, a dextran binding domain, a glucan binding domain and an hyaluronic acid binding domain.

According to some embodiments of the invention, the fibrous polypeptide is selected from the group consisting of mussel byssus protein, resilin, silkworm silk protein, spider silk protein, collagen, elastin or fragments thereof.

According to some embodiments of the invention, the isolated composite further comprises an additional fibrous polypeptide, wherein the additional fibrous polypeptide is different to the fibrous polypeptide, the additional fibrous polypeptide being selected from the group consisting of mussel byssus protein, resilin, silkworm silk protein, spider silk protein, collagen, elastin and fragments thereof.

According to some embodiments of the invention, the isolated composite is crosslinked.

According to some embodiments of the invention, the isolated composite is non-crosslinked.

According to some embodiments of the invention, the method further comprises crosslinking the composite following the contacting.

According to some embodiments of the invention, the crosslinking is affected by a method selected from the group consisting of photochemical crosslinking, enzymatic crosslinking, chemical crosslinking and physical crosslinking.

According to some embodiments of the invention, the method further comprises coating the composite with an additional fibrous polypeptide, the coating being effected following the crosslinking the composite.

According to some embodiments of the invention, the method further comprises binding the fibrous polypeptide with an additional fibrous polypeptide prior to the contacting.

According to some embodiments of the invention, the additional fibrous polypeptide is selected from the group consisting of a mussel byssus protein, spider silk protein, collagen, elastin, and fibronectin, and fragments thereof.

According to some embodiments of the invention, the polysaccharide is selected from the group consisting of a chitin, a cellulose, a starch, a dextran, a glucan, a chitosan, an alginate, a carboxymethyl cellulose and an hyaluronic acid.

According to some embodiments of the invention, the use is for cartilage repair, knee repair, meniscus repair a knee lubricant and disc repair.

According to some embodiments of the invention, the administering is effected locally.

According to some embodiments of the invention, the locally administering is effected by intra-articular administration.

According to some embodiments of the invention, the intra-articular administration comprises administration into a joint selected from the group consisting of a knee, an elbow, a hip, a sternoclavicular, a temporomandibular, a carpal, a tarsal, a wrist, an ankle, an intervertebral disk and a ligamentum flavum.

According to some embodiments of the invention, the cartilage disease or condition is selected from the group consisting of osteoarthritis, limited joint mobility, gout, rheumatoid arthritis, osteoarthritis, chondrolysis, scleroderma, degenerative disc disorder and systemic lupus erythematosus.

According to some embodiments of the invention, the administering is effected by injection into an area surrounding the urethra.

According to some embodiments of the invention, the composition is formulated as a gel, a strip, an injectable, or a foam.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
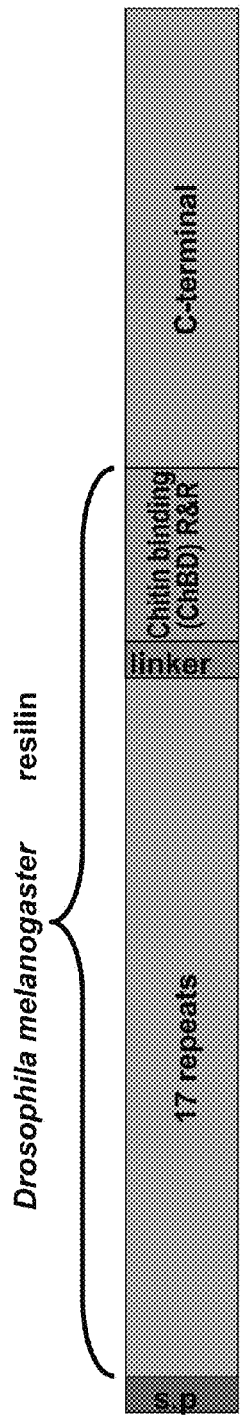
Figure 1B:
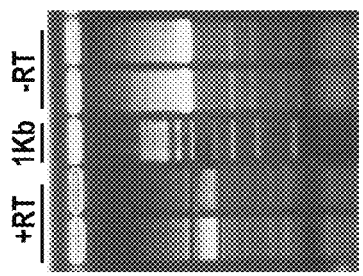

FIGS. 1A-B is a schematic illustration (FIG. 1A) and scan (FIG. 1B) illustrating the size and structure of the resilin gene from *D. melonogaster*. FIG. 1A illustrates the schematic structure of *Drosophila melanogaster* resilin variant A CG15920-RA gene; S.P.; cuticular signal peptide, ChBD R&R; chitin binding domain type R&R. Variant B CG15920-RB contains a truncated chitin binding domain. FIG. 1B illustrates RT-PCR results of amplification of the resilin gene from *D. melonogaster*. The resilin cDNA is highlighted by the red rectangle. The thick band was formed due to the presence of two resilin variants. The band in the control reaction lanes (-RT) indicates the genomic gene that contains one intron and therefore migrates slower than the RT-PCR product.

Figure 2:
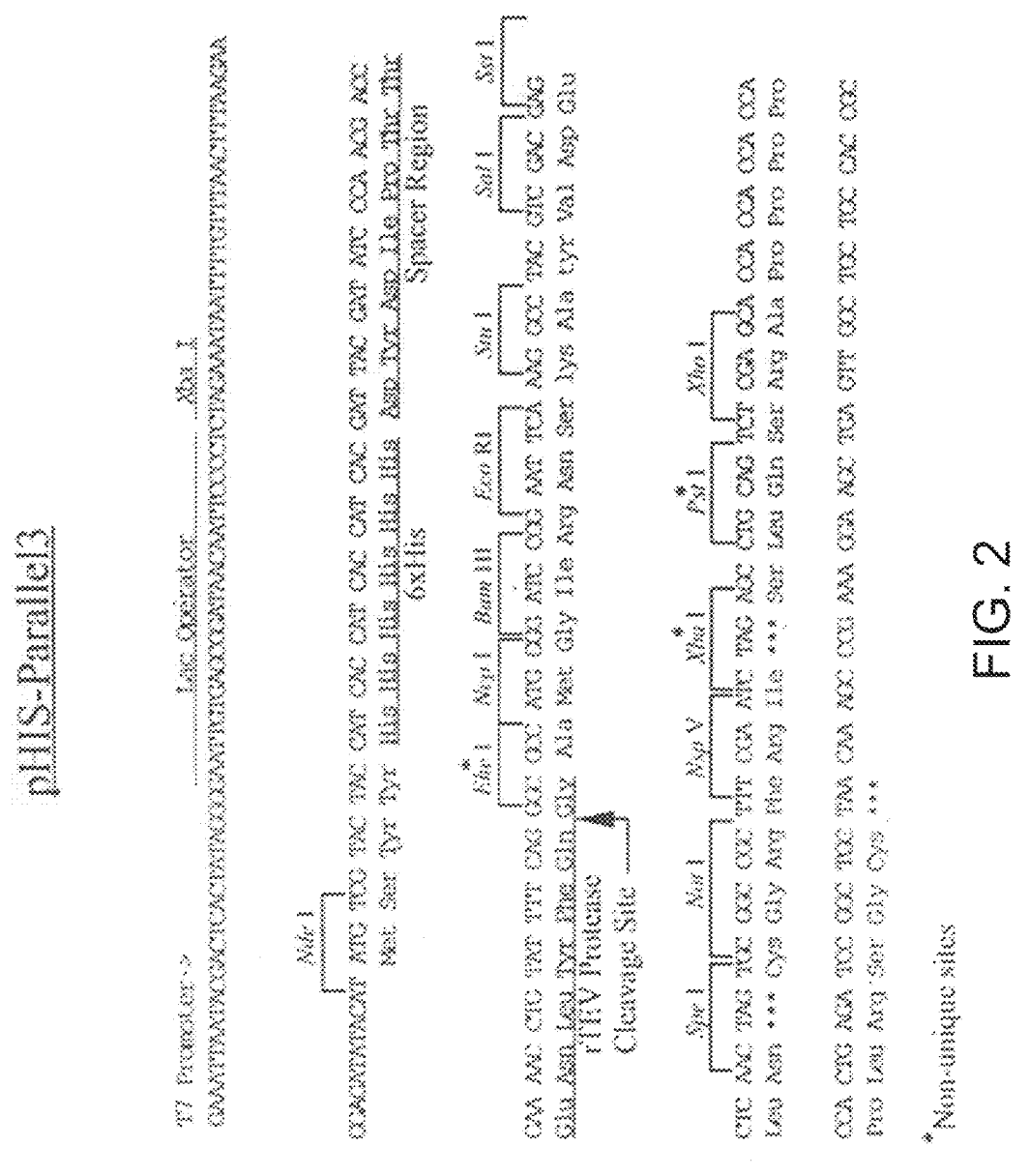

FIG. 2 is a scheme of the multiple cloning site of the pHis-parallel3 expression vector (SEQ ID NO: 54).

Figures 3A, 3B:
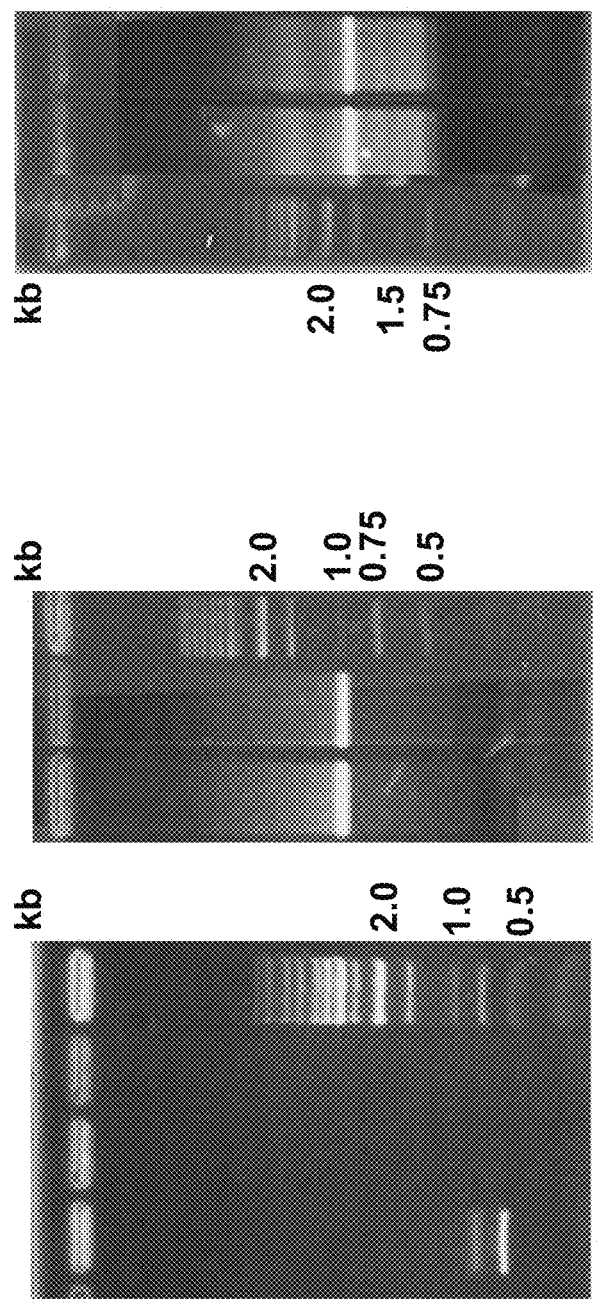

FIGS. 3A-B are scans of PCR results of CBD-Resilin (SEQ ID NO: 18) construction. FIG. 3A illustrates the first round PCR of the separate reactions of CBD (left) and resilin (right) sequence amplification. The CBD sequence contains a resilin-matching overhang on the 3' prime while the Resilin contains CBD-matching overhang on the 5' prime. FIG. 3B illustrates the PCR result of the second round following mixture of 1 µl of both products from round one. Note the increased molecular weight of the linked sequences.

Figure 4:
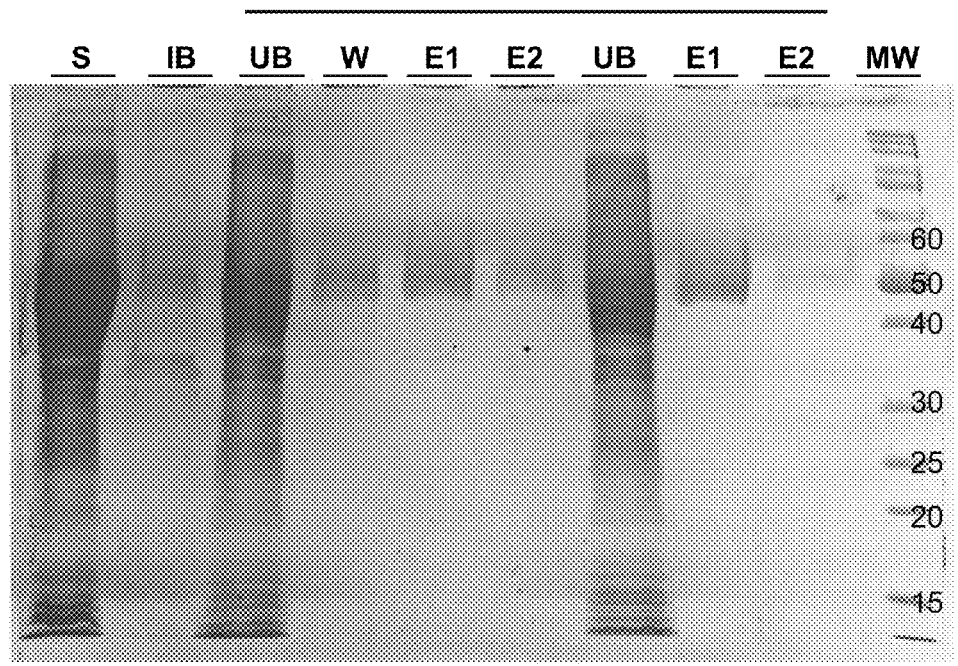

FIG. 4 is a scan of a Coomassie blue-stained SDS PAGE analysis of a small scale batch purification of 6H-Res-ChBD (SEQ ID NO: 55) expressed in bacteria. S: soluble protein fraction of the lyzed cells; IB: inclusion bodies; UB: unbound fraction removed by centrifugation; W: wash; E1,E2: eluted protein with 0.4M imidazole. MW: protein molecular weight marker.

Figure 5:
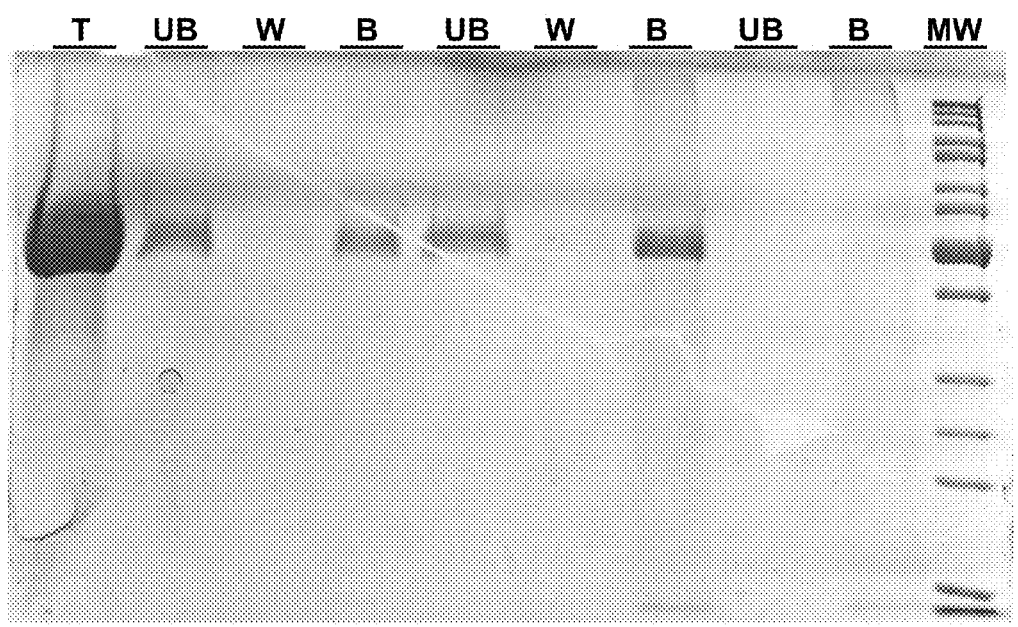

FIG. 5 is a scan of a Coomassie blue-stained SDS PAGE analysis illustrating the results of a cellulose and chitin binding assay with the affinity-purified 6H-Res-ChBD protein (SEQ ID NO: 55). T: Protein pulled down by HIS-Select® affinity product; UB: unbound fraction removed by centrifugation; W: wash fraction; B: bound fraction eluted from cellulose/chitin pellets by boiling with SDS-PAGE sample application buffer. MW: molecular weight marker.

Figure 6A:
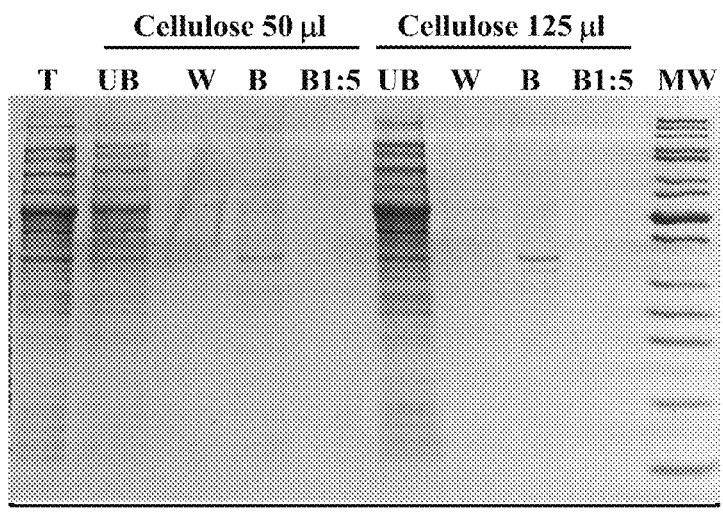
Figure 6B:
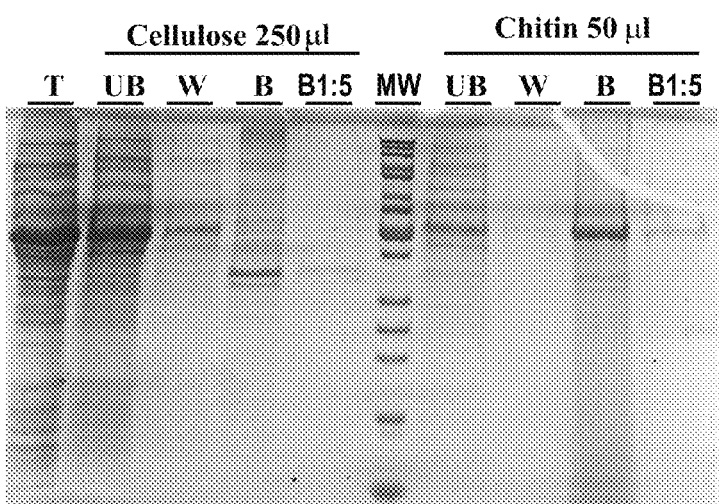
Figure 6C:
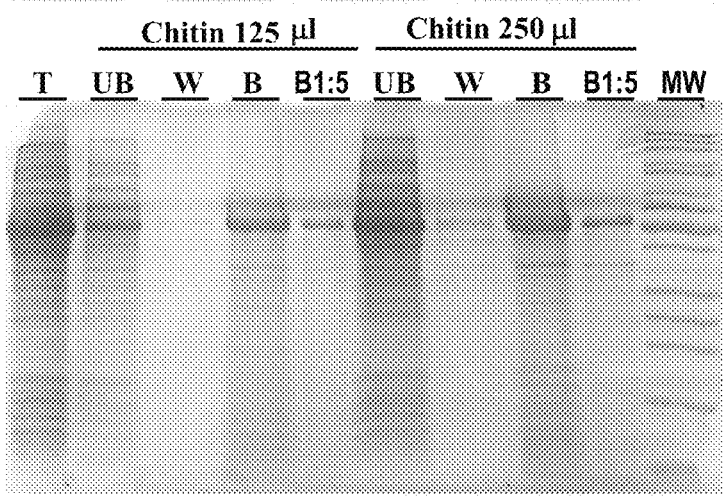

FIGS. 6A-C are scans of Coomassie blue-stained SDS PAGE analyses illustrating the results of a cellulose and chitin binding assay of a crude extract comprising 6H-Res-ChBD (SEQ ID NO: 55). T: crude lysate; W: wash fraction UB; unbound fraction removed by centrifugation; B: bound fraction eluted from cellulose/chitin pellets by boiling with SDS-PAGE sample application buffer. B 1:5: bound fraction diluted five time to the true initial load concentration. MW: protein molecular weight marker.

Figure 7:
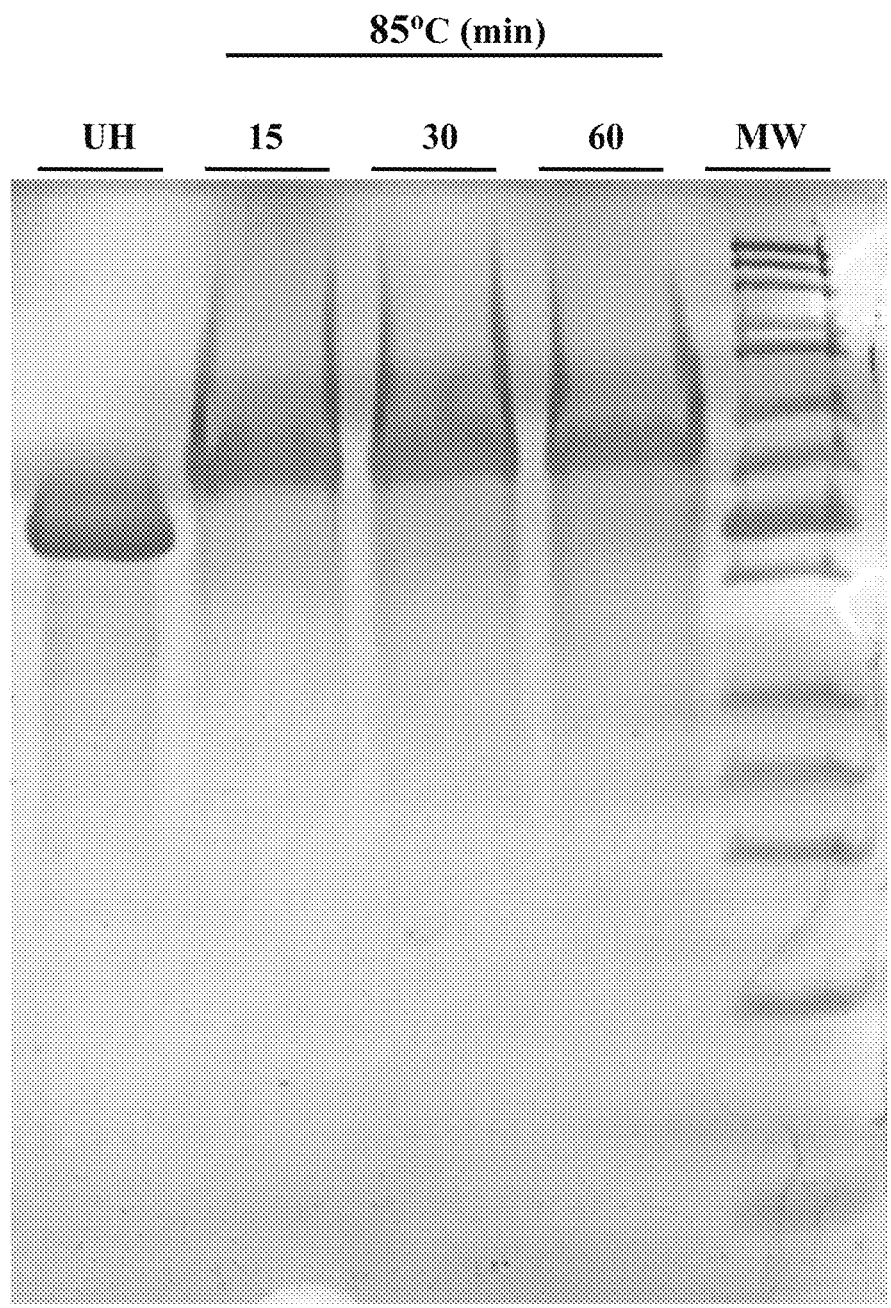

FIG. 7 is a photograph of an SDS PAGE analysis illustrating the results of a Res-ChBD (SEQ ID NO: 55) heat stability assay. UH: unheated protein. Lanes 2-4: samples subjected to 85° C. for 15, 30, 60 minutes, respectively. MW: protein molecular weight marker.

Figure 8A:
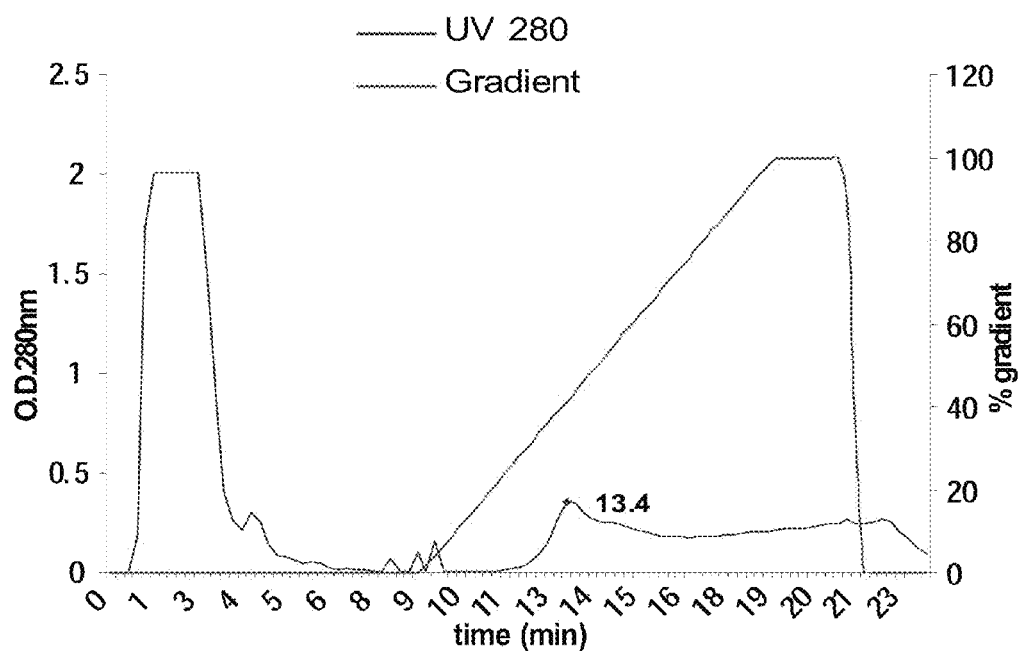
Figure 8B:
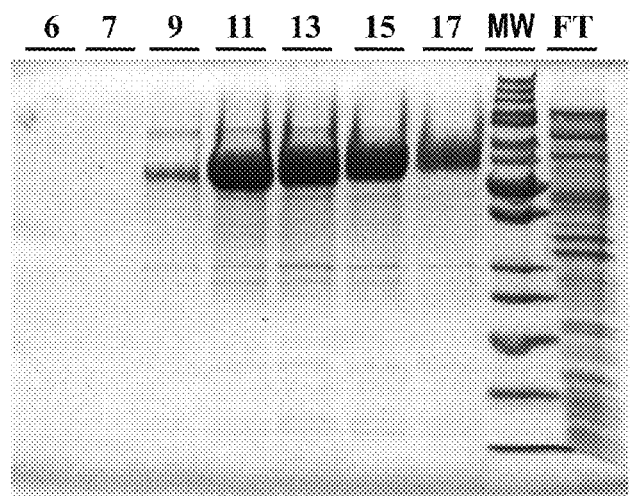

FIGS. 8A-B illustrate a small scale affinity purification of 6H-Res-ChBD. FIG. 8A: Chromatogram illustrating purification of Res-ChBD on a Ni-NTA column. The observed peak was eluted with 220 mM imidazole at min 13.4. FIG. 8B: SDS-PAGE analysis of small scale Ni-NTA purification of 6H-Res-ChBD (SEQ ID NO: 55). 6-17: number of FPLC fractions loaded on the gel; FT: column flow through. Fractions 9-18 were collected for further analysis.

Figure 9:
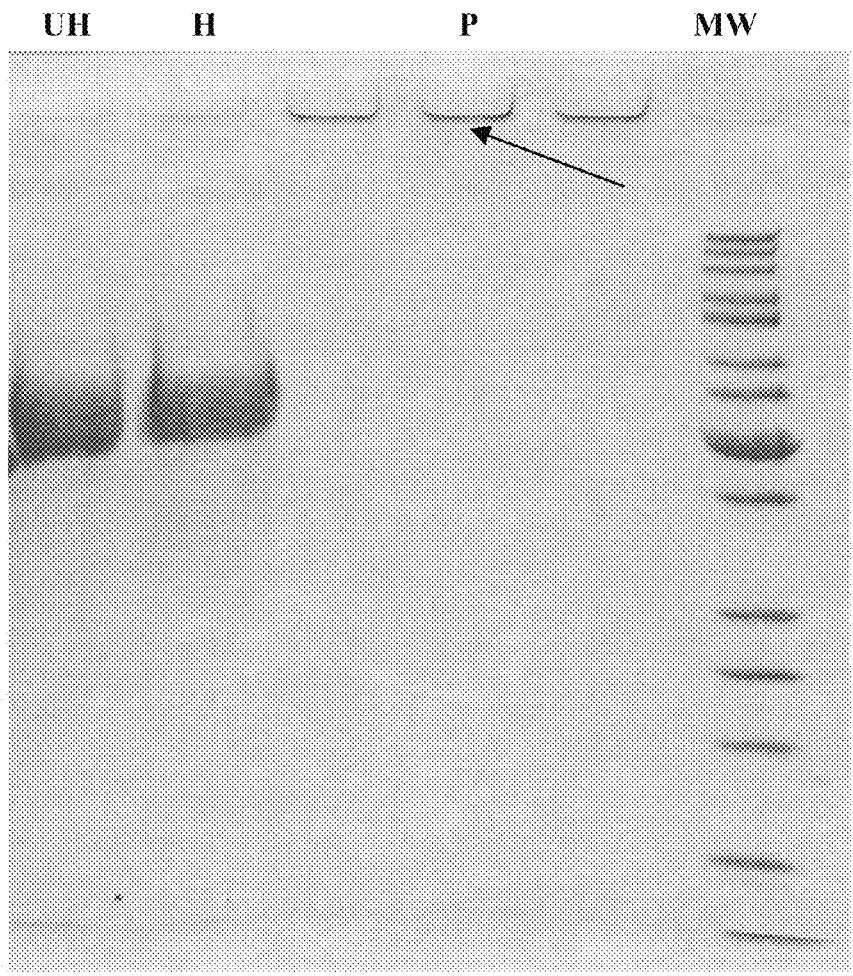

FIG. 9 is a scan of an SDS-PAGE analysis of photochemical polymerization of 6H-Res-ChBD (SEQ ID NO: 55). UH: unheated affinity purified 6H-Res-ChBD; H: purified 6H-Res-ChBD incubated at 85° C. for 15 minutes; P: 6H-Res-ChBD treated with $Ru(bpy)_3Cl_2.6H_2O$ and ammonium persulfate prior to subjection to sunlight. The treatment resulted in high molecular weight products that could not get into the gel and remained in the loading wells (indicated by arrow).

Figure 10A:
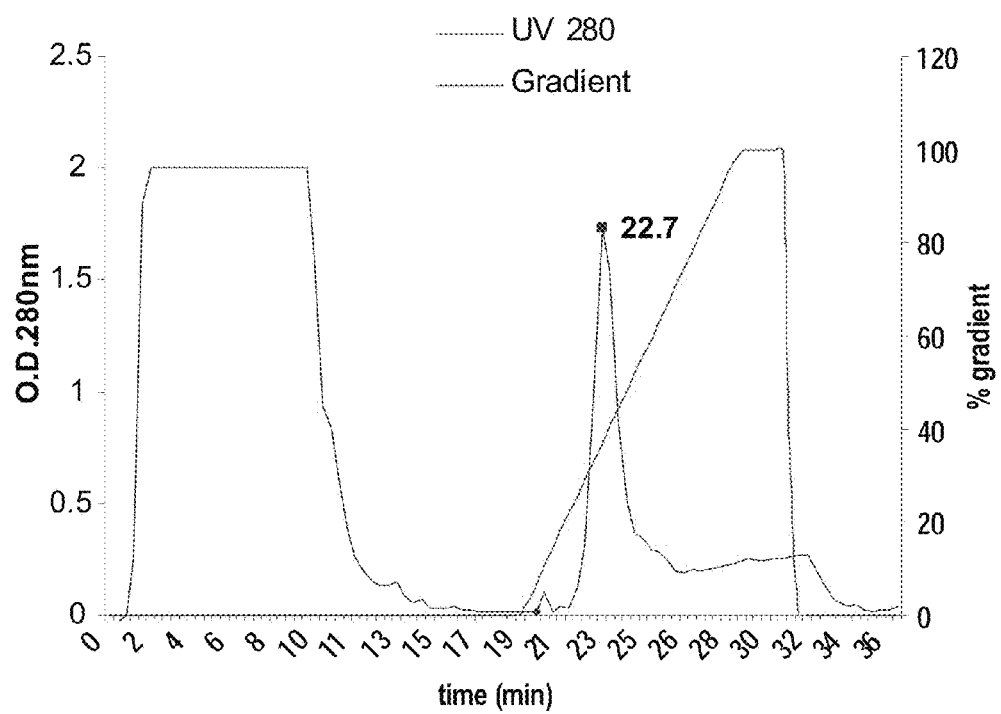
Figure 10B:
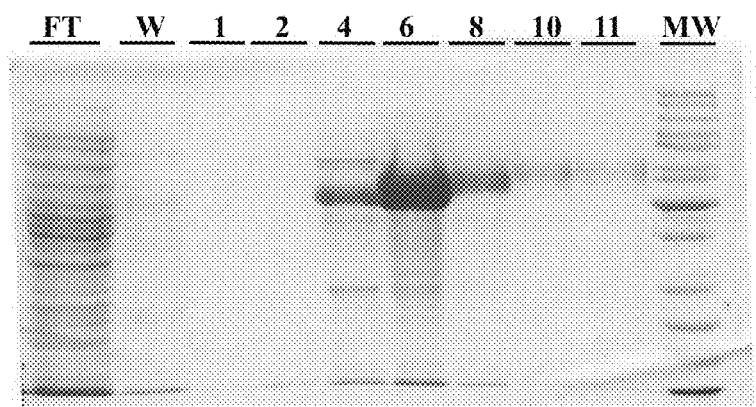

FIGS. 10A-B illustrate a medium scale affinity purification of 6H-Res-ChBD (SEQ ID NO: 55). FIG. 10A: Chromatogram of 6H-Res-ChBD purification on a Ni-NTA column. The protein peak observed was eluted with 180 mM imidazole at min 22.7. FIG. 10B: Coomassie blue stained SDS-PAGE analysis of a medium scale Ni-NTA purification of 6H-Res-ChBD. 1-11: numbers of FPLC fractions loaded on the gel; FT: column flow through; W: column wash.

Figure 11:
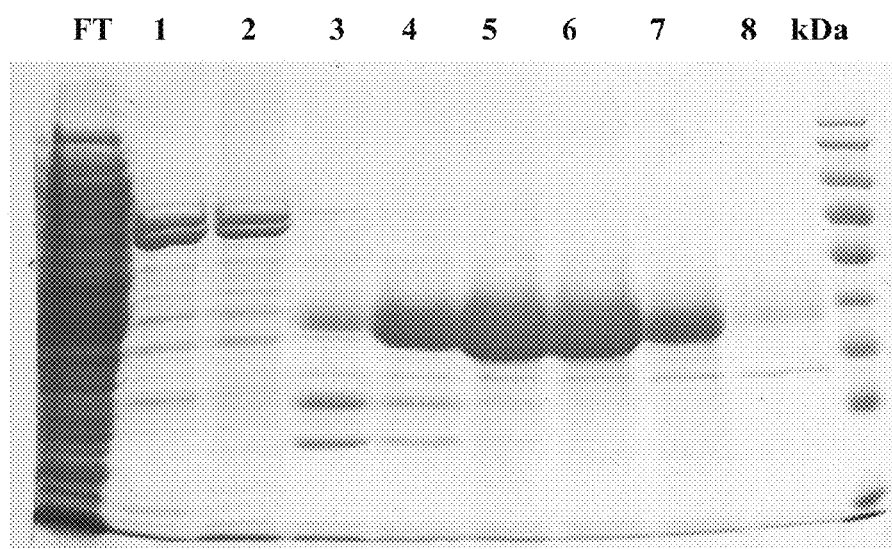

FIG. 11 is a scan of a Coomassie-blue stained SDS-PAGE analysis of a Ni-NTA-purified recombinant resilin (SEQ ID NO: 56). Lanes 1-8: FPLC fractions; FT: column flow through. Fractions 4-7 correspond to the purified resilin.

Figure 12:
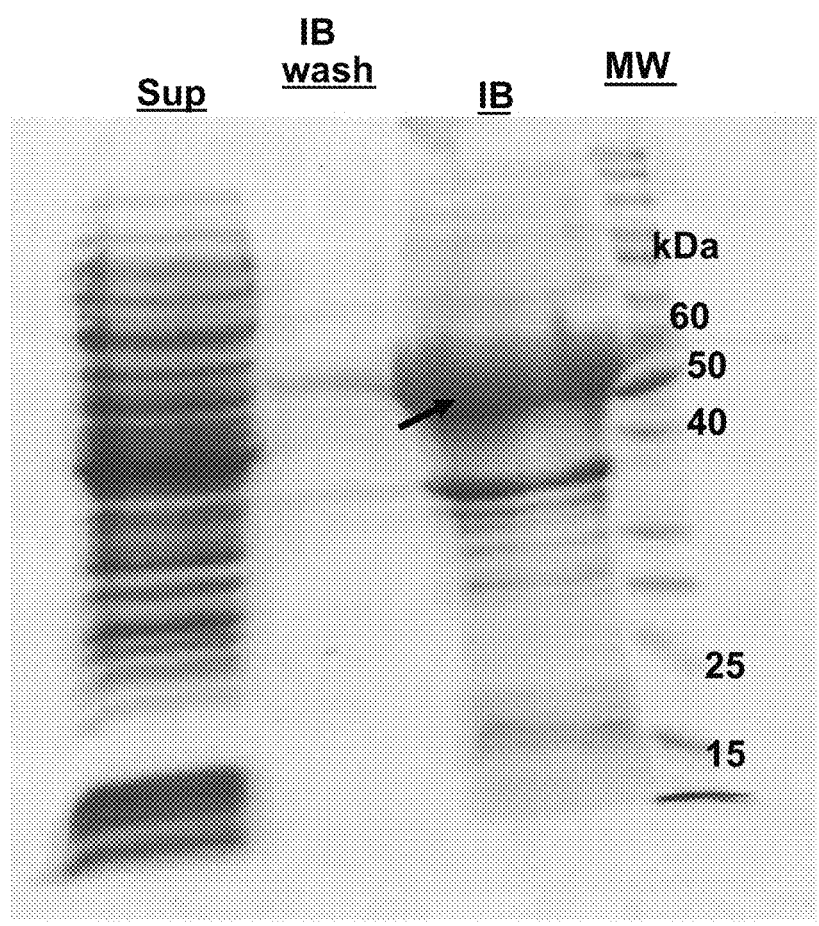

FIG. 12 is a scan of a Coomassie blue stained SDS-PAGE analysis of CBD-resilin (SEQ ID NO: 57), marked by the arrow, post lysis of the bacteria. The protein was detected almost exclusively in the inclusion bodies (IB).

Figure 13:
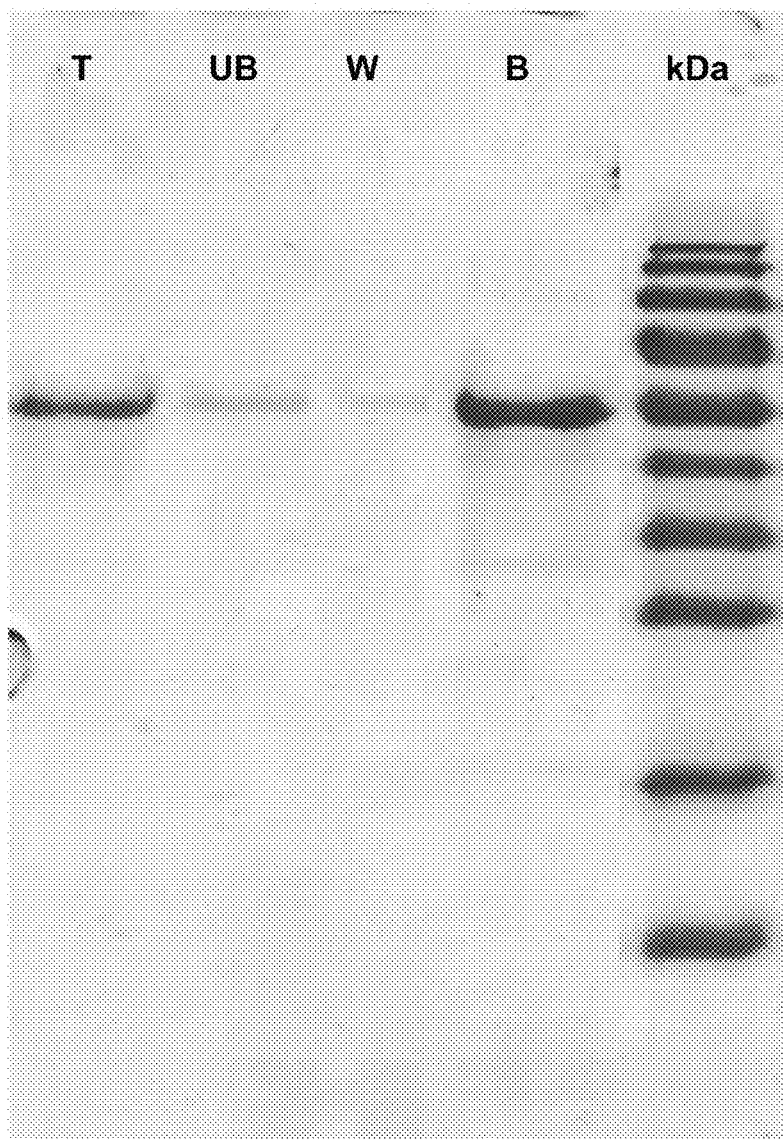

FIG. 13 is a scan of a Coomassie blue stained SDS-PAGE analysis of the cellulose binding capacity of affinity purified CBD-resilin (SEQ ID NO: 57). T: Ni-NTA purified CBD-resilin; UB: unbound fraction removed by centrifugation; W: wash fraction; B: bound fraction eluted from cellulose/chitin pellets by boiling with SDS-PAGE sample application buffer.

Figure 14:
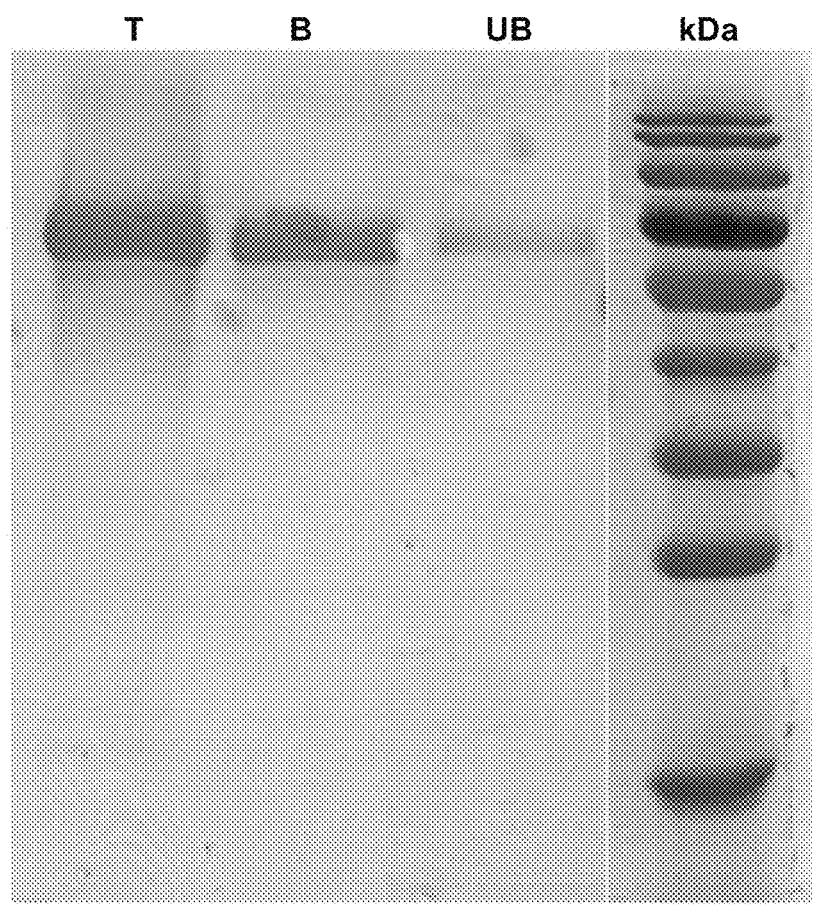

FIG. 14 is a scan of a Coomassie blue stained SDS-PAGE analysis of CBD-resilin refolded via the Aktaprime™ Plus FPLC automated refolding system (SEQ ID NO: 57) bound to cellulose. T; Ni-NTA purified CBD-resilin; B: bound fraction eluted from cellulose pellets by boiling with SDS-PAGE sample application buffer; UB: unbound fraction removed by centrifugation.

Figure 15:
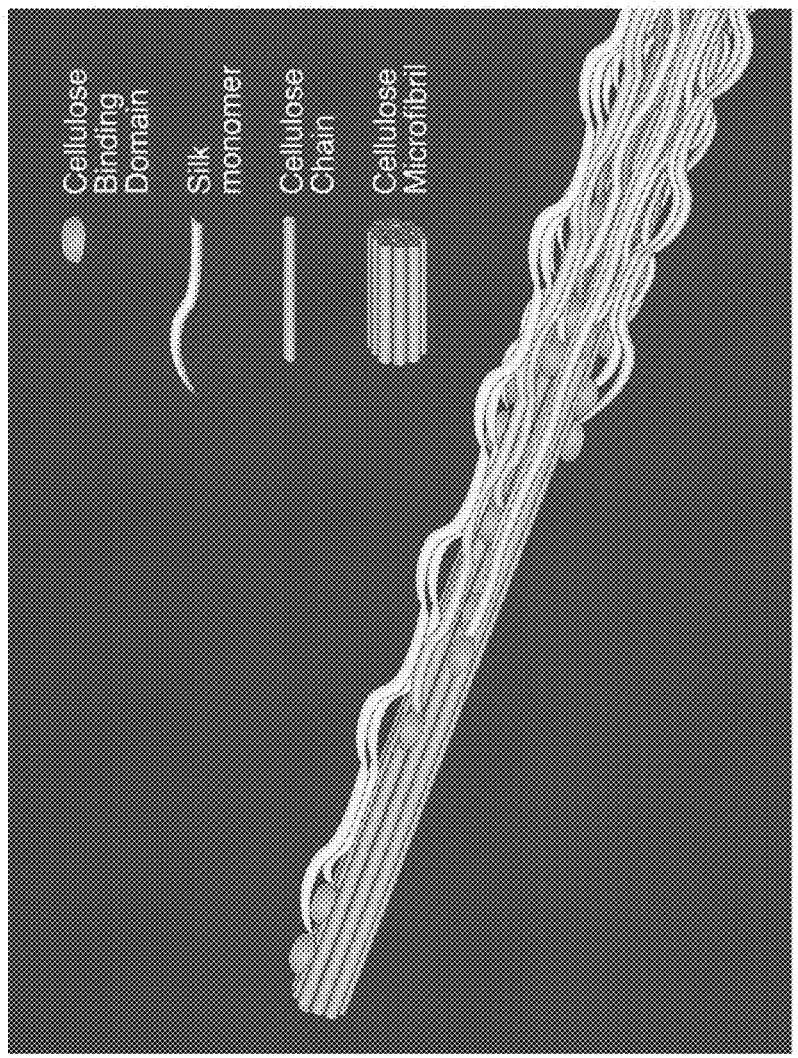

FIG. 15 is a model of a composite of cellulose and spider silk.

Figure 16:
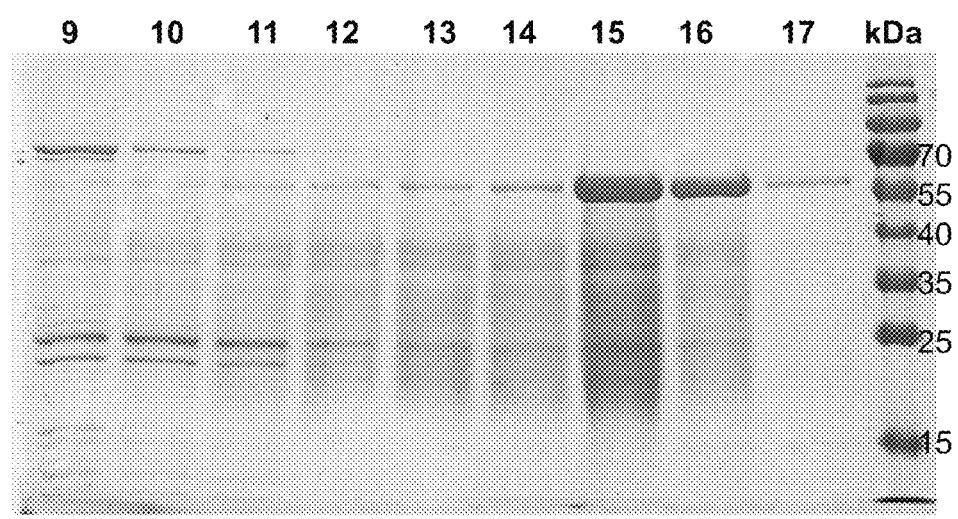

FIG. 16 is a scan of a Coomassie-stained SDS-PAGE analysis of Ni-NTA purified recombinant resilin-CBD (SEQ ID NO: 58). Samples 9-17 were the FPLC-ÄKTAprime™ plus fractions. Fractions 15-16 correspond to the resilin-CBD peak as observed at O.D. 280 nm.

Figure 17:
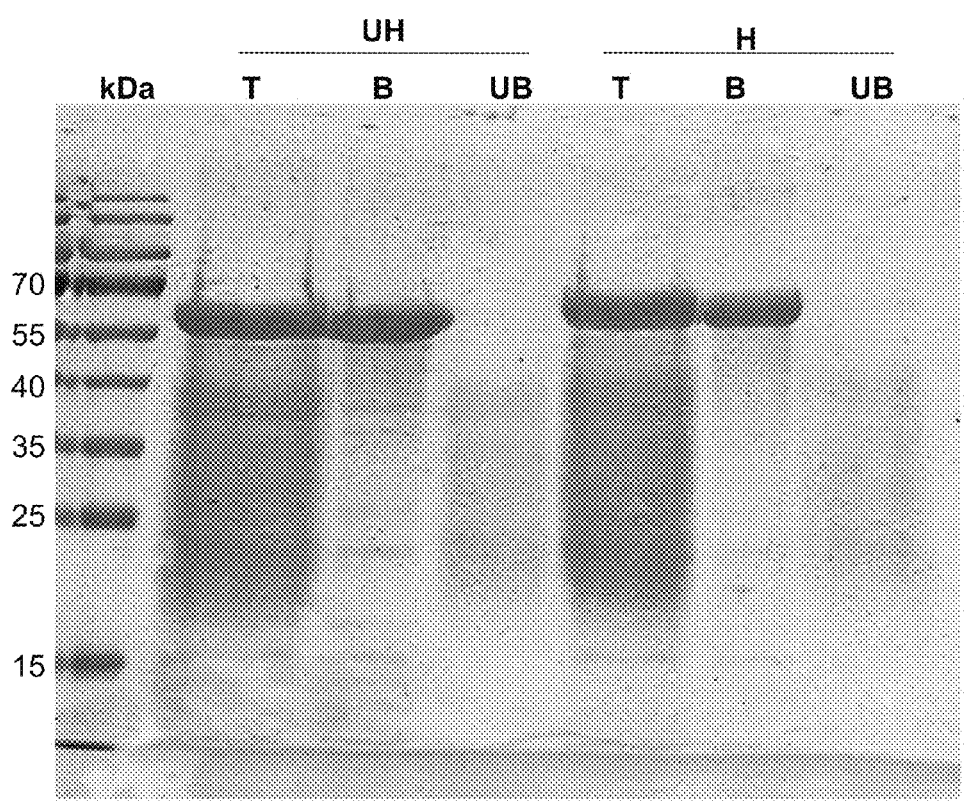

FIG. 17 is a scan of a Coomassie-stained SDS-PAGE analysis of resilin-CBD (SEQ ID NO: 58) following heat treatment and a cellulose binding assay. UH: Unheated protein; H: Protein incubated at 85° C. for 15 minutes; T: Total protein (affinity chromatography product); B: Bound fraction eluted by boiling the cellulose pellet with X2 SAB; UB: Unbound fraction removed by centrifugation.

Figure 18:
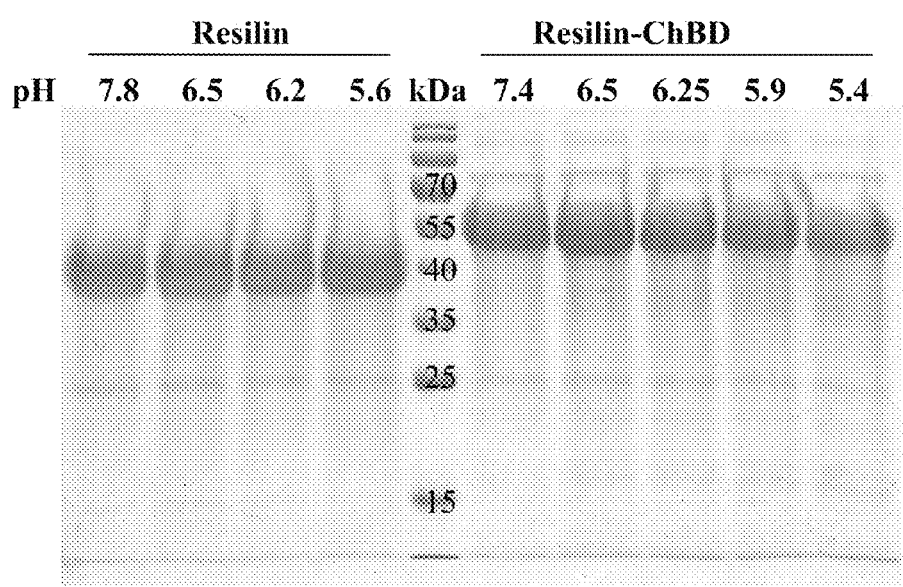

FIG. 18 is a scan of a Coomassie-stained SDS-PAGE analysis of the solubility of resilin (SEQ ID NO: 56) and resilin-ChBD (SEQ ID NO: 55) proteins under different pH conditions, following gradual titration with 2M HCl.

Figure 19:
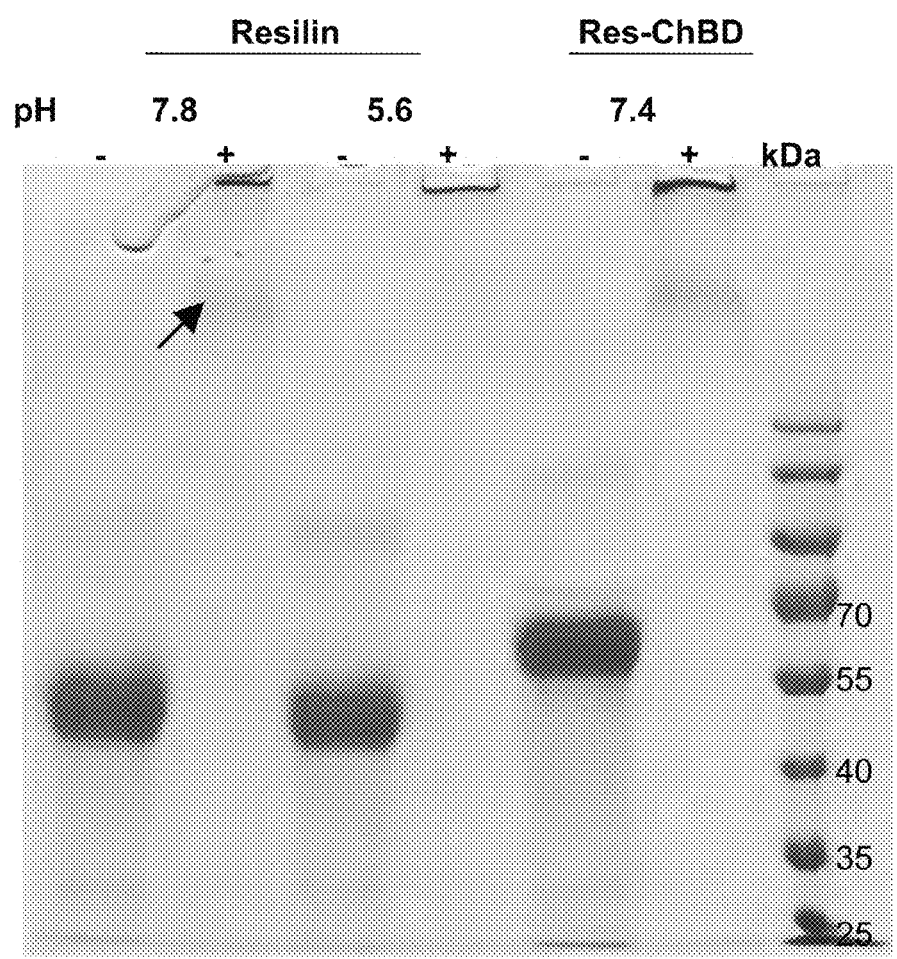

FIG. 19 is a scan of a Coomassie-stained SDS-PAGE analysis of resilin samples that were subjected to light-induced polymerization under different pH conditions in the presence (+) or absence (−) of Ru(bpy)$_3$Cl$_2$.6H$_2$O and APS. Control samples of Res-ChBD (SEQ ID NO: 55) proteins (pH 7.4) were subjected to similar crosslinking conditions. The arrow points out the high molecular weight products in samples containing the crosslinkers.

Figure 20:
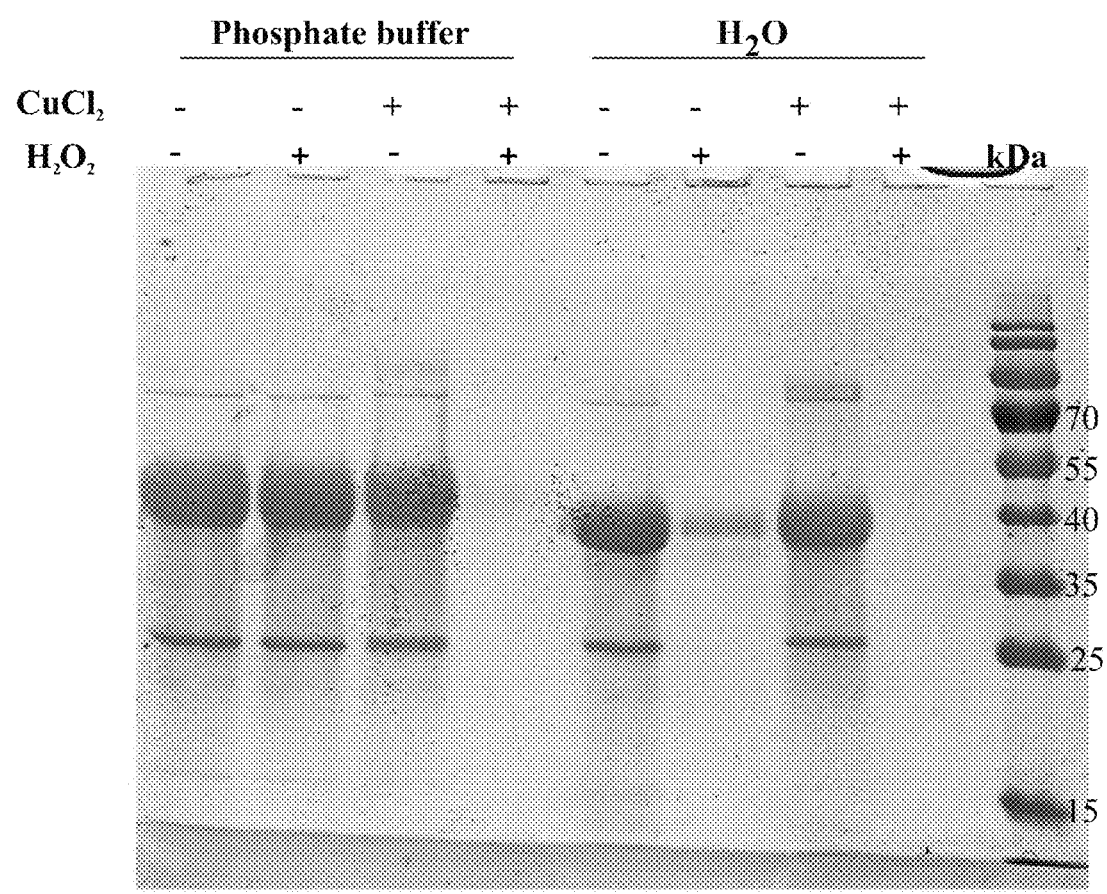

FIG. 20 is a scan of a Coomassie-stained SDS-PAGE analysis of resilin polymerized by the MCO method in either a phosphate buffer or water-based reaction solution. A high molecular weight product was formed both in phosphate buffer and H$_2$O. The reaction carried out in H$_2$O demonstrated a polymerization effect in the reaction with H$_2$O$_2$ only.

Figure 21A:
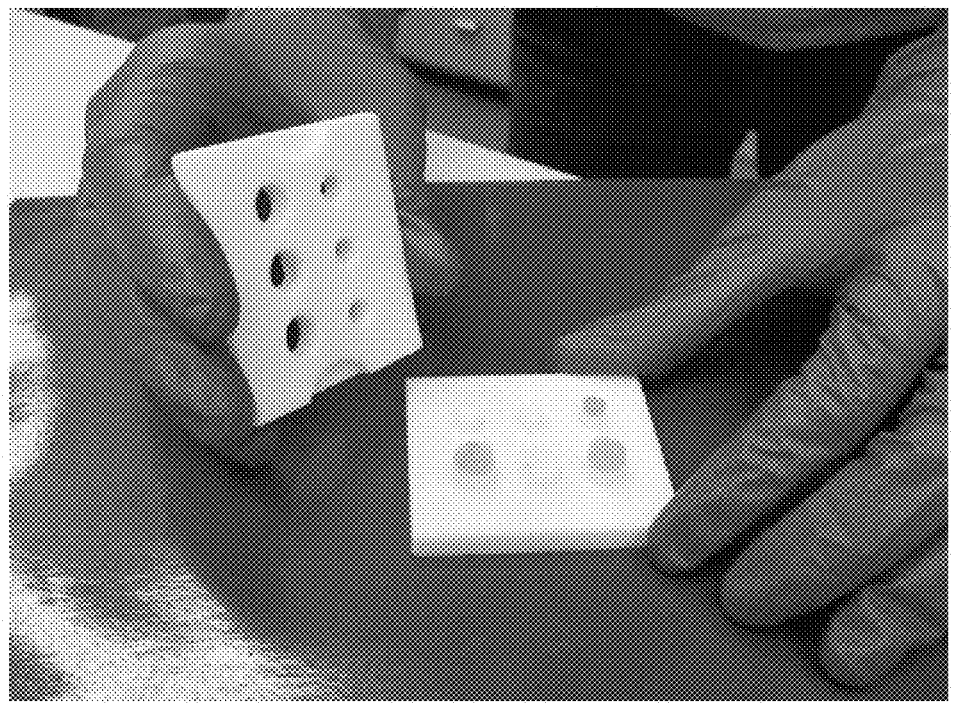
Figure 21B:
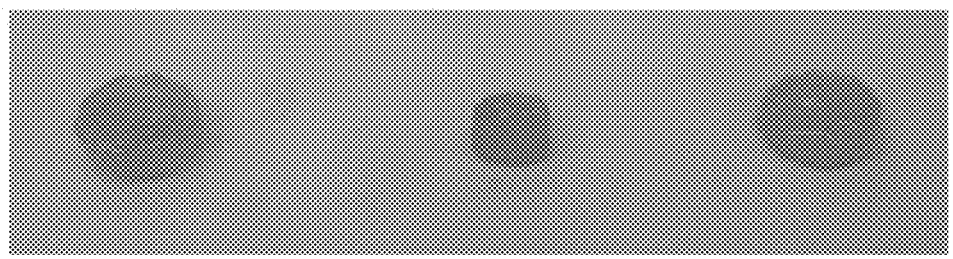

FIGS. 21A-B are photographs illustrating the generation of a composite of the present invention. FIG. 21A—Opening of the Teflon mold following photochemical crosslinking of the 6H-Res-ChBD-cellulose composites. FIG. 21B—left and middle are resulting composite polymers of 150 and 75 µl samples of 6H-Res-ChBD-cellulose whiskers, respectively, while the sample on the right is that received from the 150 µl sample of pure 6H-Res-ChBD polymer casted in the absence of cellulose whiskers.

Figure 22B:
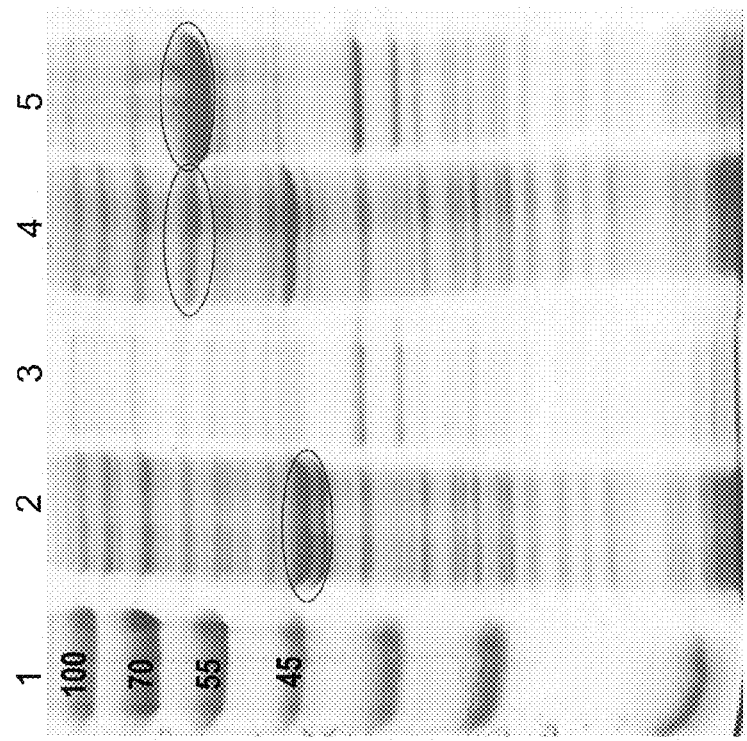
Figure 22A:
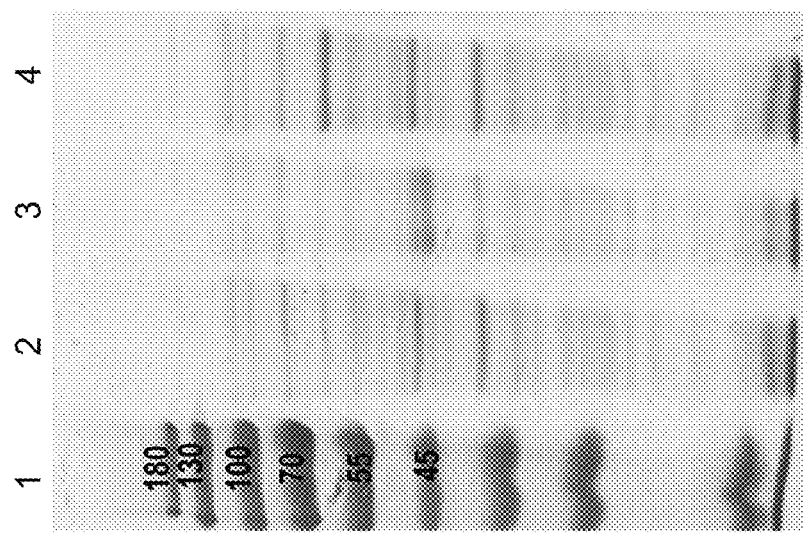

FIGS. 22A-B are scans illustrating SDS PAGE analyses of *E. Coli* proteins following overexpression of an exemplary spider silk of the present invention. FIG. 22A—Coomassie blue-stained SDS-PAGE analysis of total *E. coli* proteins. Proteins were stained with Coomassie blue. Lane 1—protein molecular weight marker, lane 2—control bacteria transformed with empty vector, lane 3—proteins collected from SpS (SEQ ID NO: 33)-expressing bacteria, lane 4—proteins of SpS-CBD-expressing bacteria (SEQ ID NO: 34). FIG. 22B—and Instant blue-stained SDS-PAGE analysis of soluble (S) and insoluble (IB) *E. coli* proteins. Proteins were stained with Coomassie blue. Lane 1—protein molecular weight marker, lanes 2-3—proteins of SpS (SEQ ID NO: 33)-expressing bacteria, S and IB, respectively. Lanes 4-5—proteins of SpS-CBD (SEQ ID NO: 34)-expressing bacteria, S and IB, respectively.

Figure 23A:
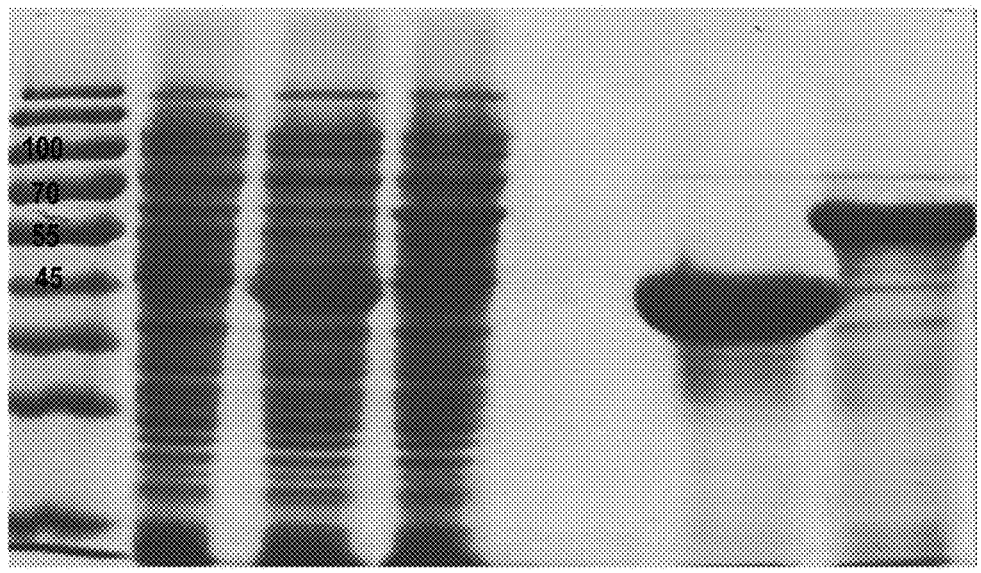
Figure 23B:
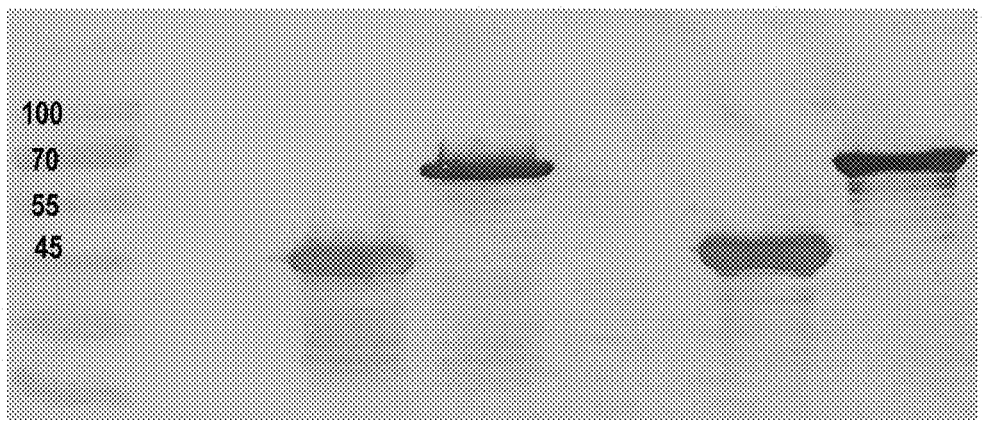

FIGS. 23A-B are scans illustrating SDS-PAGE analyses of FPLC-purified 6H-SpS (SEQ ID NO: 33) and 6H-SpS-CBD (SEQ ID NO: 34) expressed in *E. Coli*. FIG. 23A—SDS-PAGE analysis of FPLC fractions of Ni-NTA-purified SpS proteins. Lane 1—protein molecular weight marker, lanes 2-4—soluble proteins of empty vector-transformed *E. Coli* control lysates, SpS (SEQ ID NO: 33) and SpS-CBD (SEQ ID NO: 34) samples, respectively, prior to Ni-NTA purification. Lanes 4-7—purified protein fractions of control, SpS (SEQ ID NO: 33), SpS-CBD (SEQ ID NO: 34), respectively, following Ni-NTA purification. FIG. 23B—Western blot analysis of the same samples as described in FIG. 17A with anti-6His antibody.

Figure 24A:
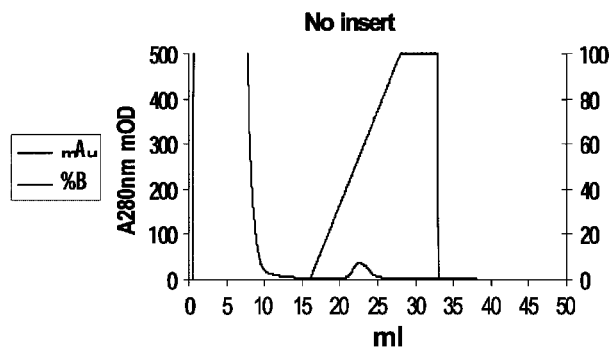
Figure 24B:
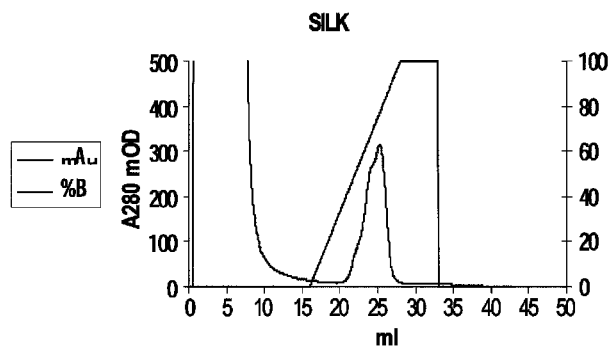
Figure 24C:
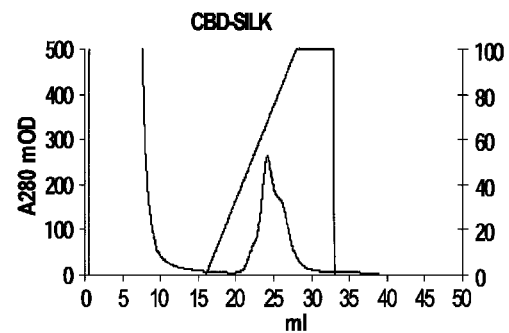

FIGS. 24A-C are graphs illustrating FPLC purification of 6H-SpS (SEQ ID NO: 33) and 6H-SpS-CBD (SEQ ID NO: 34). FIG. 24A—Chromatogram of the purification of control *E. coli* proteins on a Ni-NTA column. FIG. 24B—Chromatogram of the purification of 6H-SpS (SEQ ID NO: 33), on Ni-NTA column. FIG. 24C—Chromatogram of the purification of 6H-SpS-CBD (SEQ ID NO: 34), on a Ni-NTA column.

Figure 25:
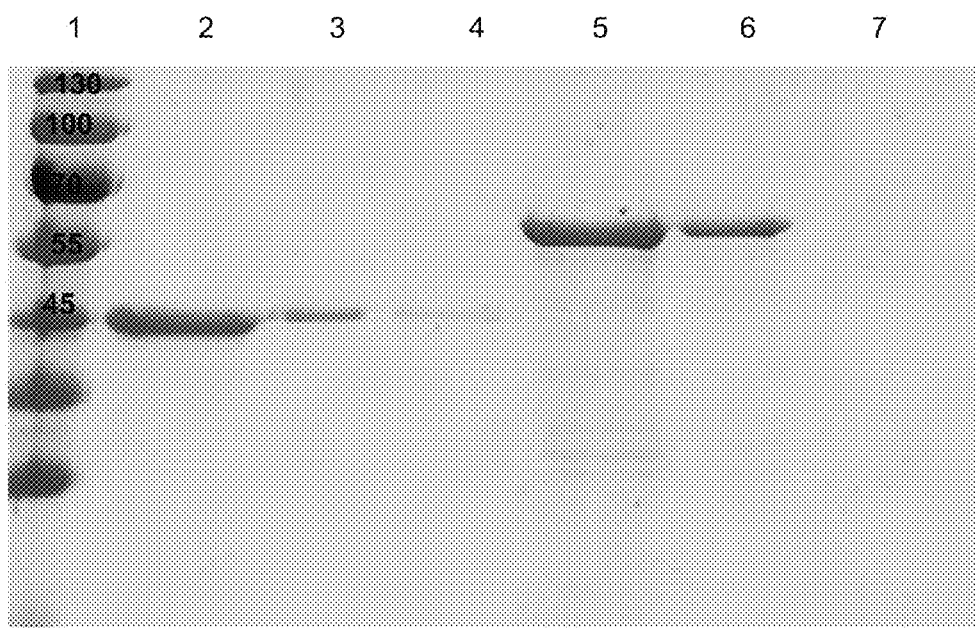

FIG. 25 is a scan of an SDS-PAGE analysis of a qualitative cellulose binding assay of affinity-purified SpS (SEQ ID NO: 33) and SpS-CBD (SEQ ID NO: 34). Lane 1—protein molecular weight marker, Lanes 2-4—spider silk cellulose binding assay: lane 2—SpS after Ni-NTA purification, lane 3—cellulose-bound protein, lane 4—unbound protein. The unbound protein is diluted 1:10 in comparison to protein concentration in lane 2. Lanes 5-7—SpS-CBD cellulose binding assay: lane 5-SpS-CBD after Ni-NTA purification, lane 6—cellulose-bound protein, lane 7—unbound protein. The unbound protein is diluted 1:10 in comparison to protein concentration in lane 5.

Figure 26:
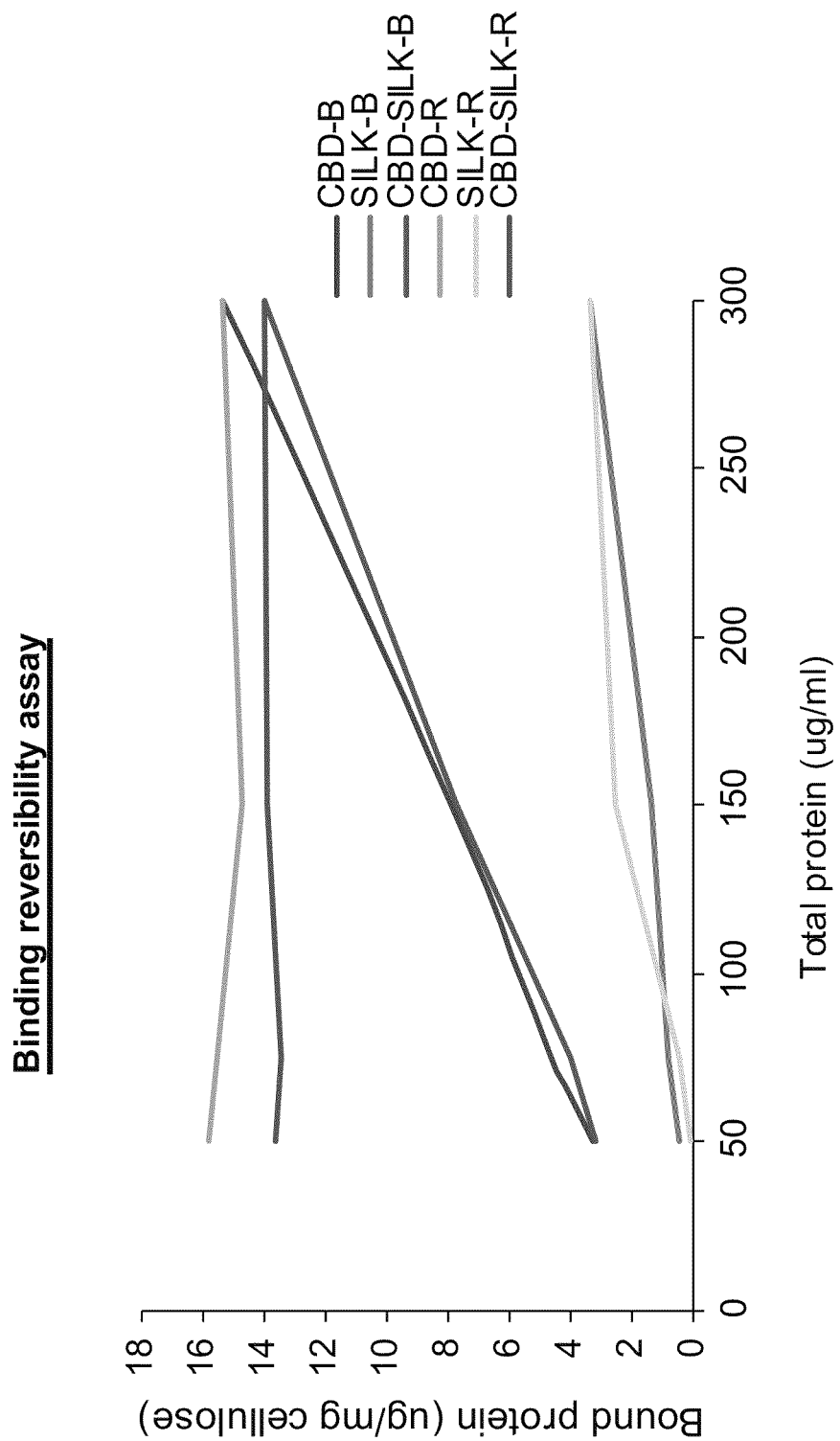

FIG. 26 is a graph of an adsorption/desorption isotherm. CBD*Clostridium cellulovorans* (CBDclos) (SEQ ID NO: 10), SpS (SEQ ID NO: 33) and SpS-CBD (SEQ ID NO: 34), at different concentrations, were allowed to adsorb to cellulose to the point of equilibrium (B). After equilibrium was reached, the highest protein concentration containing mixture was diluted to allow desorption (R).

Figure 27A:
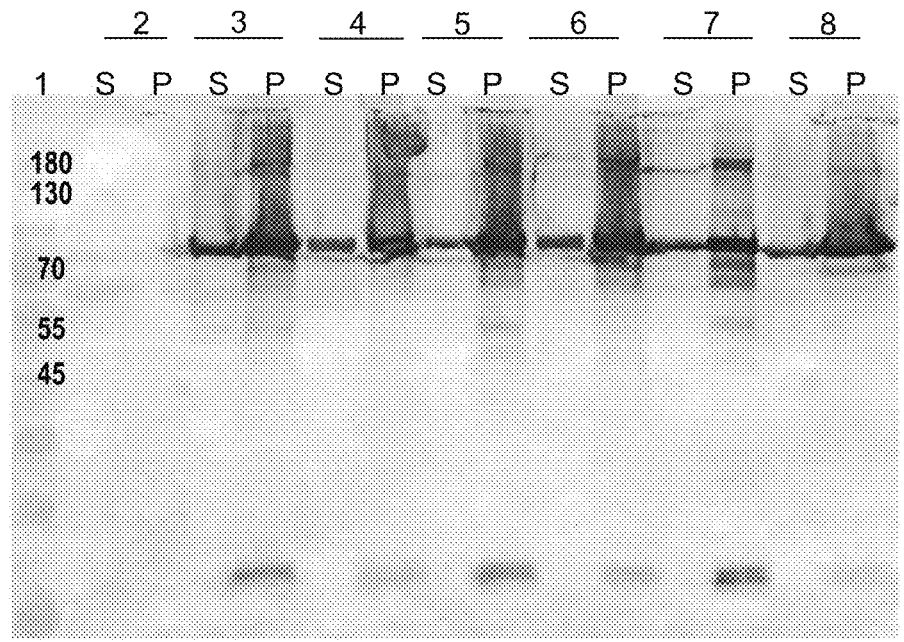
Figure 27B:
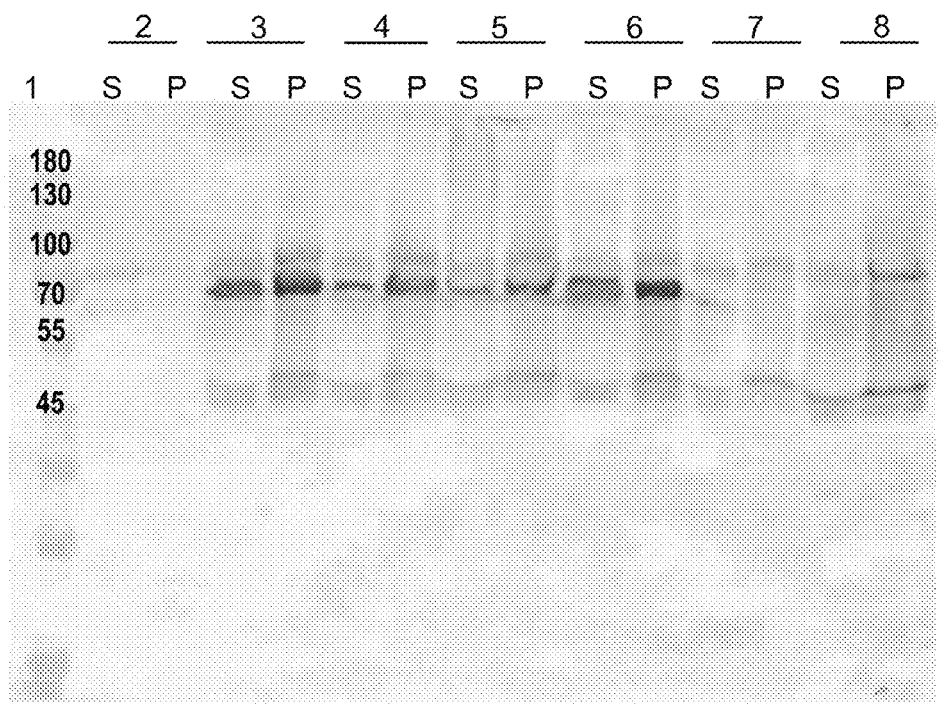

FIGS. 27A-B are scans of Western blot analyses of lysates of CBD-SpS12 (SEQ ID NO:35) and SpS6-CBD-SpS6 (SEQ ID NO:36)-expressing plants, using anti-CBD antibody for immunodetection. FIG. 27A—Tobacco plants expressing and accumulating CBD-SpS12 (SEQ ID NO:35) in the apoplast. Lane 1—protein molecular weight marker, lane 2—wild type tobacco plant lysates, Lanes 3-8—lysates of transgenic tobacco plant numbers 13.1-13.6, respectively. S-soluble proteins, P-insoluble proteins. FIG. 27B—Tobacco plants expressing SpS6-CBD-SpS6 (SEQ ID NO:36) in the cytoplasm. Lane 1—protein molecular weight marker, lane 2—wild type tobacco plant lysates, Lanes 3-8—Lysates of transgenic tobacco plant numbers 6.1-6.6, respectively. S-soluble proteins, P-insoluble proteins.

Figure 28A:
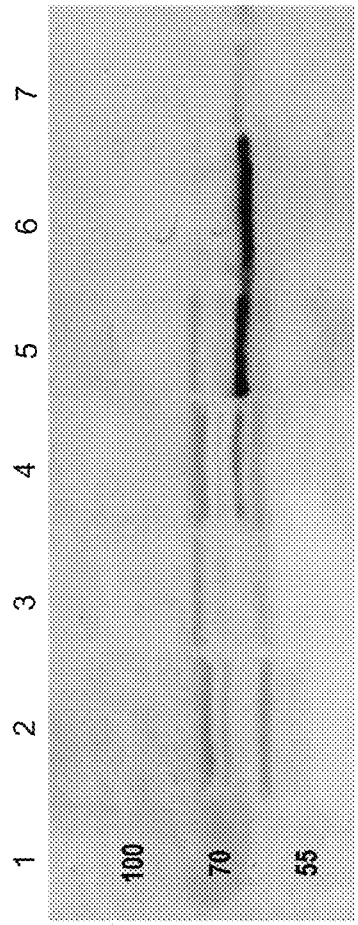
Figure 28B:
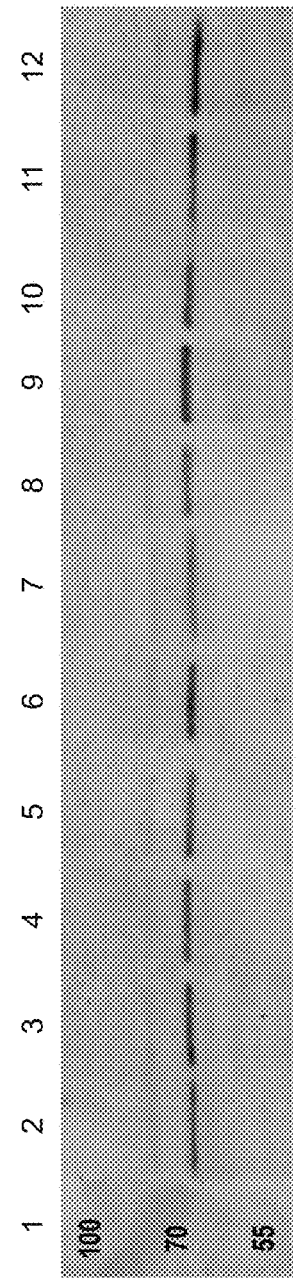

FIGS. 28A-B are scans of Western blot analyses of the SpS6-CBD-SpS6 (SEQ ID NO: 36) purification procedure, using anti-CBD antibody for immunodetection. FIG. 28A—Lane 1—protein molecular weight marker, lane 2—soluble proteins of wild type tobacco plant extracts, Lane 3—insoluble proteins of wild type tobacco, lane 4—soluble proteins of transgenic tobacco plant #6.4, lane 5—insoluble proteins of transgenic tobacco plant #6.4, lane 6—soluble proteins eluted from the insoluble fraction of #6.4 transgenic tobacco plant SpS6-CBD-SpS6 (SEQ ID NO: 36), lane 7—insoluble proteins eluted from the insoluble fraction of 6.4 transgenic tobacco plant SpS6-CBD-SpS6. FIG. 28B illustrates the heat stability and pH solubility of SpS6-CBD-SpS6 (SEQ ID NO: 36). Lane 1—protein molecular weight marker, lane 2—soluble proteins eluted from the insoluble fraction of the plant extract (as shown in FIG. 24A lane 6), lanes 3-6—heat stability assay at 60, 70, 80 and 90° C. respectively. Lanes 7-12—pH solubility test under pH=8, 7, 6, 5, 4, 3, respectively.

Figure 29:
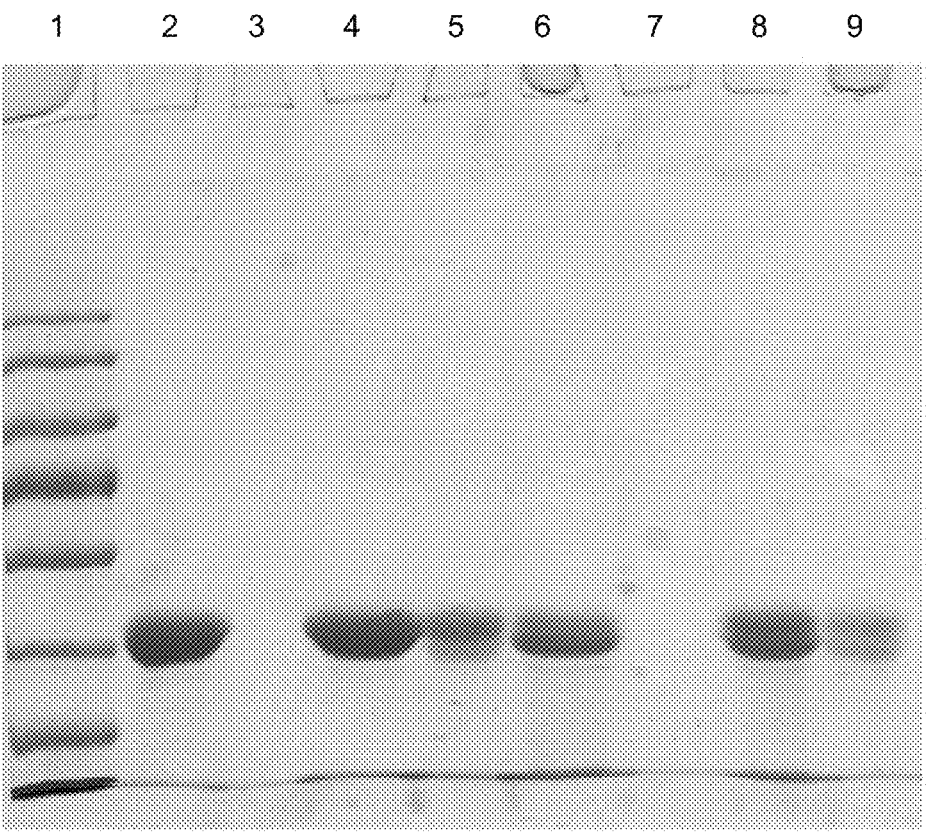

FIG. 29 is a Coomassie-stained SDS-PAGE analysis of metal-catalyzed polymerization of silk. Lane 1—protein molecular weight marker; lanes 2-5—reaction analysis of SpS (SEQ ID NO: 33) dialyzed against DDW: lane 2—protein solution without $H_2O_2$ or $CuCl_2$, lane 3—polymerization reaction including $H_2O_2$ and $CuCl_2$, lane 4—protein solution with addition of $H_2O_2$ only, lane 5—protein solution with the addition of $CuCl_2$ only. Lanes 6-9: reaction analysis of SpS dialyzed against 50 mM sodium phosphate (pH 7.5): lane 6—protein solution without $H_2O_2$ or $CuCl_2$, lane 7—polymerization reaction including $H_2O_2$ and $CuCl_2$, lane 8—protein solution with addition of $H_2O_2$ only, lane 9—protein solution with the addition of $CuCl_2$ only.

Figure 30:
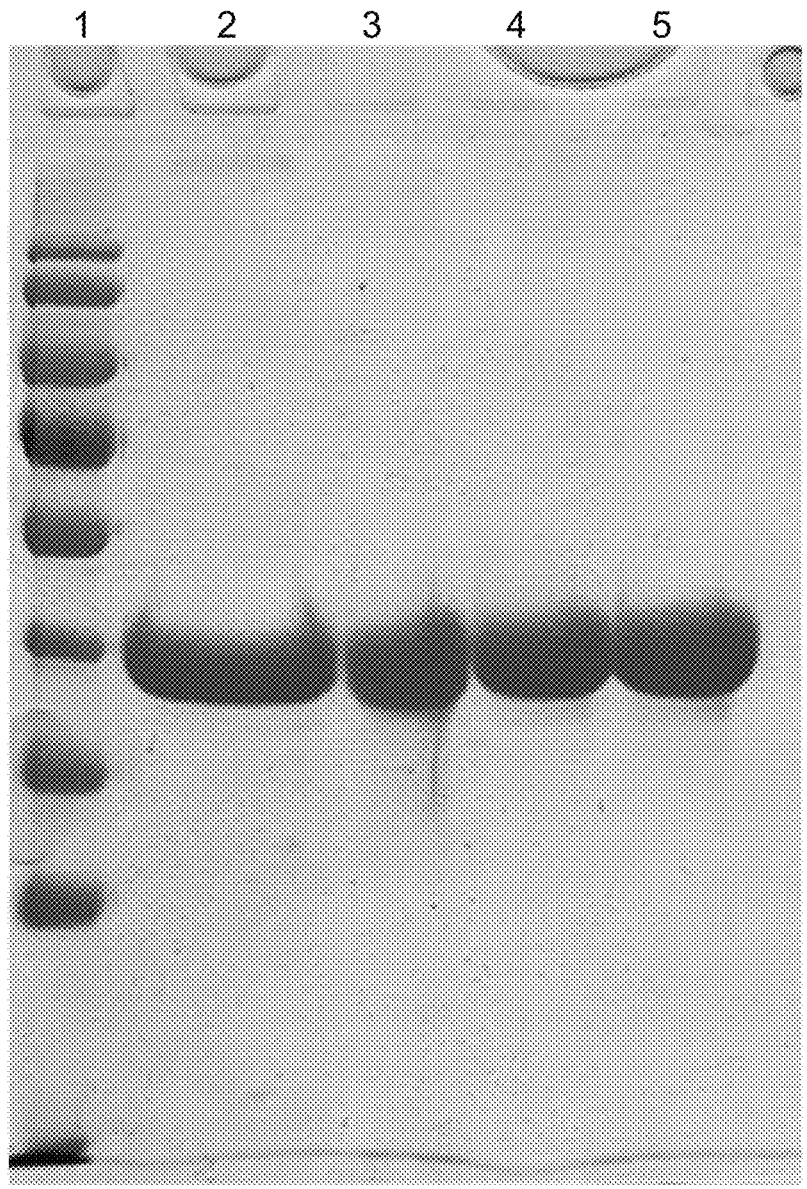

FIG. 30 is a Coomassie-stained SDS-PAGE analysis of SpS sponge preparation. Lane 1—protein molecular weight marker, lane 2—soluble protein before sponge preparation procedure, lane 3—soluble protein after dialysis against 50 mM sodium phosphate (pH 7.5), lane 4—soluble protein after dialysis against DDW, lane 5—soluble protein after concentration to ~50 mg/ml. The sample was diluted ×50 in order to confirm that there was no protein loss.

Figure 31A:
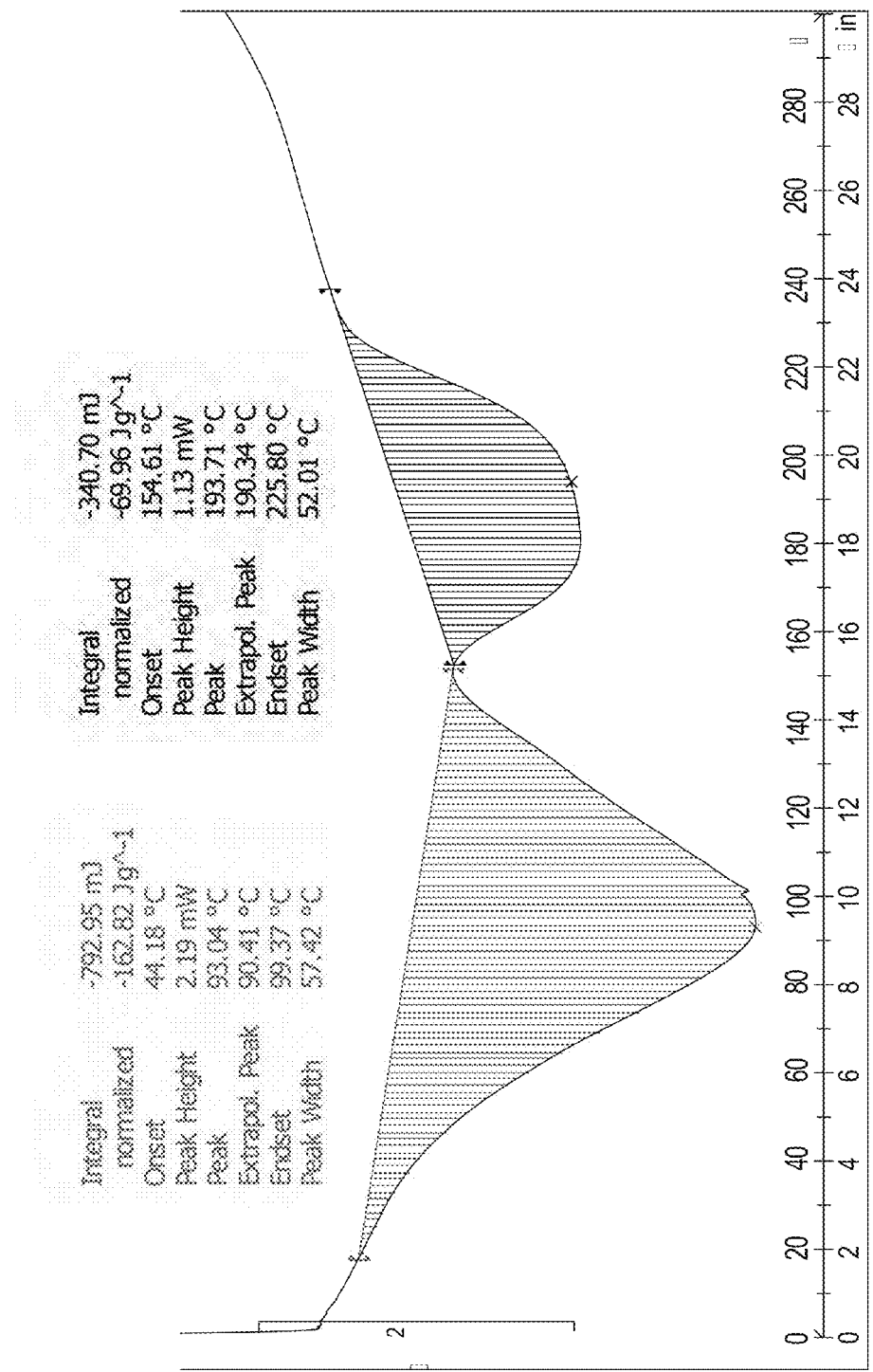
Figure 31B:
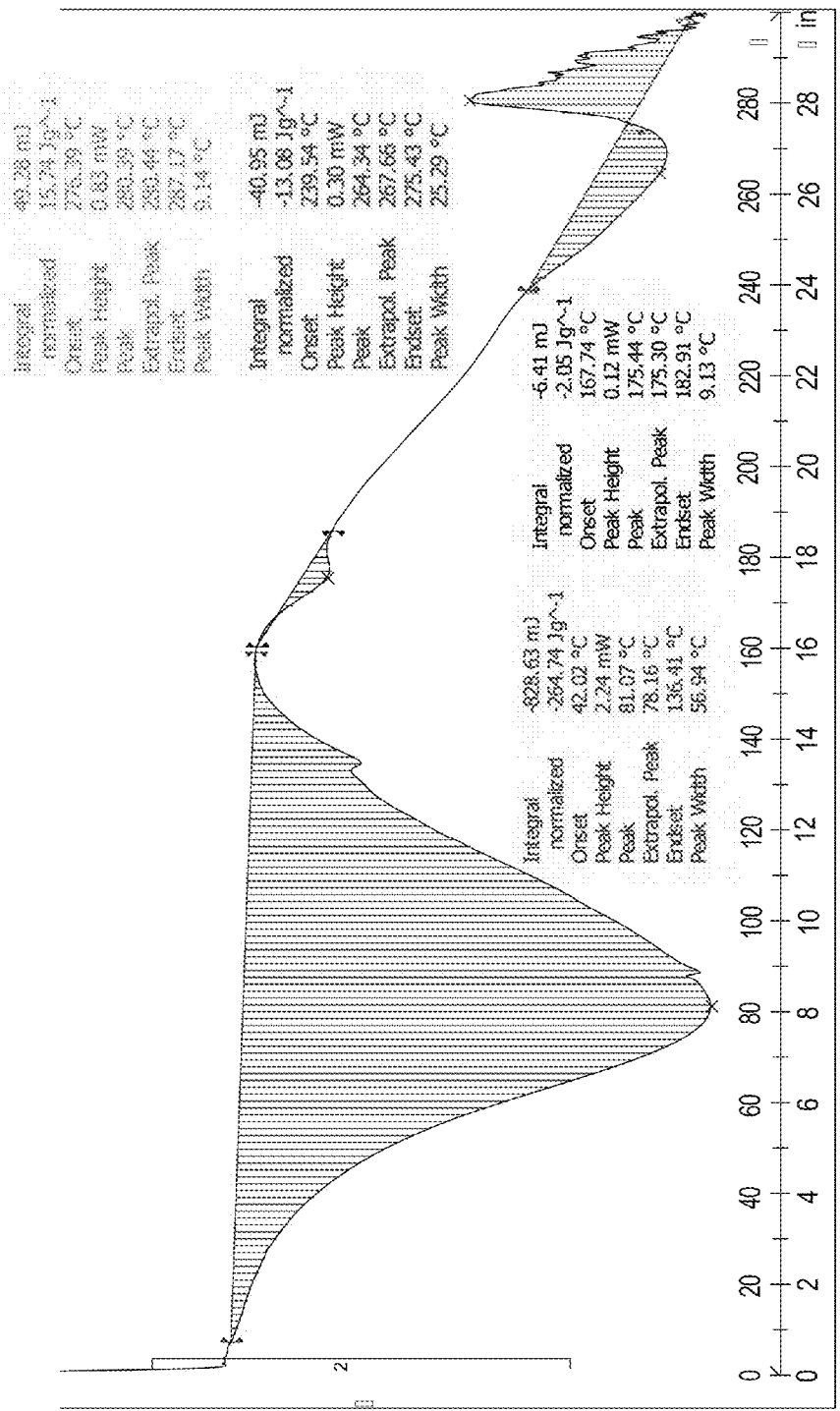
Figure 31C:
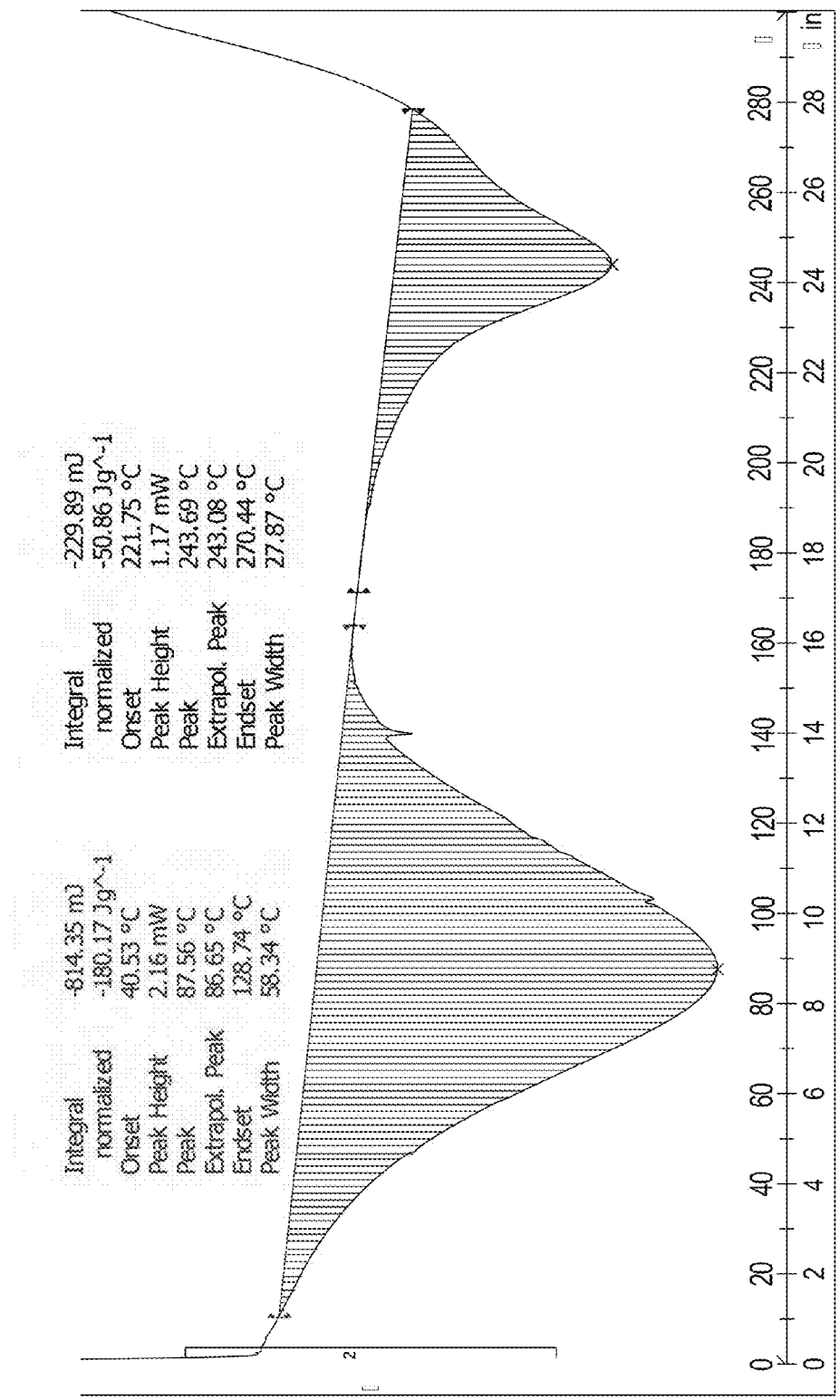

FIGS. 31A-C depict the results of DSC analysis of SpS-cellulose whisker sponges. A—DSC thermogram analysis of cellulose whiskers sponge; B—DSC thermogram analysis of SpS sponge; C—DSC thermogram analysis of 70% whiskers/30% SpS sponge.

DESCRIPTION OF EMBODIMENTS OF THE INVENTION

The present invention, in some embodiments thereof, relates to compositions comprising fibrous polypeptides and polysaccharides and uses of same. The fibrous polypeptides may comprise an endogenous polysaccharide binding domain or a heterologous polysaccharide binding domain.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search to identify novel composite biomaterials with superior mechanical properties for use in medical, industrial and other applications, the present inventors have generated novel fibrous polypeptides that enable directional binding and polymerization on polysaccharides.

Whilst reducing the present invention to practice, the present inventors generated and purified both resilin and spider-silk fusion proteins. Exemplary fusion proteins generated include resilin-chitin binding domain (Res-ChBD) (FIGS. 4-10, 18 and 19); resilin-cellulose binding domain (Res-CBD) (FIGS. 12-14, 16-17) and; spider-silk-cellulose binding domain (FIGS. 23-28).

Thus, according to one aspect of the present invention, there is provided an isolated polypeptide comprising an amino acid sequence encoding a monomer of a fibrous polypeptide attached to a heterologous polysaccharide binding domain.

As used herein, the phrase "fibrous polypeptide" refers to a polypeptide that consists of a plurality of monomer chains arranged in a matrix so as to form fibers or sheets. Fibrous proteins are described in D. Voet & J. G. Voet, "Biochemistry" (2d ed., John Wiley & Sons, New York, 1995, pp. 153-162), incorporated herein by this reference.

Examples of fibrous polypeptides include, but are not limited to, resilin, elastin, spider silk, silk-worm silk, collagen and mussel byssus protein.

As used herein, the term "resilin" refers to an elastic polypeptide, capable of forming a fiber, wherein each monomer thereof comprises at least two repeating units of the sequence as set forth in SEQ ID NO: 45. According to one embodiment, the repeating unit comprises a sequence as set forth in SEQ ID NO: 8. GenBank Accession Nos. of non-limiting examples of resilin are listed in Table 1 below. A resilin of the present invention also refers to homologs (e.g. polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to resilin sequences listed in Table 1 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 1 below lists examples of resilin NCBI sequence numbers.

TABLE 1

| Exemplary resilin NCBI sequence number | Organism |
|---|---|
| NP 995860 | *Drosophila melanogaster* |
| NP 611157 | *Drosophila melanogaster* |
| Q9V7U0 | *Drosophila melanogaster* |
| AAS64829 | *Drosophila melanogaster* |
| AAF57953 | *Drosophila melanogaster* |
| XP 001817028 | *Tribolium castaneum* |
| XP001947408 | *Acyrthosiphon pisum* |

According to one embodiment, the polypeptide sequence of resilin is set forth in SEQ ID NO: 9.

As used herein, the term "elastin" refers to an elastic polypeptide, capable of forming a fiber, wherein each monomer thereof comprises at least two repeating units of the sequence as set forth in SEQ ID NO: 46. GenBank Accession Nos. of non-limiting examples of elastin are listed in Table 2 below. An elastin of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to elastin sequences listed in Table 2 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 2 below lists examples of elastin NCBI sequence numbers.

TABLE 2

| Organism | Exemplary elastin NCBI sequence number |
|---|---|
| *Bos taurus* | NP786966 |
| mouse | NP 031951 |
| rat | NP 036854 |
| Human | AAC98395 |
| sheep | I47076 |

As used herein, the term "spider silk" refers to a polypeptide capable of forming a fiber which is comprised of spider silk, wherein each monomer thereof comprises at least two repeating units of the sequence set forth in SEQ ID NO: 26. According to one embodiment, the polypeptide chain comprises a spidroin 1 amino acid sequence. According to another embodiment, the polypeptide chain comprises a spidroin 2 amino acid sequence. According to one embodiment, the spider silk is dragline spider silk. GenBank Accession Nos. of non-limiting examples of spidroins 1 and 2 are listed in Table 3 below. A spider silk polypeptide of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to spider silk sequences listed in Table 3 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 3 below lists examples of spider silk NCBI sequence numbers.

TABLE 3

| Spider silk polypeptide | Exemplary spider silk NCBI sequence number |
|---|---|
| Spidroin 1 | P19837 |
| Spidroin 1 | AAC38957 |
| Spidroin 2 | ABR68858 |
| Spidroin 2 | AAT75317 |
| Spidroin 2 | P46804 |

According to one embodiment, the polypeptide sequence of the spider silk polypeptide is set forth in SEQ ID NO: 16 or SEQ ID NO: 38.

As used herein, the term "silkworm silk" refers to a silk polypeptide derived from silkworm, capable of forming a fiber. GenBank Accession Nos. of non-limiting examples of silkworm silk polypeptides are listed in Table 4 below. A silkworm silk polypeptide of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to silkworm silk sequences listed in Table 4 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 4 below lists examples of silkworm silk NCBI sequence numbers.

TABLE 4

| Exemplary silkworm silk NCBI sequence number |
|---|
| AAL83649 |
| AAA27839 |
| NP001106733 |
| NP001037488 |
| Caa35180 |

As used herein, the term "collagen" refers to an assembled collagen trimer, which in the case of type I collagen includes two alpha 1 chains and one alpha 2 chain. A collagen fiber is collagen which is devoid of terminal propeptides C and N. Contemplated collagens include types I, II, III, V, XI, and biologically active fragments therefrom. The collagen may be comprised of procollagen, atelocollagen or telocollagen. A collagen of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to collagen sequences listed in Table 1 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 5 below lists examples of collagen NCBI sequence numbers.

TABLE 5

| Exemplary human collagen NCBI sequence number |
|---|
| P02452 |
| P08123 |

As used herein, the phrase "mussel byssus protein" refers to the polypeptide found in the byssal threads of mussels comprising both collagen and elastin domains (e.g. Col-P or Col-D). A mussel byssus protein of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to mussel byssus sequences as set forth in NCBI sequence numbes AAB34042 and as determined using BlastP software of the National Center of Biotechnology Information (NCBI) using default parameters).

The homolog may also refer to a deletion, insertion, or substitution variant, including an amino acid substitution, thereof and biologically active polypeptide fragments thereof.

As mentioned, the isolated polypeptides of the present invention comprise a monomer of a fibrous polypeptide attached to a heterologous polysaccharide binding domain.

As used herein, the qualifier "heterologous" when relating to the heterologous polysaccharide binding domains of the fibrous polypeptides of the present invention indicates that the heterologous polysaccharide binding domain is not naturally found in that fibrous polypeptide to which it is fused.

The phrase "polysaccharide binding domain" refers to an amino acid sequence which binds a polysaccharide with a minimal dissociation constant ($K_d$) of about 10 μM [Tomme P, Boraston A, McLean B, Kormos J, Creagh A L, Sturch K, Gilkes N R, Haynes C A, Warren R A, Kilburn D G (1998) Characterization and affinity applications of cellulose-binding domains. J Chromatogr B Biomed Sci Appl. 715(1):283-96, Boraston A B, Bolam D N, Gilbert H J, Davies G J. (2004) Carbohydrate-binding modules: fine-tuning polysaccharide recognition. Biochem J. 382(Pt 3):769-81]. Typically, the polysaccharide binding domain comprises at least a functional portion of a polysaccharide binding domain of a polysaccharidase or a polysaccharide binding protein.

It will be appreciated that the fibrous polypeptide may be joined directly to the polysaccharide binding domain or may be joined via a linker. Amino acid sequences of exemplary linkers contemplated for the present invention are set forth in SEQ ID NOs: 52 and 53.

Exemplary polysaccharide binding domains include but are not limited to a chitin binding domain (examples of which are set forth in SEQ ID NO: 39 and 40), a starch binding domain (an example of which is set forth in SEQ ID NO: 41), a dextran binding domain (an example of which is set forth in SEQ ID NO: 42), a glucan binding domain, a chitosan binding domain (see for example Chen, H P; Xu, L L, (2005) J. of Integrative Plant Biology 47(4): 452-456), an alginate binding domain (an example of which is set forth in SEQ ID NO: 43) and an hyaluronic acid binding domain (an example of which is set forth in SEQ ID NO: 44).

According to this aspect of the present invention, when the fibrous polypeptide comprises resilin or spider silk, the polysaccharide binding domain may also be a cellulose binding domain.

Table 6 below lists exemplary sources of polysaccharide binding domains which are contemplated for use in the present invention.

TABLE 6

Sources of polysaccharide binding domains

| Binding Domain | Proteins Containing the Binding Domain |
|---|---|
| Cellulose Binding Domains[1] | β-glucanases (avicelases, CMCases, cellodextrinases) |
| | exoglucanses or cellobiohydrolases |
| | cellulose binding proteins |
| | xylanases |
| | mixed xylanases/glucanases |
| | esterases |
| | chitinases |
| | β-1,3-glucanases |
| | β-1,3-(β-1,4)-glucanases |
| | (β-)mannanases |
| | β-glucosidases/galactosidases |
| | cellulose synthases (unconfirmed) |
| Starch/Maltodextrin Binding Domains | α-amylases[2,3] |
| | β-amylases[4,5] |
| | pullulanases |
| | glucoamylases[6,7] |
| | cyclodextrin glucotransferases[8-10] (cyclomaltodextrin glucanotransferases) |
| | maltodextrin binding proteins[11] |
| Dextran Binding Domains | (Streptococcal) glycosyl transferases[12] |
| | dextran sucrases (unconfirmed) |
| | Clostridial toxins[13,14] |
| | glucoamylases[6] |
| | dextran binding proteins |
| β-Glucan Binding Domains | β-1,3-glucanases[15,16] |
| | β-1,3-(β-1,4)-glucanases (unconfirmed) |
| | β-1,3-glucan binding protein[17] |
| Chitin Binding Domains | chitinases |
| | chitobiases |
| | chitin binding proteins |
| | (see also cellulose binding domains) |
| | Heivein |

[1]Gilkes et al., Adv. Microbiol Reviews, (1991) 303-315.
[2]Søgaard et al., J. Biol. Chem. (1993) 268: 22480.
[3]Weselake et al., Cereal Chem. (1983) 60: 98.
[4]Svensson et al., J. (1989) 264: 309.
[5]Jespersen et al., J. (1991) 280: 51.
[6]Belshaw et al., Eur. J. Biochem. (1993) 211: 717.
[7]Sigurskjold et al., Eur. J. Biochem. (1994) 225: 133.
[8]Villette et al., Biotechnol. Appl. Biochem. (1992) 16: 57.
[9]Fukada et al., Biosci. Biotechnol. Biochem. (1992) 56: 556.
[10]Lawson et al., J. Mol. Biol. (1994) 236: 590.
[14]von Eichel-Streiber et al., Mol. Gen. Genet. (1992) 233: 260.
[15]Klebl et al., J. Bacteriol. (1989) 171: 6259.
[16]Watanabe et al., J. Bacteriol. (1992) 174: 186.
[17]Duvic et al., J. Biol. Chem. (1990): 9327.

Table 7 below lists an overview of enzymes with chitin binding domains which are contemplated for use as the polysaccharide domains of the present invention.

TABLE 7

| Source (strain) | Enzyme | Accession No. | Ref.[1] |
|---|---|---|---|
| Bacterial enzymes | | | |
| Type I | | | |
| Aeromonas sp. (No10S-24) | Chi | D31818 | 1 |
| Bacillus circulans (WL-12) | ChiA1 | P20533/M57601/A38368 | 2 |
| Bacillus circulans (WL-12) | ChiD | P27050/D10594 | 3 |
| Janthinobacterium lividum | Chi69 | U07025 | 4 |
| Streptomyces griseus | Protease C | A53669 | 5 |
| Type II | | | |
| Aeromonas cavia (K1) | Chi | U09139 | 6 |
| Alteromonas sp (0-7) | Chi85 | A40633/P32823/D13762 | 7 |
| Autographa californica (C6) | NPH-128[a] | P41684/L22858 | 8 |
| Serratia marcescens | ChiA | A25090/X03657/L01455/P07254 | 9 |
| Type III | | | |
| Rhizopus oligosporus (IFO8631) | Chi1 | P29026/A47022/D10157/S27418 | 10 |
| Rhizopus oligosporus (IFO8631) | Chi2 | P29027/B47022/D10158/S27419 | 10 |
| Saccharomyces cerevisiae | Chi | S50371/U17243 | 11 |
| Saccharomyces cerevisiae (DBY939) | Chi1 | P29028/M74069 | 12 |
| Saccharomyces cerevisiae (DBY918) | Chi2 | P29029/M7407/B41035 | 12 |
| Plant enzymes | | | |
| Hevein superfamily | | | |
| Allium sativum | Chi | M94105 | 13 |
| Amaranthus caudatus | AMP-1[b] | P27275/A40240 | 14, 15 |
| Amaranthus caudatus | AMP-2[b] | S37381/A40240 | 14, 15 |
| Arabidopsis thaliana (cv. colombia) | ChiB | P19171/M38240/B45511 | 16 |
| Arabidopsis thaliana | PHP[c] | U01880 | 17 |
| Brassica napus | Chi | U21848 | 18 |
| Brassica napus | Chi2 | Q09023/M95835 | 19 |
| Hevea brasiliensis | Hev1[d] | P02877/M36986/A03770/A38288 | 20, 21 |
| Hordeum vulgare | Chi33 | L34211 | 22 |
| Lycopersicon esculentum | Chi9 | Q05538/Z15140/S37344 | 23 |
| Nicotiana tabacum | CBP20[e] | S72424 | 24 |
| Nicotiana tabacum | Chi | A21091 | 25 |
| Nicotiana tabacum (cv. Havana) | Chi | A29074/M15173/S20981/S19855 | 26 |
| Nicotiana tabacum (FB7-1) | Chi | JQ0993/S0828 | 27 |
| Nicotiana tabacum (cv. Samsun) | Chi | A16119 | 28 |
| Nicotiana tabacum (cv. Havana) | Chi | P08252/X16939/S08627 | 27 |
| Nicotiana tabacum (cv. BY4) | Chi | P24091/X51599/X64519//S13322 | 26, 27, 29 |
| Nicotiana tabacum (cv. Havana) | Chi | P29059/X64518/S20982 | 26 |
| Oryza sativum (IR36) | ChiA | L37289 | 30 |
| Oryza sativum | ChiB | JC2253/S42829/Z29962 | 31 |
| Oryza sativum | Chi | S39979/S40414/X56787 | 32 |
| Oryza sativum (cv. Japonicum) | Chi | X56063 | 33 |
| Oryza sativum (cv. Japonicum) | Chi1 | P24626/X54367/S14948 | 34 |
| Oryza sativum | Chi2 | P25765/S15997 | 35 |
| Oryza sativum (cv. Japonicum) | Chi3 | D16223 | |
| Oryza sativum | ChiA | JC2252/S42828 | 30 |
| Oryza sativum | Chi1 | D16221 | 32 |
| Oryza sativum (IR58) | Chi | U02286 | 36 |
| Oryza sativum | Chi | X87109 | 37 |

TABLE 7-continued

| Source (strain) | Enzyme | Accession No. | Ref.[1] |
|---|---|---|---|
| *Pisum sativum* (cv. Birte) | Chi | P36907/X63899 | 38 |
| *Pisum sativum* (cv. Alcan) | Chi2 | L37876 | 39 |
| *Populus trichocarpa* | Chi | S18750/S18751/X59995/P29032 | 40 |
| *Populus trichocarpa* (H11-11) | Chi | U01660 | 41 |
| *Phaseolus vulgaris* (cv. Saxa) | Chi | A24215/S43926/Jq0965/P36361 | 42 |
| *Phaseolus vulgaris* (cv. Saxa) | Chi | P06215/M13968/M19052/A25898 | 43, 44, 45 |
| *Sambucus nigra* | PR-3[f] | Z46948 | 46 |
| *Secale cereale* | Chi | JC2071 | 47 |
| *Solanum tuberosum* | ChiB1 | U02605 | 48 |
| *Solanum tuberosum* | ChiB2 | U02606 | 48 |
| *Solanum tuberosum* | ChiB3 | U02607/S43317 | 48 |
| *Solanum tuberosum* | ChiB4 | U02608 | 48 |
| *Solanum tuberosum* (cv. Maris Piper) | WIN-1[g] | P09761/X13497/S04926 | 49 |
| *Solanum tuberosum* (cv. Maris Piper) | WIN-2[g] | P09762/X13497/S04927 | 49 |
| *Triticum aestivum* | Chi | S38670/X76041 | 50 |
| *Triticum aestivum* | WGA-1[h] | P10968/M25536/S09623/S07289 | 51, 52 |
| *Triticum aestivum* | WGA-2[h] | P02876/M25537/S09624 | 51, 53 |
| *Triticum aestivum* | WGA-3[h] | P10969/J02961/S10045/A28401 | 54 |
| *Ulmus americana* (NPS3-487) | Chi | L22032 | 55 |
| *Urtica dioica* | AGL[i] | M87302 | 56 |
| *Vigna unguiculata* (cv. Red caloona) | Chi1 | X88800 | 57 |

[a]NHP: nuclear polyhedrosis virus endochitinase like sequence;
Chi: chitinase,
[b]anti-microbial peptide,
[c]pre-hevein like protein,
[d]hevein,
[e]chitin-binding protein,
[f]pathogenesis related protein,
[g]wound-induced protein,
[h]wheat germ agglutinin,
[i]agglutinin (lectin).
[1]References:
1 Udea et al. (1994) *J. Ferment. Bioeng.* 78, 205-211
2 Watanabe et al. (1990) *J. Biol. Chem.* 265, 15659-16565
3 Watanabe et al. (1992) *J. Bacteriol.* 174, 408-414
4 Gleave et al. (1994) *EMBL Data Library*
5 Sidhu et al. (1994) *J. Biol. Chem.* 269, 20167-20171
6 Jones et al. (1986) *EMBO J.* 5, 467-473
7 Sitrit et al. (1994) *EMBL Data Library*
8 Genbank entry only
9 Tsujibo et al. (1993) *J. Bacteriol.* 175, 176-181
10 Yanai et al. (1992) *J. Bacteriol.* 174, 7398-7406
11 Pauley (1994) *EMBL Data Library*
12 Kuranda et al. (1991) *J. Biol. Chem.* 266, 19758-19767
13 van Damme et al. (1992) *EMBL Data Library*
14 Broekaert et al. (1992) *Biochemistry* 31, 4308-4314
15 de Bolle et al. (1993) *Plant Mol. Physiol.* 22, 1187-1190
16 Samac et al. (1990) *Plant Physiol.* 93, 907-914
17 Potter et al. (1993) *Mol. Plant Microbe Interact.* 6, 680-685
18 Buchanan-Wollaston (1995) *EMBL Data Library*
19 Hamel et al. (1993) *Plant Physiol.* 101, 1403-1403
20 Broekaert et al. (1990) *Proc. Natl. Acad. Sci. USA* 87, 7633-7637
21 Lee et al. (1991) *J. Biol. Chem.* 266, 15944-15948
22 Leah et al. (1994) *Plant Physiol.* 6, 579-589
23 Danhash et al. (1993) *Plant Mol. Biol.* 22 1017-1029
24 Ponstein et al. (1994) *Plant Physiol.* 104, 109-118
25 Meins et al. (1991) Patent EP0418695-A1
26 van Buuren et al. (1992) *Mol. Gen. Genet.* 232, 460-469
27 Shinshi et al. (1990) *Plant Mol. Biol.* 14, 357-368
28 Cornelissen et al. (1991) Patent EP0440304-A2
29 Fukuda et al. (1991) *Plant Mol. Biol.* 16, 1-10
30 Yun et al. (1994) *EMBL Data Library*
31 Kim et al. (1994) *Biosci. Biotechnol. Biochem.* 58, 1164-1166
32 Nishizawa et al. (1993) *Mol. Gen. Genet.* 241, 1-10
33 Nishizawa et al. (1991) *Plant Sci* 76, 211-218
34 Huang et al. (1991) *Plant Mol. Biol.* 16, 479-480
35 Zhu et al. (1991) *Mol. Gen. Genet.* 226, 289-296
36 Muthukrishhnan et al. (1993) *EMBL Data Library*
37 Xu (1995) *EMBL Data Library*
38 Vad et al. (1993) *Plant Sci* 92, 69-79
39 Chang et al. (1994) *EMBL Data Library*
40 Davis et al. (1991) *Plant Mol. Biol.* 17, 631-639
41 Clarke et al. (1994) *Plant Mol. Biol.* 25, 799-815
42 Broglie et al. (1989) *Plant Cell* 1, 599-607
43 Broglie et al. (1986) *Proc. Natl. acad. Sci. USA* 83, 6820-6824
44 Lucas et al. (1985) *FEBS Lett.* 193, 208-210
45 Hedrick et al. (1988) *Plant Physiol.* 86, 182-186
46 Roberts et al. (1994) *EMBL Data LibraryI*
47 Vamagami et al. (1994) *Biosci. Biotechnol. Biochem.* 58, 322-329
48 Beerhues et al. (1994) *Plant Mol. Biol.* 24, 353-367
49 Stanford et al. (1989) *Mol. Gen. Genet.* 215, 200-208
50 Liao et al. (1993) *EMBL Data Library*
51 Smith et al. (1989) *Plant Mol. Biol.* 13, 601-603
52 Wright et al. (1989) *J. Mol. Evol.* 28, 327-336
53 Wright et al. (1984) *Biochemistry* 23, 280-287
54 Raikhel et al. (1987) *Proc. Natl. acad. Sci. USA* 84, 6745-6749
55 Hajela et al. (1993) *EMBL Data Library*
56 Lerner et al. (1992) *J. Biol. Chem.* 267, 11085-11091
57 Vo et al. (1995) *EMBL Data Library*

Table 8 herein below provides an overview of proteins containing Streptocooai glucan-binding repeats (Cpl superfamily) which may be used as polysaccharide domains of the present invention.

TABLE 8

Overview of proteins containing Streptococcal glucan-binding repeats (Cpl superfamily)

| Source | Protein | Accession No. | Ref.[2] |
|---|---|---|---|
| *S. downei* (*sobrinus*) (0MZ176) | GTF-I | D13858 | 1 |
| *S. downei* (*sobrinus*) (MFe28) | GTF-I | P11001/M17391 | 2 |
| *S. downei* (*sobrinus*) (MFe28) | GTF-S | P29336/M30943/A41483 | 3 |
| *S. downei* (*sobrinus*) (6715) | GTF-I | P27470/D90216/A38175 | 4 |
| *S. downei* (*sobrinus*) | DEI | L34406 | 5 |
| *S. mutants* (Ingbritt) | GBP | M30945/A37184 | 6 |
| *S. mutants* (GS-5) | GTF-B | A33128 | 7 |
| *S. mutants* (GS-5) | GTF-B | P08987/M17361/B33135 | 8 |
| *S. mutants* | GTF-B[3'-ORF] | P05427/C33135 | 8 |
| *S. mutants* (GS-5) | GTF-C | P13470/M17361/M22054 | 9 |
| *S. mutants* (GS-5) | GTF-C | not available | 10 |
| *S. mutants* (GS-5) | GTF-D | M29296/A45866 | 11 |
| *S. salivarius* | GTF-J | A44811/S22726/S28809 Z11873/M64111 | 12 |
| *S. salivarius* | GTF-K | S22737/S22727/Z11872 | 13 |
| *S. salivarius* (ATCC25975) | GTF-L | L35495 | 14 |
| *S. salivarius* (ATCC25975) | GTF-M | L35928 | 14 |
| *S. pneumoniae* R6 | LytA | P06653/A25634/M13812 | 15 |
| *S. pneumoniae* | PspA | A41971/M74122 | 16 |
| Phage HB-3 | HBL | P32762/M34652 | 17 |
| Phage Cp-1 | CPL-1 | P15057/J03586/A31086 | 18 |
| Phage Cp-9 | CPL-9 | P19386/M34780/JQ0438 | 19 |
| Phage EJ-1 | EJL | A42936 | 20 |
| *C. difficile* (VPI 10463) | ToxA | P16154/A37052/M30307 X51797/S08638 | 21 |
| *C. difficile* (BARTS W1) | ToxA | A60991/X17194 | 22 |
| *C. difficile* (VPI 10463) | ToxB | P18177/X53138/X60984 S10317 | 23, 24 |
| *C. difficile* (1470) | ToxB | S44271/Z23277 | 25, 26 |
| *C. novyi* | a-toxin | S44272/Z23280 | 27 |
| *C. novyi* | a-toxin | Z48636 | 28 |
| *C. acetobutylicum* (NCIB8052) | CspA | S49255/Z37723 | 29 |

TABLE 8-continued

Overview of proteins containing Streptococcal glucan-binding repeats (Cpl superfamily)

| Source | Protein | Accession No. | Ref.[2] |
|---|---|---|---|
| C. acetobutylicum (NCIB8052) | CspB | Z50008 | 30 |
| C. acetobutylicum (NCIB8052) | CspC | Z50033 | 30 |
| C. acetobutylicum (NCIB8052) | CspD | Z50009 | 30 |

[2]References:
1 Sato et al. (1993) *DNA sequence* 4, 19-27
2 Ferreti et al. (1987) *J. Bacteriol.* 169, 4271-4278
3 Gilmore et al. (1990) *J. Infect. Immun.* 58, 2452-2458
4 Abo et al. (1991) *J. Bacteriol.* 173, 989-996
5 Sun et al. (1994) *J. Bacteriol.* 176, 7213-7222
6 Banas et al. (1990) *J. Infect. Immun.* 58, 667-673
7 Shiroza et al. (1990) *Protein Sequence Database*
8 Shiroza et al. (1987) *J. Bacteriol.* 169, 4263-4270
9 Ueda et al. (1988) *Gene* 69, 101-109
10 Russel (1990) *Arch. Oral. Biol.* 35, 53-58
11 Honda et al. (1990) *J. Gen. Microbiol.* 136, 2099-2105
12 Giffard et al. (1991) *J. Gen. Microbiol.* 137, 2577-2593
13 Jacques (1992) *EMBL Data Library*
14 Simpson et al. (1995) *J. Infect. Immun.* 63, 609-621
15 Gargia et al. (1986) *Gene* 43, 265-272
16 Yother et al. (1992) *J. Bacteriol.* 174, 601-609
17 Romero et al. (1990) *J. Bacteriol.* 172, 5064-5070
18 Garcia et al. (1988) *Proc. Natl. Acad. Sci, USA* 85, 914-918
19 Garcia et al. (1990) *Gene* 86, 81-88
20 Diaz et al. (1992) *J. Bacteriol.* 174, 5516-5525
21 Dove et al. (1990) *J. Infect. Immun.* 58, 480-488
22 Wren et al. (1990) *FEMS Microbiol. Lett.* 70, 1-6
23 Barroso et a. (1990) *Nucleic Acids Res.* 18, 4004-4004
24 von Eichel-Streiber et al. (1992) *Mol. Gen. Genet.* 233, 260-268
25 Sartinger et al. (1993) *EMBL Data Library*
26 von Eichel-Streiber et al. (1995) *Mol. Microbiol.* In Press
27 Hofmann et al. (1993) *EMBL Data Library*
28 Hofmann et al. (1995) *Mol. Gen. Genet.* In Press
29 Sanchez et al. (1994) *EMBL Data Library*
30 Sanchez et al. (1995) *EMBL Data Library*

Table 9 below lists proteins containing putative β-1,3 glucan-binding domains which may be contemplated as the polysaccharide binding domains of the present invention.

TABLE 9

Overview of proteins containing putative

| Source (strain) | Protein | accession No. | Ref[3] |
|---|---|---|---|
| Type I | | | |
| B. circulans (WL-12) | GLCA1 | P23903/M34503/JQ0420 | 1 |
| B. circulans (IAM 1165) | BglH | JN0772/D17519/S67033 | 2 |
| Type II | | | |
| Actinomadura sp. (FC7) | XynII | U08894 | 3 |
| Arthrobacter sp. (YCWD3) | GLCI | D23668 | 9 |
| O. xanthineolytica | GLC | P22222/M60826/A39094 | 4 |
| R. faecitabidus (YLM-50) | RP I | Q05308/A45053/D10753 | 5a, b |
| R. communis | Ricin | A12892 | 6 |
| S. lividans (1326) | XlnA | P26514/M64551/JS07986 | 7 |
| T. tridentatus | FactorGa | D16622 | 8 |

B.: Bacillus,
O.: Oerskovia,
R. faecitabidus: Rarobacter faecitabidus,
R. communis: Ricinus communis,
S.: Streptomyces,
T.: Tachypleus (Horseshoe Crab)
[3]References:
1 Yahata et al. (1990) *Gene* 86, 113-117
2 Yamamoto et al. (1993) *Biosci. Biotechnol. Biochem.* 57, 1518-1525
3 Harpin et al. (1994) *EMBL Data Library*

TABLE 9-continued

Overview of proteins containing putative

| Source (strain) | Protein | accession No. | Ref[3] |
|---|---|---|---|

4 Shen et al. (1991) *J. Biol. Chem.* 266, 1058-1063
5a Shimoi et al. (1992) *J. Biol. Chem.* 267, 25189-25195
5b Shimoi et al. (1992) *J. Biochem* 110, 608-613
6 Horn et al. (1989) Patent A12892
7 Shareck et al. (1991) *Gene* 107, 75-82
8 Seki et al. (1994) *J. Biol. Chem.* 269, 1370-1374
9 Watanabe et al. (1993) *EMBL Data Library*

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to N' terminus modification, C' terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modifications. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C (R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acids such as Phenylglycine, 1,2,3,4-tetrahydroisoquinoline-3-carboxylic acid (TIC), naphthylelanine (Nol), ring-methylated derivatives of Phe, halogenated derivatives of Phe or o-methyl-Tyr.

As mentioned, the amino acid sequences of polypeptides of fibrous proteins may either be the amino acid sequences of the polypeptides in naturally-occurring fibrous proteins or those that comprise either conservative or non-conservative substitutions.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered conservative substitutions.

For producing conservative substitutions by non-naturally occurring amino acids it is also possible to use amino acid analogs (synthetic amino acids) well known in the art. A peptidomimetic of the naturally occurring amino acids is well documented in the literature known to the skilled practitioner.

When effecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall within the scope of the present invention are those which still constitute a polypeptide being able to form a fibrous protein.

As used herein in the specification and in the claims section below, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 10 and 11 below list naturally occurring amino acids (Table 10) and non-conventional or modified amino acids (Table 11) which can be used with the present invention.

TABLE 10

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 11

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclo-hexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |

TABLE 11-continued

| Non-conventional amino acid | Code | Non-conventional amino acid | Code |
|---|---|---|---|
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclo-hexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-ethylhistidine | Mhis | L-α-methylhomophenylalanine | Mhphe |
| L-α-thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-ethylvaline | Mtrp | L-α-methyltyrosine | Mtyr |
| L-α-methylleucine | Mval nbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenylnyl-amino)cyclopropane | Nmbc | | |

Amino acid sequences of exemplary polypeptides of the present invention are set forth in SEQ ID NOs: 11-13, 55, 57, 58 and SEQ ID NOs. 32-36.

Recombinant techniques are preferably used to generate the polypeptides of the present invention since these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

An example of an isolated polynucleotide which can be used to express resilin is as set forth in SEQ ID NO: 15. Examples of isolated polynucleotide sequences which can be used to express spider silk are as set forth in SEQ ID NOs: 23 and 27. An example of an isolated polynucleotide which can be used to express a cellulose binding domain is set forth in SEQ ID NO: 25. Exemplary polynucleotide sequences which can be used to express the polypeptides of the present invention are set forth in SEQ ID NO: 17-22, 24, 28 and 29.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein, the phrase "complementary polynucleotide sequence" refers to a sequence which results from reverse transcription of messenger RNA using a reverse transcriptase or any other RNA-dependent DNA polymerase. Such a sequence can be subsequently amplified in vivo or in vitro using a DNA-dependent DNA polymerase.

As used herein, the phrase "genomic polynucleotide sequence" refers to a sequence derived (isolated) from a chromosome and thus represents a contiguous portion of a chromosome.

As used herein, the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis-acting expression regulatory elements.

The polynucleotides of the present invention may further comprise a signal sequence encoding a signal peptide for the secretion of the fibrous polypeptide. An exemplary signal sequence that may be used in the constructs of the present invention (for plant transfection) is a vacuolar signal sequence.

Following expression and secretion, the signal peptides are typically removed from the precursor proteins resulting in the mature proteins.

Polynucleotides of the present invention may be prepared using PCR techniques as described in Example 1 and Example 7 herein below, or any other method or procedure known in the art for ligation of two different DNA sequences. See, for example, "Current Protocols in Molecular Biology", eds. Ausubel et al., John Wiley & Sons, 1992.

As mentioned hereinabove, polynucleotide sequences of the present invention are inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed.

Recombinant viral vectors may be useful for expression of the polypeptides of the present invention since they offer advantages such as lateral infection. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

A variety of prokaryotic or eukaryotic cells can be used as host-expression systems to express the polypeptides of the present invention. These include, but are not limited to, microorganisms, such as bacteria (for example, E. coli including but not limited to E. coli strains BL21 (DE3) plysS, BL21; (DE3)RP and BL21* and B. subtilis) transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Various methods can be used to introduce the expression vector of the present invention into the cells of the host expression system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

According to one embodiment, the polypeptides of the present invention are expressed in plants.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the super-family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively, algae and other non-Viridiplantae can be used for the methods of the present invention.

It will be appreciated that in order to express the polypeptides of the present invention in plants, the constructs encoding same typically comprise a plant-expressible promoter.

As used herein, the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. One exemplary promoter that may be useful in the constructs of the present invention is the RbcS1 promoter (SEQ ID NO: 30), either in addition to or in absence of SEQ ID NO: 31, as exemplified in the Examples section herein under. Of note, other sequences may also be used for plant expression such as set forth in SEQ ID NOs: 48 and 50.

Nucleic acid sequences of the polypeptides of the present invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www.kazusa.or.jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Exemplary polynucleotide sequences that may be used to express the polypeptides of the present invention in plants are set forth in SEQ ID NOs: 20-22.

Plant cells may be transformed stably or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Independent of the host cell system, it will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety. Examples 3-5 and 8 describe purification of resilin and spidersilk polypeptides of the present invention.

Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in a "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Following expression and optional purification of the polypeptides of the present invention, the polypeptides may be polymerized to form an insoluble material from a solution, preferably one with a relatively high concentration of polypeptide. According to one embodiment, the critical concentration of a resilin polypeptide of the present invention is about 50 mg/ml. According to one embodiment, the polypeptide is concentrated by ultracentrifugation.

Generally, crosslinking of proteins can be performed using standard crosslinking agents such as gluteraldahyde, di-isocyanate and Genipin. Exemplary polymerization conditions for particular fibrous polypeptide monomers are presented herein below.

Crosslinking Conditions for Resilin

According to a preferred embodiment, the crosslinking is such that dityrosine bonds are formed. These methods are well known to the person skilled in the art and are discussed by Malencik and Anderson (Biochemistry 1996, 35, 4375-4386), the contents of which are incorporated herein by reference.

In an embodiment, enzyme-mediated cross-linking in the presence of Ru(bpy)3Cl$_2$.6H$_2$O may be employed. Exemplary peroxidases that may be used to crosslink resilin include, but are not limited to horseradish peroxidase, Arthromyces peroxidase, Duox peroxidase from *Caenorhabditis elegans*, Sea urchin ovoperoxidases and Chorion.

Following irradiation, a Ru(III) ion is formed, which serves as an electron abstraction agent to produce a carbon radical within the polypeptide, preferentially at a tyrosine residue, and thus allows dityrosine link formation. This method of induction allows quantitative conversion of soluble resilin or pro-resilin fragments to a very high molecular weight aggregate. Moreover this method allows for convenient shaping of the bioelastomer by introducing recombinant resilin into a glass tube of the desired shape and irradiating the recombinant resilin contained therein.

In another embodiment, UV irradiation is effected in order to crosslink the resilin polypeptides of the present invention [Lehrer S S, Fasman G D. (1967) Biochemistry. 6(3):757-67; Malencik D A, Anderson S R. (2003) Amino Acids. 25(3-4): 233-47], although care must be taken not to damage the protein through exposure to this radiation. UVB radiation cross-linking may also be undertaken in the presence or absence of riboflavin. In the absence of riboflavin, a substantial amount of cross-linking takes place within one hour of exposure. The crosslinking time is substantially reduced if riboflavin is present. Still further, cross-linking may be effected with ultra-violet light in the presence of coumarin or by white light in the presence of fluorescein. An analysis of the dityrosine may be performed using conventional methods such as high performance liquid chromatography measurements in order to ascertain the extent of dityrosine cross-link formation.

Metal ions and H$_2$O$_2$ may also be used to induce dytirosine formation through Fenton's reaction [Ali F E, J Inorg Biochem. 98(1):173-84].

Crosslinking Conditions for Elastin:

Following heating above the transition temperature (Tm), elastin may be crosslinked using the following oxidizing agents: lysil oxidase bis(sulfosuccimidyl)suberate, pyrroloquinoline quinine (PQQ), catechol/peroxidase reagent, 1-ethyl-3-(3-dimethylaminopropyl)carbodiimide in the presence of N-hydroxybenzotriazole, N-(3-dimethylaminopropyl)-N-ethylcarbodiimide hydrochloride (EDC), 1-hydroxybenzotriazole hydrate (HOBt); 1,6-diisocyanatohexane (HOBt); glutaraldehyde; N-hydroxysuccinimide (NHS), genipin.

Elastin may also be crosslinked by γ-irradiation, or, following functionalization with methacrylate, it may also be photocrosslinked.

Crosslinking Conditions for Silk:

Silk polypeptides, such as spider silk and silkworm silk may be polymerized into β sheets using organic solvents, such as methanol. Alternatively, the silk polypeptides may be solubilized in water followed by dehydration in order to form B sheets.

Crosslinking Conditions for Collagen:

Collagen may be crosslinked by glutaraldehyde and other chemical crosslinking agents, by glycation using different sugars, by Fenton reaction using metal ions such as cupper, by lysine oxidase or by UV radiation.

To determine the effect of cross-links and the optimal number of cross-links per monomer unit, the resilience of a cross-linked polymer can be measured using methods known in the art. The level of cross-linking can vary provided that the resulting polymer displays the requisite resilient properties. For example, when the cross-linking is by gamma-irradiation, the degree of cross-linking is a function of the time and energy of the irradiation. The time required to achieve a desired level of cross-linking may readily be computed by exposing non-cross-linked polymer to the source of radiation for different time intervals and determining the degree of resilience (elastic modulus) of the resulting cross-linked material for each time interval. By this experimentation, it will be possible to determine the irradiation time required to produce a level of resiliency appropriate for a particular application.

The extent of cross-linking may be monitored during the reaction or pre-determined by using a measured amount of reactants. For example, in the case of resilin polypeptides, since—the dityrosine cross-link is fluorescent, the fluorescence spectrum of the reactant mixture may be monitored during the course of a reaction to determine the extent of cross-linking at any particular time. Once the desired level of cross-linking is achieved (indicated by reaching a predetermined fluorescence intensity) a peroxidase-catalysed reaction may be quenched by for example the addition of glutathione.

The polypeptides of the present invention may be used as are or they may be blended with polysaccharides in order to generate novel composite materials.

Thus, according to another aspect of the present invention, there is provided an isolated composite comprising a fibrous polypeptide and a polysaccharide.

As used herein the term "composite" refers to a substantially solid material that is composed of two or more discrete materials, one being the fibrous polypeptide, the other the polysaccharide, each of which retains its identity, e.g., physical characteristics, while contributing desirable properties to the composite.

The term "isolated" as used herein refers to the composite being substantially free from other substances (e.g., other cells, proteins, nucleic acids, etc.) in its in-vivo environment (e.g in the case of resilin-chitin composites, removed from other insect wing components). According to another embodiment, the composites are also isolated from (i.e. removed from) solid supports (i.e. are non-immobilized).

Exemplary polysaccharides contemplated for the composites of the present invention include, but are not limited to chitin, cellulose, starch, dextran, glucan, chitosan, alginate and hyaluronic acid.

The cellulose may be in the form of powder such as Sigmacell, cellulose whiskers, cellulose threads or 3D structures such as paper or scaffolds. Whisker preparation is typically performed by hydrolysis of cellulose with 60% $H_2SO_4$ for 1 to 6 hours at 60° C. followed by sonication. The suspension is then diluted in double distilled $H_2O$ (DDW) followed by repeated cycles (at least 5) of resuspension with DDW and centrifugation to remove the acid. Finally, the whiskers pellet is dialyzed against DDW while monitoring the pH up to 7. Whiskers quality may be monitored by Transfer Electron Microscopy (TEM).

According to one embodiment of this aspect of the present invention, the monomers of the fibrous polypeptides of the present invention comprise polysaccharide binding domains (e.g. heterologous polysaccharide binding domains). Such polysaccharide binding domains allows directional binding between the polysaccharide and the fibrous polypeptide at defined points of contact. Furthermore, the affinity of the fibrous polypeptide for the polysaccharide may be adjusted according to the polysaccharide binding domain.

Other composites which are contemplated by the present invention include those comprising two fibrous polypeptides wherein at least one of which comprises a heterologous polysaccharide binding domain.

Such composites may also comprise polysaccharides. Thus composites of two fibrous polypeptides and a polysaccharide are also contemplated by the present invention.

It is expected that the composites of the present invention comprise enhanced characteristics (e.g. increased strength) compared to the constituent fibrous polypeptide since the flat and ordered surface of the polysaccharide (e.g. cellulose whisker) may serve as a template for assembly of the fibrous polypeptide that usually requires shearing and elongation stress.

In order to generate the composites of the present invention, suspensions of monomers of the fibrous polypeptides and the polysaccharides (e.g. cellulose whiskers)—for example at approximately 2% solid content, are blended together.

Exemplary ratio of the component suspension include: 100/0, 90/10, 80/20, 70/30, 60/40, 50/50, 40/60, 30/70, 20/80, 10/90, and 0/100.

The mixed solutions may be cast onto suitable molds (e.g. Teflon or polystyrene) following which appropriate assembly and crosslinking is optionally effected.

As mentioned above, the type of crosslinking depends on the fibrous polypeptide of the composite. The crosslinking may be effected in the presence of other fibrous polypeptides to generate the two fibrous polypeptide/polysaccharide composites described herein above.

The present invention also contemplates coating the novel composites. According to one embodiment, the coating is comprised of fibrous polypeptides. In this method, following the crosslinking of the composites, dipping in solutions of other fibrous polypeptides may be carried out. The fibrous proteins in the coating will typically be absorbed into the composite. Following coating, a suitable polymerization method may be used depending on the actual fibrous polypeptide of the coating. For example, a cellulose-resilin composite may be dipped in a solution containing silk monomers. Subsequently the composite may be transferred into 90% methanol solution which promotes silk β-sheet formation resulting in a cellulose-resilin-silk composite material.

The composites of the present invention may be combined with other polymers in blends and adducts to manipulate the degradation and mechanical properties of the material. Practically any biocompatible polymer may be combined with the composites. In a preferred embodiment, the added polymer is biodegradable. Exemplary biodegradable polymers include natural polymers and their synthetic analogs, including polysaccharides, proteoglycans, glycosaminoglycans, collagen-GAG, collagen, fibrin, and other extracellular matrix components, such as elastin, fibronectin, vitronectin, and laminin. Hydrolytically degradable polymers known in the art include, for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyhydroxyalkanoates, poly (amide-enamines), polyamides, poly (amino acids), polyacetals, polyethers, biodegradable polycyanoacrylates, biodegradable polyurethanes and polysaccharides. For example, specific biodegradable polymers that may be used in the present invention include but are not limited to, polylysine, poly (lactic acid) (PLA), poly (glycolic acid) (PGA), copolymers and mixtures of PLA and PGA, e. g., poly (lactide-co-glycolide) (PLG), poly (caprolactone) (PCL), poly (lactide-co-caprolactone) (PLC), and poly (glycolide-co-caprolactone) (PGC).

Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al., J. Am. Chem. Soc. 123: 9480, 2001; Lim et al., J. Am. Chem. Soc. 123: 2460, 2001; Langer, Acc. Chen 7. Res. 33: 94, 2000; Langer, J. Control Release 62: 7, 1999; and Uhrich et al., Chem. Rev. 99: 3181, 1999.

The composites of the present invention may also be combined with non-biodegradable polymers. For example, polypyrrole, polyanilines, polythiophene, and derivatives thereof are useful electrically conductive polymers that can provide additional stimulation to seeded cells or neighboring tissue. Exemplary non-biodegradable polymers include, but are not limited to, polystyrene, polyesters, non-biodegradable polyurethanes, polyureas, poly (ethylene vinyl acetate), polypropylene, polymethacrylate, polyethylene, polycarbonates, and poly (ethylene oxide).

The importance of biopolymer based biomaterials is constantly increasing in the field of reconstructive medicine. In the recent years, the focus of this field has turned from the search for inert materials for implantation to development of biopolymer based materials that interact with the tissue and promote its correct regeneration. Furthermore, synthetic implants often fail the test of long term biocompatibility requiring their replacement during the lifetime of a patient which is a major drawback. With respect to reconstructive medicine, polysaccharides and protein polymers have been extensively investigated.

When used in vivo, and in particular inside the body of a subject, e.g., a human patient, it is important that the composites of the present invention be biocompatible. A "biocompatible" material is not substantially mutagenic, antigenic, inflammatory, pyrogenic, or hemolytic. Furthermore, it must neither exhibit substantial cytotoxicity, acute systemic toxicity, or intracutaneous toxicity, nor significantly decrease clotting time. In vivo and in vitro tests for these undesirable biological activities are well known in the art; examples of such assays are given, for example, in U.S. Pat. No. 5,527,610, the contents of which are incorporated by reference. Also, when used in vivo, the materials may be biogradable.

In the event that toxicity or immunogenicity, for example, occurs in a relevant composite, methods for modulating these undesirable effects are known in the art. For example, "tanning" of the composite by treating it with chemicals such as aldehydes (e.g., glutaraldehyde) or metaperiodate will substantially decrease both toxicity and immunogenicity. Preferably, the composites used to make devices for in vivo use are also sterilizable.

As mentioned, the composites of the present invention may be used in the field of reconstructive medicine such as for the generation of scaffolds.

As used herein, the term "scaffold" refers to a 3D matrix upon which cells may be cultured (i.e., survive and preferably proliferate for a predetermined time period).

The scaffold may be fully comprised of the composites of the present invention, or may comprise a solid support on which is layered the composites of the present invention.

A "solid support," as used refers to a three-dimensional matrix or a planar surface (e.g. a cell culture plate) on which cells may be cultured. The solid support can be derived from naturally occurring substances (i.e., protein based) or synthetic substances. Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support.

Therapeutic compounds or agents that modify cellular activity can also be incorporated (e.g. attached to, coated on, embedded or impregnated) into the scaffold composite material or a portion thereof. In addition, agents that act to increase cell attachment, cell spreading, cell proliferation, cell differentiation and/or cell migration in the scaffold may also be incorporated into the scaffold. Such agents can be biological agents such as an amino acid, peptides, polypeptides, proteins, DNA, RNA, lipids and/or proteoglycans.

Suitable proteins which can be used along with the present invention include, but are not limited to, extracellular matrix proteins [e.g., fibrinogen, collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-$\alpha$, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-$\beta$, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

Additionally and/or alternatively, the scaffolds of the present invention may comprise an antiproliferative agent (e.g., rapamycin, paclitaxel, tranilast, Atorvastatin and trapidil), an immunosuppressant drug (e.g., sirolimus, tacrolimus and Cyclosporine) and/or a non-thrombogenic or anti-adhesive substance (e.g., tissue plasminogen activator, reteplase, TNK-tPA, glycoprotein IIb/IIIa inhibitors, clopidogrel, aspirin, heparin and low molecular weight heparins such as enoxiparin and dalteparin).

The scaffolds of the present invention may be administered to subjects in need thereof for the regeneration of tissue such as connective tissue, muscle tissue such as cardiac tissue and pancreatic tissue. Examples of connective tissues include, but are not limited to, cartilage (including, elastic, hyaline, and fibrocartilage), collagen, adipose tissue, reticular connective tissue, embryonic connective tissues (including mesenchymal connective tissue and mucous connective tissue), tendons, ligaments, and bone.

The composites of the present invention may thus be used for treating a cartilage or bone disease or condition.

Exemplary cartilage conditions include, but are not limited to osteoarthritis, limited joint mobility, gout, rheumatoid arthritis, osteoarthritis, chondrolysis, scleroderma, degenerative disc disorder and systemic lupus erythematosus.

As used herein, the term "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the term "subject" refers to mammals, including, but not limited to, humans, canines and horses.

It will be appreciated that the composites of the present invention comprises a myriad of medical uses other than for tissue regeneration and for treating cartilage and bone diseases including, but not limited to treatment of urinary incontinence (e.g. urethral bulking), as a healing aid for burn patients and as a dressing to prevent bleeding.

In addition, other medical applications may also benefit from the elasticity, biodegradability and/or biovavailabiliy of the composites of the present invention. For example, after abdominal surgery, the intestines and other abdominal organs tend to adhere to one another and to the abdominal wall. It is thought that this adhesion results from post-surgical inflammation, however, anti-inflammatory drugs delivered directly to the abdominal region dissipate quickly. The composites of the present invention (e.g. those comprising resilin) may be used to deliver anti-inflammatory drugs to the abdominal region.

A soft and flexible composite may be implanted between the abdominal wall and internal organs, for example, by attaching it to the abdominal wall, without cutting internal organs, which would lead to infection. The anti-inflammatory drug can be released from the composite over a period of months. While previous researchers have attempted to use hydrogels, hyaluronic acid-based membranes, and other materials to solve these problems, such materials tend to degrade quickly in the body; a longer resident period is necessary to prevent adhesion.

In another embodiment, the composites of the present invention may be used to coat a metallic stent. Because the composites may be made flexible, they will expand with the stent without ripping, while the stiffness of the metal stent will prevent the composites from elastically assuming its previous shape. The composites being highly bioavailable may release heparin or other anti-coagulants or anti-inflammatory agents to prevent the formation of clots or scar tissue, which could close off the blood vessel or throw off a thrombus that could cause circulatory problems, including stroke, elsewhere in the body. Alternatively or in addition, angiogenic agents may be used to promote the remodeling of the blood vessel surrounding the stent. Indeed, any biomolecule, small molecule, or bioactive agent may be combined with the composites of the present invention. Such molecules may be covalently or non-covalently linked with the composites.

The composites of the present invention may also be used to prepare "long term" medical devices. Unlike typical permanent medical devices, the composites of the present invention will degrade over time. For example, the material may be fabricated into a biodegradable cardiac stent. Preferably, the composites are combined with a harder polymer that plastically forms for the production of stents. Exemplary polymers include any of the polymers listed above, preferably biodegradable polymers. The bio-rubber acts as a plasticizer that enables the stent to expand into the desired shape after implantation. The stent increases the diameter of the blood vessel to allow easier circulation, but, because the stent is biodegradable, surrounding blood vessels increase in diameter without thrombosis or covering the stent with scar tissue, which would reclose the blood vessel. The time the stent should remain in place and retain its shape before degradation will vary from patient to patient and depend partially on the amount of blockage and the age of the patient (e.g., older patients require more time to heal). One skilled in the art will easily be able to adjust the molecular weight and cross-link density of the composites in the stent to adjust the degradation rate. As for the coated stent, the degradable stent may release biomolecules, small molecules, bioactive agents, or some combination of these in situ.

The composites of the present invention may also be used to support in vivo sensors and catheters. The composites may be constructed into a chamber for an optical fiber-based sensor or a coating for a catheter that is inserted into the area of interest. In a sensor, the chamber contains a specific chromophore-bonded receptor for the molecule of interest. When an analyte attaches to the receptor, the chromophore will either emit or absorb light at an specific wavelength. The absorption or emission may be detected by an apparatus connected to the optical fiber. The sensor may be used for short term, continuous monitoring, for example, for ten to fifteen days. Likewise, a catheter may be used to periodically deliver drugs or other small molecules or bioactive agents to a specific site or intravenously. Use of biodegradable composites of the present invention reduces the formation of scar tissue which would ordinarily form around a shunt or other implant that is used for more than two weeks. The degradation rate of the composite should be optimized so that there is not significant degradation of the material while it is in place in the patient.

The composites of the present invention may also be used for other wounds that are hard to close or that fail to heal properly through normal physiologic mechanisms. For example, diabetics often get skin injuries ("diabetic ulcers"), especially in the lower extremities, which take a long time to heal or fail to heal properly due to poor circulation. The use of the present composites to deliver antibiotics or anti-inflammatory agents to these wounds will aid healing and provide a cover for the wound.

Other implantable medical devices which may be fabricated from the composites of the present invention include artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arteriovenous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like.

Of note, the cellulose produced by *Gluconacetobacter xylinus* is most suitable for medical applications. The Bacterial cellulose (BC) produced by these bacteria has high mechanical strength combined with negligible foreign body and inflammatory responses that make it an attractive material for development of medical applications. BC has excellent water retaining properties which make it suitable for production of chronic wound burn dressings and even artificial skin. Furthermore BC and BC composites can be shaped into almost any desired three-dimensional structure.

The composites of the present invention may be formulated as pharmaceutical and/or cosmetic compositions.

The term "cosmetic composition" as used herein refers to a composition formulated for external application to human or animal skin, nails, or hair for the purpose of beautifying, coloring, conditioning, or protecting the body surface. The present cosmetic composition can be in any form including for example: a gel, cream, lotion, makeup, colored cosmetic formulations, shampoo, hair conditioner, cleanser, toner, aftershave, fragrance, nail enamel, and nail treatment product.

The phrase "colored cosmetic formulation" refers to cosmetics containing pigment including for example eye shadow, lipsticks and glosses, lip and eye pencils, mascara, and blush.

As mentioned, the composites of the present invention may also be used as cosmetic agents for treatment of skin and hair.

Thus, the present invention contemplates the composites (e.g. comprising collagen) of the present invention as a substance which can be topically applied, optionally in combination with other active substance such as for example a vitamin (vitamin A, C, E or their mixtures) or other topically active substances including but not limited to avarol, avarone or plant extracts, such as Extr. Cepae or Extr. Echinaceae pallidae. The composites of the present invention may be formulated as topical agents in the form of creams, ointments, lotions or gels such as a hydrogels e.g. on the basis of polyacrylate or an oleogel e.g. made of water and Eucerin.

Oleogels comprising both an aqueous and a fatty phase are based particularly on Eucerinum anhydricum, a basis of wool wax alcohols and paraffin, wherein the percentage of water and the basis can vary. Furthermore additional lipophilic components for influencing the consistency can be added, e.g. glycerin, polyethylene glycols of different chain length, e.g. PEG400, plant oils such as almond oil, liquid paraffin, neutral oil and the like. The hydrogels of the present invention can be produced through the use of gel-forming agents and water, wherein the first are selected especially from natural products such as cellulose derivatives, such as cellulose ester and ether, e.g. hydroxyethyl-hydroxypropyl derivatives, e.g. tylose, or also from synthetic products such as polyacrylic acid derivatives, such as Carbopol or Carbomer, e.g. P934, P940, P941. They can be produced or polymerized based on known regulations, from alcoholic suspensions by adding bases for gel formation.

The cosmetic compositions may comprise other agents capable of conditioning the body surface including, for example humectants; emollients; oils including for example mineral oil; and shine enhancers including for example dimethicone and cyclomethicone. The present conditioning agents may be included in any of the present pharmacological and/or cosmetic compositions.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the collagen accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient. Thus, for treatment of urinary incontinence, the compositions of the present invention may be administered directly to the area surrounding the urethra. For treatment of cartilage diseases, the compositions of the present invention may be administered by intra-articular administration via a joint (e.g. directly into the knee, elbow, hip, sternoclavicular, temporomandibular, carpal, tarsal, wrist, ankle, intervertebral disk or a ligamentum flavum. For disc replacement, the pharmaceutical compositions of the present invention may also be administered directly into the pulposus.

According to a particular embodiment of this aspect of the present invention, the composites of the present invention may be administered directly into the discs for total disc replacement, total disc nucleus pulposus replacement or disc nucleus polposus augmentation and repair or directly into the breast for breast augmentation. According to this embodiment, the composites may be comprised in injectable non-crosslinked formulations. Following injections of such formulations, photopolymerization may be initiated in situ. This may be effected using classical crosslinking techniques including gluteraldehyde, or crosslinking via sugar molecules.

According to one embodiment, in-situ crosslinking of the injectable formulation may be affected by addition of an appropriate buffer (e.g. PBS pH 7.4) together with 200 µM of $CuCl_2$ and 10 mM of $H_2O_2$ so as to generate dityrosine formation.

According to another embodiment, in situ crosslinking is effected using the same components described herein above, but the pH is maintained at 5.2. This leads to modification of the tyrosines into DOPA. Following injection of the materials 0.1-0.5 mM of Sodium periodate may be added to form DOPA-DOPA bridges resulting in crosslinking of the fibrous polypeptides.

According to another embodiment, in situ crosslinking is effected using tyrosine crosslinking techniques involving $H_2O_2$ and radiation of the injected material with UV.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (composite) effective to prevent, alleviate or ameliorate symptoms of a disorder (e.g. cartilage or bone disease).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a polypeptide" or "at least one polypeptide" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions, illustrate the invention in a nonlimiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Construction of Resilin Chimeric Genes

Preparation of Resilin cDNA

According to Elvin et al [Nature. 437: 999-1002, 2005] resilin is mostly expressed at the pupa level in *D. melanogaster*. Therefore, RNA was extracted from this stage for cDNA preparation. RNA was extracted from *D. melanogaster* pupas using TRI® Reagent (Sigma, St. Louis, Mo.). Reverse transcription of the resilin cDNA was performed with M-MLV RT (H—) (Promega corporation, Madison Wis.) with oligo(dT)$_{15}$ primer according to the manufacturers instructions.

Construction of Resilin Fusion Proteins:

Four resilin genes were designed for expression in *E. coli*;
1. Resilin 17 elastic repeats including the native putative chitin binding domain (gi|45550440, nucleotides 698-1888) referred to as Res-ChBD gene. (Protein sequence: SEQ ID NO: 11, 55; polynucleotide sequence: SEQ ID NO:17)
2. Resilin 17 elastic repeats and the native linker for N-terminal fusions and sole expression of a gene similar to Elvin et al, [Nature. 437: 999-1002, 2005] (nucleotides 698-1666) referred to as Resilin (Protein sequence: SEQ ID NO: 14, 56; polynucleotide sequence: SEQ ID NO: 15).
3. *Clostridium cellulovorans* CBD (CBDclos) fused to Resilin 17 elastic repeats referred to as CBD-resilin (Protein sequence: SEQ ID NO: 12, 57; polynucleotide sequence: SEQ ID NO: 18).
4. Resilin (Gene No. 2) fused to CBD, referred to as Resilin-CBD (Protein sequence: SEQ ID NO: 13, 58; polynucleotide sequence: SEQ ID NO: 19).

PCR primers were designed in order to construct the genes mentioned herein above as detailed in Table 12, herein below. A standard PCR method was designed suitable for all reactions: 94° C. for 4 minutes, 35 cycles of 94° C. for 1 minute, 56° C. for 1 minute, 72° C. for 1 minute and 72° C. for 4 minutes. All DNA products were separated on a 1% agarose gel. Appropriate bands were excised with a scalpel and the DNA was purified with HiYield™ Gel/PCR DNA extraction kit (RBC Taipei, Taiwan).

TABLE 12

| No | Primer name | Sequence | Description | Tm° C. |
|---|---|---|---|---|
| 1 | resCBD1.1 | CCATGGGACCGGAGCCACCAG TTAACTC (SEQ ID NO: 1) | Forward primer of resilin + NcoI site | 55 |

TABLE 12-continued

| No | Primer name | Sequence | Description | Tm° C. |
|---|---|---|---|---|
| 2 | resCHBDRev | GGATCCTTAAGGACCGCTGGG ACCACTG (SEQ ID NO: 2) | Reverse primer of resilin + chitin binding domain + BamHI site | 57 |
| 3 | resbmh1_rev | GGATCCCTCATCGTTATCGTAG TCAGCG (SEQ ID NO: 3) | Reverse primer of resilin 17 repeats + BamHI site for N-terminal fusion | 56 |
| 4 | CBD6P11 | GTCTAGAAATAATTTTGTTTAA CTTTAAGAAGGAG (SEQ ID NO: 4) | Forward primer of CBD using pET-CSCP[37] as template + XbaI site | 56 |
| 5 | CBDRes2 | AACTGGTGGCTCCGGCATATCA AATGTTGCAGAAGTAGGATTA ATTATTG_ (SEQ ID NO: 5) | Reverse primer of CBD + resilin overhang (pink) for PCR fusion cloning | 56 |
| 6 | CBDRes3 | TTCTGCAACATTTGATCCGGAG CCACCAGTTAACTC (SEQ ID NO: 6) | Forward primer of resilin + CBD overhang (blue) for PCR fusion cloning | 56 |
| 7 | CBDRes4 | GGATCCTTACTCATCGTTATCG TAGTCAGCG (SEQ ID NO: 7) | Reverse primer of resilin 17 repeats + stop codon and BamHI site | 56 |

Construction of Res-ChBD:

Res-ChBD was the first gene that was constructed directly from the cDNA and served as PCR template for cloning of all the other resilin genes. The PCR was performed according to Table 13 herein below. Ex Taq™ (Takara, Madison Wis.) is a proofreading enzyme suitable for TA cloning.

TABLE 13

| Ingredient | Volume (μl) |
|---|---|
| TaKaRa Ex Taq ™ (5 units/μl) | 0.25 |
| 10× Ex Taq Buffer (Mg$^{2+}$ plus) | 5 |
| dNTP Mixture (2.5 mM each) | 4 |
| Resilin cDNA | 1 |
| Primer 1 resCBD1.1 (10 μmol) | 1 |
| Primer 2 resCHBDRev (10 μmol) | 1 |
| Sterilized distilled water | Up to 50 |

The 1200 base pair product (FIG. 1B) was purified and cloned into pGEM-T Easy vector (Promega Corporation, Madison Wis.). The presence of resilin-ChBD was verified by sequencing. The sequencing was performed using T7 and Sp6 primers that are complimentary to pGEM-T Easy vector. The sequencing results confirmed the cloning of the two resilin variants according to Ardelll and Anderson [Insect Biochem Mol Biol. 31: 965-70, 2002]. Variant A was chosen for further work.

Finally, the Res-ChBD was digested with NcoI, NotI restriction enzymes and cloned into pHis-parallel3 vector (FIG. 2) which contains an N-terminal His tag and a rTev cleavage site enabling purification of the protein on Ni-NTA column and removal of the His tag if desired.

Construction of CBD-Resilin:

This gene was constructed by PCR-fusion method [Hobert O. (2002) Biotechniques. 32: 728-30]. A pET-CSCP vector [Levy et al., 2004, Biomaterials 25: 1841-1849] was used as template for CBD amplification by PCR and the Res-ChBD product described herein above was used as template for resilin amplification. In the first round, two separate PCRs were performed. The CBD was amplified using primers No. 4 & 5. The resilin was amplified with primers 6 & 7. The first amplification was performed with Deep Vent$_R$ DNA Polymerase (NEB Inc. Ipswich, Mass.). By the end of the reactions, 1 μl of each product (FIG. 3A) were mixed to serve as a template for the second step PCR. In this step, primers 4 and 7 were used. The PCR was performed under the same conditions except the usage of Ex Taq™ (Takara, Madison Wis.) to allow TA cloning. The 1600 base pair product was purified and cloned into pBluescript SK+ (Ferments, Md.) (FIG. 3B). The presence of CBD-resilin was verified by sequencing with T7 and T3 primers. The complete gene was digested with NcoI and NotI enzymes and cloned into pHis-parallel3 vector.

Construction of Resilin-CBD and Resilin (Genes 2 & 4):

The resilin gene was amplified using primers No. 1 and 3. The enzyme used for amplification was PfuTurbo® (Stratagene corporation, LA Jolla Calif.). The PCR mixture used for generating DNA encoding Resilin-CBD and Resilin (genes 2 and 4) is described in Table 14, herein below.

TABLE 14

| Ingredient | Volume (μl) |
|---|---|
| PfuTurbo ® (Stratagene corporation, LA Jolla CA) | 1 |
| 10× cloned Pfu DNA polymerase reaction buffer | 5 |
| dNTP Mixture (2.5 mM each) | 1 |
| pGEM-T-ResCHBD (10 ng/μl) | 1 |
| Primer 1 resCBD1.1 (10 μmol) | 1 |
| Primer 3 resbmh1_rev (10 μmol) | 1 |
| Sterilized distilled water | Up to 30 |

Following the PCR reaction described herein above, 7 μl of 10× Taq polymerase reaction buffer, 1 μl of Taq polymerase (Bio-lab, Israel), 1 μl of dNTP mixture and sterilized distilled water to a volume of 100 μl was added to the reaction tube. The tube was then incubated at 72° C. for 30 minutes in order to add A nucleotides to the PCR product. The final product was purified and cloned into pGEM-T Easy vector (Promega corporation, Madison Wis.). The presence of the resilin gene was verified by sequencing as described above.

For construction of Resilin-CBD gene, the resilin fragment was digested with NcoI, BamHI and cloned into pET3d (Novagen, EMD Chemicals, Inc. CA) upstream to the CBD-clos gene followed by digestion of the Resilin-CBD with NcoI, EcoRI and cloning into pHis-parallel3 vector digested with the same enzymes.

Resilin expression vector (gene 2) was constructed by digestion of pGEM-T Easy-Resilin with NcoI, NotI. In this way a stop codon was added to the gene that allowed its direct expression. The gene was subsequently cloned into pHisparallel3 digested with the same enzymes.

Example 2

Expression of Resilin Chimeric Genes

All four vectors were transformed into BL21(DE3) (Novagen, EMD Chemicals, Inc. CA). 5 ml of overnight cultures were grown in LB medium with 100 mg/L ampicillin at 37° C. rotary shaker. These starters were used for inoculation of 250 to 350 ml of LB with 100 mg/L ampicillin at a ratio of 1/100 of starter to culture volume. At O.D.600 of 0.8 to 0.9 expression was induced with 1 mM IPTG. Four hours after induction, bacteria were harvested by centrifugation. 6H-Res-ChBD pellet was divided to 50 ml aliquots for initial analysis and the pellets were stored at −80° C.

Example 3

Purification of Resilin-ChBD and Characterization Thereof

Small Scale Batch Purification of 6H-Res-ChBD:

Bacterial pellet of 50 ml was re-suspended in 2 ml of 100 mM Tris pH 7.5, 0.1% Triton® X-100, Complete™ (Roche, Basel Switzerland). Bacteria were lyzed by sonication with pulsed bursts for 2 minutes on ice. The soluble and bacterial precipitates were separated by centrifugation at 15000 RPM for 10 minutes at 4° C. SDS-PAGE analysis revealed that the Res-ChBD product is mostly found in the soluble fraction (FIG. 4 lanes 1, 2). 500 µl of lysate were added into 1.5 ml eppendorf tube containing 75 µl pre-equilibrated HIS-Select® Nickel Affinity Gel, (Sigma, St. Louis, Mo.). Purification was performed according to the product manual. Final elution was repeated twice with 100 µl elution buffer containing 0.4 M imidazole.

Binding Assay of Purified 6H-Res-ChBD to Cellulose and Chitin:

25 mg of chitin (Sigma) and 50 mg of cellulose (Sigmacell) were added to two separate 1.5 ml eppendorf tubes. The materials were washed with PBS followed by addition of 50 µl of affinity purified protein solution. 450 µl of PBS were added to each tube to a total reaction volume of 500 µl. A third tube containing chitin only was supplemented with 500 µl of PBS as negative control since practical grade chitin (Sigma Cat No. C7170) that contained proteins was used. The tubes were incubated under gentle spinning for 30 minutes at RT followed by centrifugation. The supernatant was removed (unbound fraction) and the pellets were washed 3 times with 500 µl of PBS. The final pellets were boiled with 50 µl of 2× sample application buffer (SAB). Samples of unbound and wash fractions from each tube were also boiled with SAB. Samples were loaded on 12.5% SDS-PAGE gel.

Binding Assay of Crude Extracts of 6H-Res-ChBD to Cellulose and Chitin:

Bacterial lysates were produced from 50 ml pellets as described above. Cellulose and chitin binding assays were performed with 3 increasing lysate volumes as described in Table 15 below, in 2 ml eppendorf tubes.

TABLE 15

| Tube No. | Lysate volume (µl) | 10× PBS (µl) | DDH$_2$O (µl) | Carbohydrate |
|---|---|---|---|---|
| 1 | 50 | 50 | 400 | Cellulose 50 mg |
| 2 | 125 | 50 | 325 | Cellulose 50 mg |
| 3 | 250 | 50 | 200 | Cellulose 50 mg |
| 4 | 50 | 50 | 400 | Chitin 25 mg |
| 5 | 125 | 50 | 325 | Chitin 25 mg |
| 6 | 250 | 50 | 200 | Chitin 25 mg |

6H-Res-ChBD Thermostability Assay:

15 µl of affinity purified protein were added to 3 0.5 ml eppendorf tubes. The tubes were incubated at 85° C. for 15, 30, 60 minutes. By the end of the incubation the tubes were transferred to ice and centrifuged at 14000 rpm for 10 minutes. Subsequently, the samples were boiled with 2×SAB and loaded on 12.5% SDS-PAGE gel.

Small-Scale FPLC Purification of 6H-Res-ChBD:

Bacterial lysates were produced from 50 ml pellets as described above. The lysate was filtered with a syringe filter of 0.45 µm for the purpose of FPLC (GE, Uppsala Sweden) purification on HisTrap™ HP (GE, Uppsala Sweden) Ni-NTA 1 ml column pre-equilibrated according to the user manual.

The purification program was run as follows:

Binding buffer; 20 mM NaHPO$_4$, 0.5 M NaCl, 10 mM imidazole

Elution buffer; 20 mM NaHPO$_4$, 0.5 M NaCl, 0.5 M imidazole 1. 5 column volumes (CV) of binding buffer at 1 ml/min.
2. 5 ml injection of the lysate at 1 ml/min
3. 5 CV wash with the binding buffer.
4. linear gradient up to 500 mM imidazole for 10 min at 0.7 ml/min with the elution buffer
5. Equilibration with 5 CV of binding buffer at 1 ml/min.

Eluted proteins were detected at O.D.280. 400 µl fractions were collected and 10 µl of samples boiled with SAB were loaded on a 12.5% SDS-PAGE gel.

Production of Soluble High Molecular Weight 6H-res-ChBD:

FPLC fractions 9 to 18 were collected to a total volume of 2 ml and imidazole was removed by three dialyses against 200 ml of polymerization buffer; 15 mM NaH$_2$PO$_4$, 150 mM NaCl pH 7.5. 500 µl of dialyzed protein was incubated at 85° C. for 10 min followed by O.N. incubation at 4° C. Polymerization was performed by adding 20 µl of 40 mM ammonium persulfate and 20 µl of 0.5 mM Ru(bpy)3Cl$_2$.6H$_2$O (Sigma) dissolved in the polymerization buffer to an Eppendorf tube containing 40 µl of the purified protein. The samples were subjected to sun light for 5 minutes followed by boiling with 2×SAB. Samples were loaded on 12.5% SDS-PAGE gel.

Medium-Scale FPLC Purification of 6H-Res-ChBD:

Bacterial pellets from 200 ml culture were resuspended in 15 ml of lysis buffer as described above. Bacteria were lyzed by sonication with pulsed bursts for 5 minutes in an ice bath. The soluble and bacterial precipitates were separated by centrifugation at 15000 RPM for 10 minutes at 4° C. The purification was performed with FPLC using the same method as described above. Eluted proteins were detected at O.D.280. 400 µl fractions were collected and 10 µl of samples boiled with SAB were loaded on a 12.5% SDS-PAGE gel.

Production of Solid 6H-Res-ChBD:

Following medium-scale FPLC purification described herein above, the fractions were collected into two different dialysis bags; concentrated fractions No. 4 to 7 (6 ml) and diluted fractions No. 3, 8-12. The dialysis was performed as described above. The concentration of the concentrated peak was 10 mg/ml by O.D. 280 nm measurement. The sample was loaded on a Vivaspin 6 10,000 MWCO (Sartorius Stedim Biotech, Aubagne, France) ultrafiltration tube and centrifuged at 5000 g for 40 minutes. The final product gave around 500 μl at protein concentration of 160 mg/ml. 40 μl of concentrated protein were pipette into an eppendorf tube that was added 4 μl of 250 mM ammonium persulfate and 1 μl of 0.5 mM Ru(bpy)$_3$Cl$_2$.6H$_2$O. Immediately following the exposure of the tube to sunlight a solid polymer formed in the tube. The reaction was stopped after 5 minutes by washing the polymer with water when no more polymerization could be observed.

Results

Small-Scale Batch Purification of 6H-Res-ChBD:

Purification was effected as illustrated in FIG. 4 lanes 3-7.

Binding Assay of Purified 6H-Res-ChBD to Cellulose and Chitin:

Coomassie blue staining of the proteins revealed that 6H-Res-ChBD binds both to chitin and cellulose with a higher affinity to chitin (FIG. 5). The presence of protein in the unbound fraction is explained due the saturation chitin/cellulose with Res-ChBD protein.

Binding Assay of Crude Extracts of 6H-Res-ChBD to Cellulose and Chitin:

Coomassie blue staining of the gels revealed that no cellulose binding was detected in crude lysates comprising the 6H-Res-ChBD (FIG. 6A, 6B lanes 2-5), contrasting the binding results following affinity chromatography AC purification. Nevertheless, the affinity of the protein to chitin remained high as displayed by the crude lysates results. At 50 and 125 μl of crude lysate loaded on 25 mg of chitin, nearly 100% of the protein precipitated and very little protein remained in the unbound fraction (FIG. 6B lanes 7-10, FIG. 6C lanes 2-5). When 250 μl of lysate were applied, the amount of bound protein continued to increase but a larger band was detected in the unbound fraction probably due to saturation of the binding sites (FIG. 6C lanes 6-9).

6H-Res-ChBD Thermostability Assay:

Heat treatment displayed that 6H-Res-ChBD is stable at 85° C. for 1 hour (FIG. 7). As indicated in the Materials and Methods, the proteins were immediately transferred to ice following the heat treatment. This could explain the band shift observed in the gel due to initiation of coacervation process.

Small-Scale FPLC Purification of 6H-Res-ChBD:

The results of the purification process are illustrated in FIGS. 8A-B.

Production of Soluble High Molecular Weight 6H-Res-ChBD:

The results of the solubilization process are illustrated in FIG. 9.

Medium-Scale FPLC Purification of 6H-Res-ChBD:

The results of the purification process are illustrated in FIGS. 10A-B.

Example 4

Expression and Purification of 6H-Resilin 17 Elastic Repeats without any Polysaccharide Binding Domain (PBD) (SEQ ID NO: 56)

Following expression of the resilin of SEQ ID NO: 56 in *E. coli*, the soluble protein was purified on a Ni-NTA column as illustrated in FIG. 11. In addition, the protein was found to be thermostable and was polymerized into solid resilin in the same manner as resilin-ChBD.

Example 5

Purification of CBD-Resilin (SEQ ID NO: 57) and Characterization Thereof

Following expression of CBD-resilin in bacteria, it was found to be expressed in inclusion bodies (FIG. 12).

Cells were lyzed by sonication in 0.1% Triton® X-100, Complete™ (Roche, Basel Switzerland).

The insoluble fraction was precipitated by centrifugation.

The supernatant was removed and the inclusion bodies were washed as follows:

1. Resuspension with PBS buffer, 1% Triton® X-100, 1 mM EDTA, for 30 minutes with gentle shaking followed by centrifugation.
2. Resuspension with PBS buffer, 1% Triton® X-100, for 30 minutes with gentle shaking followed by centrifugation.
3. Resuspension with PBS buffer for 30 minutes with gentle shaking followed by centrifugation.

From that stage, purification of the inclusion bodies was performed by one of two methods.

1. Ni-NTA purification under denaturizing conditions. IBs were solubilzed in 20 mM phosphate buffer pH 7.5, 20 mM imidazole, 0.5 M NaCl, 6 M GuHCl. The proteins were loaded on pre-equilibrated Ni-NTA column and the proteins were eluted with a linear gradient of 20 mM phosphate buffer pH 7.5, 0.5 M imidazole, 0.5 M NaCl, 6 M GuHCl. The fractions containing the peak that was detected at O.D. 280 nm were collected and were refolded by dialysis against 50 mM Tris pH 7.5 buffer. The proteins were analyzed by SDS-PAGE. Refolding of the protein was assayed by cellulose binding assay (FIG. 13).
2. Washed IB were solubilzed in 20 mM phosphate buffer pH 7.5, 20 mM imidazole, 0.5 M NaCl, 6 M GuHCl. The proteins were then injected to the ÄKTAprime™ plus (GE Healthcare, Uppsala Sweden) loaded with Ni-NTA column and purified using an automated refolding protocol that is programmed in the machine. The fractions containing the refolded proteins were collected (FIG. 14) followed by cellulose binding assay. The automated refolded CBD-resilin protein was found mostly in the bound fraction similar to the proteins refolded via standard protocols, involving dialysis of samples purified in the presence of 6M GuHCl or 8M urea, indicating that this method can be applied since it is highly efficient and time saving.

Example 6

Cloning and Expression of Resilin-CBD (SEQ ID NO: 58)

A DNA fragment coding for resilin 17 elastic repeats+ putative resilin linker was cloned upstream to a vector containing the CBD to generate a polynucleotide of SEQ ID NO: 19. The correct insertion was verified by sequence followed by cloning of the gene into pHis parallel3 for protein expression. Expression was performed in BL21 bacteria similarly to all the other proteins. Following protein expression the bacteria were centrifuged and lyzed as described for CBD-resilin. The soluble and insoluble fractions were separated by centrifugation. SDS-PAGE analysis revealed that about 50% of the recombinant protein was found in the soluble fraction. A cellulose binding assay was performed directly on resilin-CBD crude lysates resulting in high affinity binding of resilin-CBD to cellulose (see FIG. 17).

Example 7

Purification of Resilin-CBD (SEQ ID NO: 58)

Following resilin-CBD expression, BL21 bacteria were centrifuged and lyzed as described for the other proteins. The soluble and insoluble fractions were separated by centrifugation. The lysate was filtered with a syringe filter of 0.45 μm. Proteins were then loaded on to a preequilibrated Ni-NTA column and were eluted with a linear gradient of 20 mM phosphate buffer (pH 7.5, 0.5 M imidazole, 0.5 M NaCl). The fractions containing the peak that was detected at O.D. 280 nm were pooled and dialyzed three times against phosphate buffer saline (PBS) to remove the imidazole. The proteins were boiled with X2 sample application buffer (SAB) and analyzed by Coomassie-stained SDS-PAGE (FIG. 16).

Table 16 herein below summarizes the cloned resilin proteins described herein.

TABLE 16

| Protein | Sequence | Number of elastic repeats | Expression vector | Expressed in |
|---|---|---|---|---|
| Resilin | SEQ ID NO: 56 | 17 | pHis-parallel3 | BL21(DE3) |
| Resilin-ChBD | SEQ ID NO: 55 | 17 | pHis-parallel3 | BL21(DE3) |
| CBD-Resilin | SEQ ID NO: 57 | 17 | pHis-parallel3 | BL21(DE3) |
| Resilin-CBD | SEQ ID NO: 58 | 17 | pHis-parallel3 | BL21(DE3) |

Example 8

Heat Resistance and Cellulose Binding Assay of Resilin-CBD (SEQ ID NO: 58)

A sample solution containing the purified resilin-CBD protein was incubated at 85° C. for 15 minutes followed by centrifugation for 15 minutes at 14,000 rpm. 50 μl of the heated protein solution was added to 30 mg of cellulose powder (Sigmacell) for the purpose of cellulose binding assay as described in Example 3. The cellulose binding assay was also performed with a non-heated resilin-CBD solution as control. As shown in FIG. 17, the resilin-CBD protein displays both heat resistance and efficient binding capacity to cellulose that was not compromised by the heat treatment.

Example 9

Solubility of Resilin Proteins in Solutions of Different pH

Materials and Methods

There is increasing evidence that reactive oxygen species (ROS)-induced oxidative stress resulting from enzymatic or metal-catalyzed oxidation (MCO) reactions, can highly affect protein side chains and overall character. Tyrosine is one of the most ROS-sensitive residues in proteins. Its oxidation products include 3,4-dihydroxyphenylalanine (DOPA), dopamine, dopamine quinine, dityrosine (DT) and isoDT. In addition, DOPA is the major product of hydroxyl radical treatment of tyrosine (Ali F. E. et al., Journal of inorganic biochemistry 2004, 98, 173-184). According to Ali et al (2004), MCO of tyrosine in solutions of varying pHs results in varying products such as dityrosine and 3,4-dihydroxyphenylalanine (DOPA).

In order to use the MCO system to achieve these modifications on the resilin proteins, their stability under such pH conditions was analyzed.

Protein solutions of resilin and resilin-ChBD (pH ~7.5) were gently titered with 2M HCl to pH 5.6 or pH 5.4. During the titration, 200 μl samples, representing different pH between the starting point, and the final pH were collected. The samples were incubated at 4° C. for 72 hours to allow for protein precipitation and then centrifuged for 15 minutes at 14000 rpm. The soluble proteins were detected on a Coomassie-stained SDS-PAGE.

Results

In both cases, massive protein precipitation was observed at approximately pH 5. As illustrated in FIG. 18, the proteins remained in solutions of pH up to 5.6 and 5.4, respectively, demonstrating the pH range of solubility of these recombinant proteins. With these fundamental determinations, the effect of MCO on resilin side chains can be studied.

Example 10

Light Induced Polymerization of Resilin Proteins Products in Different pH

Materials and Methods

Resilin and resilin-ChBD protein solutions (50 μl) at varying pH, containing 0.5 mM of Ru(bpy)3Cl$_2$.6H$_2$O and 2.5 mM of ammonium persulfate (APS) were subjected to sunlight for 10 minutes followed by protein separation and detection on a Coomassie-stained SDS-PAGE. Protein samples without Ru(bpy)3Cl$_2$.6H$_2$O and APS were used as control.

Results

In all the samples containing the Ru(bpy)3Cl$_2$.6H$_2$O and APS, high molecular weight products were formed. Nevertheless, the pattern of the seemingly crosslinked products differed according to the pH (FIG. 19, see arrow).

Example 11

Metal-Catalyzed Polymerization of Resilin

Materials and Methods

Purified resilin was dialyzed three times against either 50 mM phosphate buffer (pH 7.5) or deionized water. Following the dialysis, the proteins were incubated at 85° C. for 15 minutes and subsequently centrifuged for 30 minutes at 10000 rpm. Generally, the polymerization was performed according to the MCO method reported by Kato et al (2001) (Kato Y, Kitamoto N, Kawai Y, Osawa T. (2001) The hydrogen peroxide/copper ion system, but not other metal-catalyzed oxidations systems, produces protein-bound dityrosine. Free Radical Biology & Medicine, 31, (5), 624-632) and Ali et al (Ali F E, Barnham K J, Barrow C J, Separovic F. (2004) Metal catalyzed oxidation of tyrosine residues by different oxidation systems of copper/hydrogen peroxide. J Inorg Biochem. 98(1):173-84). All the reactions were performed at a final volume of 250 μl in 1.5 ml eppendorf tubes. The MCO polymerization was performed by adding 4 mmol H$_2$O$_2$ (1 μl of 30% H$_2$O$_2$) and 200 μM CuCl$_2$ (2.5 μl of 20 mM CuCl$_2$ dissolved in H$_2$O) followed by O.N. incubation at 37° C. Tubes with protein solutions only, protein solutions with $H_2O_2$ only or $CuCl_2$ only were used as negative controls. The reactions were terminated by adding 1 mM EDTA. Finally, the samples were boiled in X2 SAB and were analyzed by SDS-PAGE.

Results

Polymerization was achieved in both phosphate buffer and water, as displayed in FIG. 20. Further analysis of these results is under way.

Example 12

Preparation of Recombinant Resilin-Cellulose Whisker Composites

Materials and Methods

His tag-purified protein solutions containing 10 mg/ml of 6H-Res-ChBD (SEQ ID NO: 55) were mounted onto a 10 kDa cutoff Vivaspin Centrifugal Concentrator (Sartorius, UK) and centrifuged at 6000 rpm to a concentration of 100 mg/ml. At this stage, a 200 μl sample was removed and stored for later analysis, while the rest of the solution was further concentrated to 200 mg/ml concentration.

6H-Res-ChBD-cellulose whiskers composites were produced by casting equal volumes of 200 mg/ml 6H-Res-ChBD-cellulose whiskers solution and cellulose whiskers solution (prepared as describe in Bondeson D, Mathew A, Oksman K. (2006) Cellulose 13:171-180) into 150 μl and 75 μl Teflon molds resulting in final protein concentration of 100 mg/ml. 150 μl of a 100 mg/ml pure 6H-Res-ChBD solution was poured into a similar mold as control. Subsequently 250 μM of Ru(bpy)$_3$ and 2.5 mM of ammonium persulfate (APS) were added to each sample solution. The mixtures were homogenized in the molds by pipeting, followed by polymerization by induced crosslinking via exposure to a 500 W tungsten light for 5 seconds.

Results

The 150 μl 6H-Res-ChBD sample (FIG. 21B—far right) and the 75 and 150 μl 6H-Res-ChBD-cellulose whiskers sample composites (FIG. 21B—middle and left, respectively) were removed from the mold and sent to Differential Scanning Calorimetry (DSC) for further analysis.

Example 13

Construction of Spider Silk-CBD Fusion Genes

Materials and Methods

The spider silk (SpS) is a synthetic gene (SEQ ID NO: 23) optimized for expression in *E. coli*. Its sequence is a design of 15 repeats of a monomer consensus derived from the native sequence of the spidroin 1 sequence of Nephila clavipes (Accession P19837).

The SpS synthetic gene was provided in a pET30a vector, which contains an N and C terminal His tag and an Enterokinase cleavage site enabling purification of the protein on Ni-NTA column and removal of the N-terminal His tag if desired.

Construction of SpS-CBD Fusion Genes for Expression in *E. coli*:

*Clostridium cellulovorans* CBD (CBDclos) (SEQ ID NO: 25) was fused to the 3' of the spider silk synthetic gene. The fusion gene is referred to as SpS-CBD (SEQ ID NO: 24).

PCR primers were designed in order to construct the SpS-CBD fusion gene as summarized in Table 17 herein below. The PCR primers will add an N-terminal SpeI and a C-terminal XhoI restriction sites to the CBDclos gene template.

TABLE 17

| SEQ ID No. | Primer name | Sequence | description | Tm° C. |
|---|---|---|---|---|
| 37 | CBDSpeI_for | GACTAGTATGGCAGC GACATCATCAATGTC | Forward primer of CBD160 + SpeI site | 56 |
| 47 | CBDSXhoI_rev | CTCGAGATCAAATGT TGCAGAAGTAGGATT AATTATTG | Reverse primer of CBD160 + XhoI site | 56 |

The CBDclos gene served as a PCR template for cloning of the fusion genes. A standard PCR was performed using Ex Taq™ (Takara, Madison Wis.), which is a proof reading enzyme suitable for TA cloning. The PCR product was purified from a 1% agarose gel and was cloned into pGEM-T Easy vector (Promega Corporation, Madison Wis.). The presence of SpeI-CBDclos-XhoI was verified by sequencing.

Cloning of SpS-CBD

The SpeI-CBDclos-XhoI was cloned into SpeI and XhoI restriction sites on pET30a-SpS vector.

Construction of Spider Silk Genes Optimized for Expression in Tobacco Plants:

The synthetic dragline silk gene (GENEART GmbH Regensburg, Germany, SEQ ID NO: 27) is composed of a repeat unit, which was selected based on a consensus (GPG-GQGPYGPGASAAAAAAGGYGPGYGQQG-PGQQGPGQQ) SEQ ID NO:26 derived from the native sequence of the *Arenaus diadematus* ADF-3 gene (Accession U47855). Multimers encoding this repeat were developed by the use of the condensation method [Lewis et al., Protein Expression and Purification 7, 400-406 (1996)]. The synthetic gene includes the sequence of the monomer limited by the SmaI and NaeI restriction sites, which were used for the development of the multimers with the aid of another unique restriction site (AatII) on the pUC19 vector.

At the end of the spider silk monomer sequence there is an addition of the 3' non-repetitive sequence of the ADF-3 dragline gene. This sequence was shown to contribute to the solubility of the protein [Lazaris et al., Science 295: 472-476 (2002)]. At the 5' of the silk monomer a partial sequence of a synthetic CBDclos gene was added as described herein below.

Construction of 6 Monomer (6 mer) Spider Silk Gene:

In order to construct a 6 mer spider silk gene a double digest was performed as follows:
1. Digest of the synthetic monomer (SEQ ID NO: 26) with SmaI and AatII.

2. Digest of the synthetic monomer (SEQ ID NO: 26) with NaeI and AatII.

The DNA products were purified on a 1% agarose gel and the ligation of the purified fragments yielded a 2 mer spider silk gene. Subsequently, a condensation of 2 mers was performed to create a 4 mer gene and a 4 mer and a 2 mer were condensed to form a 6 mer gene.

Construction of 6 mer-CBDclos Fusion Genes:

The sequence of the CBDclos was optimized for expression in tobacco plants. The CBD synthetic DNA was fused to the 5' of the silk monomer. In order to construct a full length CBDclos-6 mer fusion, a digest of BclI and NcoI restriction sites on the partial CBD-6 mer gene and the full length non synthetic CBDclos was performed.

The fusion of the CBD to the 6 mer gene was made in two orientations:

1. Two 6 mer repeats were fused to the 3' terminal end of CBDclos to create CBDclos-Sp512 (SEQ ID NO: 28). The condensation of two 6 mers was performed as described above.
2. CBDclos was fused in the middle of two 6 mer repeats. The fusion gene is referred to as SpS6-CBD-SpS6 (SEQ ID NO: 29). The cloning of the two 6 mers was performed by double digestion of one CBD-6 mer plasmid with SmaI and NaeI and the other with StuI. The fragments were purified and ligated to form SpS6-CBD-SpS6.

Both CBD-12 mer and SpS6-CBD-SpS6 were cloned into Rubisco's small subunit cassette (includes regulatory elements, such as the promoter, terminator, 5' and 3' untranslated regions cloned from *Chrysanthemum* sp.) SEQ ID NOs: 30 and 31, on the pBINPLUS binary vector. Another expression cassette which was used includes the Cell signal peptide for secretion of the fusion proteins to the apoplast. This signal was fused to the 5' of the fusion genes before the 5'UTR of the Rubisco's small subunit gene.

Table 18 summarizes the cloned spider silk proteins described herein.

TABLE 18

| Protein | Number of monomer repeats | Expression vector/tag | Expressed in |
|---|---|---|---|
| Spider silk (SpS) (SEQ ID NO: 33) | 15 | pET30a/His | BL21(DE3) |
| Spider silk-CBD (SpS-CBD) (SEQ ID NO: 34) | 15 | pET30a/His | BL21(DE3) |
| CBD-spider silk (CBD-SpS12) (SEQ ID NO: 28) | 12 | pBINPLUS/Cell | *N. tabacum*-SR1 |
| Spider silk-CBD-spider silk (SpS6-CBD-SpS6) (SEQ ID NO: 29) | 12 | pBINPLUS | *N. tabacum*-SR1 |

Example 14

Expression and Purification of SpS-CBD Fusion Genes

Materials and Methods

Expression of SpS and SpS-CBDclos proteins in *E. coli*: The pET30a-SpS and pET30a-SpS-CBDclos vectors were transformed into BL21(DE3) (Novagen, EMD Chemicals, Inc. CA). 5 ml of over night cultures were grown in LB medium with 50 mg/l kanamicin at 37° C. on a rotary shaker. These starters were used for inoculation of 250 to 350 ml of LB with 50 mg/l kanamycin at a ratio of 1/100 of starter to culture volume. At O.D.600 of 0.6 to 0.9, expression was induced with 1 mM IPTG. Following four hours from induction, bacteria were harvested by centrifugation. One pellet was divided to 50 ml aliquots for initial analysis and the pellets were stored at −80° C.

FPLC Purification of 6H-SpS and 6H-SpS-CBD:

Bacterial pellet of 300 ml was re-suspended in 5 ml of 100 mM Tris pH 7.5, 0.1% Triton® X-100, Complete™ (Roche, Basel Switzerland). Bacteria were lyzed by sonication with pulsed bursts for 5 minutes on an ice bath. The soluble and bacterial precipitates were separated by centrifugation at 15000 rpm for 10 minutes at 4° C. The soluble fraction of the proteins was filtered with a syringe filter of 0.45 μm for the purpose of FPLC (GE, Uppsala Sweden) purification on His-Trap™ HP (GE, Uppsala Sweden) Ni-NTA 1 ml column pre-equilibrated according to the user manual.

The purification program was run as follows:

Binding buffer; 20 mM $NaHPO_4$, 0.5 M NaCl, 10 mM imidazole

Elution buffer; 20 mM $NaHPO_4$, 0.5 M NaCl, 0.5 M imidazole 1. 5 column volumes (CV) of binding buffer at 1 ml/min.
2. 5 ml injection of the lysate at 1 ml/min
3. 10 CV wash with the binding buffer.
4. linear gradient up to 500 mM imidazole for 15 minutes at 1 ml/min with the elution buffer
5. Equilibration with 10 CV of binding buffer at 1 ml/min.

Eluted proteins were detected at O.D.280. 500 μl fractions were collected and 20 μl of samples boiled with SAB were loaded on a 10% SDS-PAGE gel.

Expression of CBD-SpS12 and SpS6-CBD-SpS6 Proteins in Tobacco Plants

Transformation of Tobacco Plants:

The binary pBINPLUS vector including the Robisco's expression cassette and the fusion genes were introduced into *A. tumefaciens* strain LBA4404 for plant transformation. Leaf-disc transformation was performed with *N. tabacum*-SR1 plants as described previously (DeBlock et al., 1984 The EMBO Journal vol. 3 no. 8 pp. 1681-1689, 1984). More than 15 independent tobacco transformants were generated for each construct, propagated in vitro and transferred to the greenhouse. The presence of the transgene was confirmed by PCR on genomic DNA using specific primers for the Robisco's cassette terminator/promoter. T1 seeds obtained by self-pollination of transformants were harvested and selected further on germination medium containing kanamycin (300 mg 1-1). The sterilization treatment was for 30 seconds in 70% ethanol followed by 5 minutes 2.5% NaOCl.

Expression of CBD-SpS12 and SpS6-CBD-SpS6 by T1 Homozygous Plants:

Protein extraction was performed by grinding 90 mg of transgenic tobacco leaves with chilled extraction buffer (50 mM Tris-HCL pH=7.5, "complete"-protease inhibitor cocktail tablets. Roche-Cat #1697498) in a tissueLyser (Retch Mixer Mill Type MM301/220-240V 50/60 HZ.cat #20.741.0001). Separation of soluble and insoluble fractions was done by centrifugation at 15000 rpm for 10 minutes at 4° C. Soluble and insoluble fractions were boiled with SAB.

Purification of CBD-SpS12 and SpS6-CBD-SpS6 from Transgenic Tobacco Plants:

20 mg of transgenic leaves in 40 ml purification buffer (50 mM Tris-HCL pH=7.5, 10 mM DTT, 0.5 gr cellulose Sigma-cell20, PMSF 1 mM were ground in a blender till a uniform mixture was obtained. Separation of soluble and insoluble fractions was performed by centrifugation at 14000 rpm for 15 minutes at 4° C. The insoluble fraction, which includes the bound CBD fusion proteins, was washed extensively twice in 30 ml extraction buffer each. The bound proteins were eluted from the cellulose pellet by suspension in elution buffer (50 mM Tris-HCL pH=12.5, 10 mM DTT, 0.1% Triton) for 1 hour in a shaking rotor. Separation of the soluble fraction, which includes the eluted CBD fusion protein, was effected by centrifugation at 14000 RPM for 15 minutes at 4° C.

Further Purification of SpS6-CBD-SpS6:

The eluted soluble protein from the procedure detailed above was dialyzed against 5 liter of heat stability test buffer (50 mM sodium phosphate pH=8, 10 mM DTT) over night. Then the sample was centrifuged at 14000 RPM for 10 minutes at 4° C. The soluble protein was subjected to heat treatment in 60-90° C. for 10 minutes, followed by 20 minutes on ice, and centrifuging at a maximum speed for 10 minutes. The soluble protein was also tested for its solubility at a wide range of pHs from 8-2. The pH of the heat stability test buffer was adjusted with 2M HCL until the pH of the solution reached pH=2. For every pH coordinate, a sample was taken for analysis and incubated at 4° C. overnight. To separate soluble from insoluble, the samples were centrifuged at a maximum speed for 10 minutes. The soluble proteins were boiled with SDS-PAGE sample application buffer (SAB).

Qualitative Binding Assay of Purified SpS and SpS-CBD to Cellulose:

30 mg of cellulose (Sigmacell) were added to 1.5 ml eppendorf tubes. The materials were washed with PBS followed by addition of 50 µl of affinity purified protein solution. 450 µl of PBS were added to each tube to a total reaction volume of 500 µl. The tubes were incubated under gentle spinning for 30 minutes at RT followed by centrifugation. The supernatant was removed (unbound fraction) and the pellets were washed for 3 times with 500 µl of PBS. The final pellets were boiled with 50 µl of SAB. Samples of unbound fraction from each tube were also boiled with SAB. Samples were loaded on 10% SDS-PAGE gel.

Quantitative Binding Reversibility Assay of Purified CBD-clos, SpS and SpS-CBDclos to Cellulose:

100 to 600 µg of SpS and SpS-CBD proteins in 500 µL PBS were adsorbed to 30 mg prewashed cellulose (Sigmacell) for 30 minutes at 25° C. Desorption from the cellulose was performed, while the most concentrated protein:cellulose mixture (600 µg+30 mg cellulose) was diluted in individual test tubes to final protein quantity ranging from 600 to 100 µg, followed by mixing for an additional 30 minutes. After centrifugation at 13000 g for 10 minutes, the bound protein concentration was assayed by the Lowry method (The NaOH in the Lowry A solution elutes the bound proteins from the cellulose pellet).

Results

Expression of SpS and SpS-CBDclos Proteins in *E. coli*:

The SpS and SpS-CBD proteins were successfully expressed in *E. coli* (FIG. 22A). SDS-PAGE analysis of soluble and insoluble (IB content) proteins revealed that the SpS protein product is found in the soluble fraction, whereas SpS-CBD protein product is mostly found in the insoluble inclusion bodies (TB) fraction (FIG. 22B).

FPLC Purification of 6H-SpS and 6H-SpS-CBD:

The SpS and SpS-CBD proteins were successfully purified on a Ni-NTA column (FIG. 23A). The purified SpS and SpS-CBD were identified by anti-6HIS antibody (FIG. 23B). When looking at the chromatogram of the purification on Ni-NTA (FIGS. 24A-C), a non specific protein peak can be observed in the control run (FIG. 24A). The protein which was eluted is identified by literature as SlyD. This doesn't interfere with the SpS and SpS-CBD purification as SlyD elutes prior to the fusion proteins (FIG. 24A lanes 5-7).

Qualitative Binding Assay of Purified 15 mer and 15 mer-CBD to Cellulose:

Coomassie blue staining showed that the SpS-CBD was bound to cellulose, with no apparent protein revealed by Coomassie blue in the unbound fraction (FIG. 25 lanes 5-7).

The SpS is mostly found in the unbound fraction following the binding procedure (FIG. 26 lanes 2-4). The SpS protein found in the bound fraction is nonspecifically adsorbed to cellulose. This phenomenon can be explained by the mechanism of proteins adsorption in solid/liquid interfaces [Haynes et al, Colloids and Surfaces B, Biointerfaces. 2:517-566 (1994)] as further demonstrated below.

Quantitative Binding Reversibility Assay of Purified CBD-clos, SpS and SpS-CBDclos to Cellulose:

Adsorption/desorption experiments are critical tests to study the reversible nature of adsorption. A reversible adsorption process is defined if the departure from adsorption equilibrium is infinitesimally small, so that in the reverse process (desorption) the variables characterizing the state of the system return to the same values in the reverse order. Therefore in a reversible adsorption process, the ascending branch (increasing concentration in the solution) and the descending branch (decreasing concentration in the solution) of the isotherm must overlap. If the ascending and descending branches of the isotherm do not overlap, the process is defined as irreversible and the deviation between the ascending and descending branches is defined as hysteresis [Haynes et al, Colloids and Surfaces B, Biointerfaces. 2:517-566(1994)]. The desorption experiments of CBDclos and SpS-CBDclos revealed that a new equilibrium was established after dilution, which was not on the same isotherm (FIG. 26). These results prove that the ascending and descending isotherms do not overlap, which is a prerequisite for irreversible binding. These results demonstrate that under the conditions tested, CBDclos and SpS-CBDclos display similar adsorption behavior and bind almost irreversibly to cellulose. The results also reveal that the ascending and descending branches of the SpS isotherm almost overlap, therefore it can be known for certain that the SpS adsorption to cellulose is not reversible but rather due to protein adsorption in solid/liquid interfaces. Table 19 herein below summarizes the results quantitative binding reversibility assay results.

TABLE 19

| Total protein | Bound (µg)/10 mg cellulose | | | Reverse binding (µg)/10 mg cellulose | | |
|---|---|---|---|---|---|---|
| (µg) | CBD | SpS | SpSr-CBD | CBD | SpS | SpS-CBD |
| 100 | 99.21 | 14.05 | 94.15 | 474.56 | 3.41 | 408.13 |
| 150 | 138.67 | 23.28 | 120.92 | 467.57 | 13.02 | 402.88 |
| 300 | 237.38 | 41.57 | 231.47 | 442.22 | 77.71 | 416.87 |
| 600 | 462.17 | 101.33 | 419.58 | 462.17 | 101.33 | 419.58 |

Expression of CBD-SpS12 and SpS6-CBD-SpS6 by T1 Homozygous Plants:

Four homozygous T1 plants, with elevated protein expression, were isolated:

1. Two plants of CBD-SpS12 number 13.7 and 13.8, which express and secrete CBD-SpS12 to the appoplast were identified, referred to herein as 13.7 and 13.8, respectively.

2. Two plants of SpS6-CBD-SpS6 number 6.4 and 6.8, which express 6 mer-CBD-SpS6 in the cytoplasm were identified, referred to herein as 6.4 and 6.8, respectively.

SDS-PAGE analysis of protein extracts revealed that both CBD-SpS12 and SpS6-CBD-SpS6 bound cellulose and therefore were mostly found in the insoluble fraction (FIGS. 27A-B). With the addition of extra cellulose to the extraction procedure, all the soluble fraction of the CBD fusion proteins bound cellulose.

Purification of CBD-SpS12 and SpS6-CBD-SpS6 from Transgenic Tobacco Plants:

The purification of CBD-SpS12 and SpS6-CBD-SpS6 is based on the unique binding of the fusion CBD proteins to the plant's cell wall. This specific binding confirms that the CBD is active and serves as the first step of purification (FIG. 28A). CBD-containing proteins were shown to bind the cell wall and to precipitate along with the insoluble fractions of the cell extract. The pellet was then treated with elution buffer, leading to release of CBD-containing proteins to the soluble fraction of this elution process (FIG. 28A, lane 6). Further purification of SpS6-CBD-SpS6 is based on the spider silk unique heat stability and solubility at a wide range of pHs. From SDS PAGE analysis it is clear that the SpS6-CBD-SpS6 is heat stable and soluble at a wide range of pHs (FIG. 28B).

Example 15

Metal Catalyzed Polymerization of Spider Silk

Materials and Methods

Purified SpS protein (Example 8), containing 15 tyrosine residues, was dialyzed four times against either 50 mM phosphate buffer (pH 7.5) or deionized water. Following the dialysis, the protein was centrifuged for 10 minutes at 13000 rpm (FIG. 29, lanes 2,3,4). The polymerization reaction was performed according to the MCO method reported by Kato et al (Kato Y, Kitamoto N, Kawai Y, Osawa T. (2001) The hydrogen peroxide/copper ion system, but not other metal-catalyzed oxidations systems, produces protein-bound dityrosine. Free Radical Biology & Medicine, 31, (5), 624-632) and Ali et al (Ali F E, Barnham K J, Barrow C J, Separovic F. (2004) Metal catalyzed oxidation of tyrosine residues by different oxidation systems of copper/hydrogen peroxide. J Inorg Biochem. 98(1):173-84). All the reactions were performed in 250 μl solution volume in 1.5 ml eppendorf tubes. The MCO polymerization was performed by adding 4 mmol $H_2O_2$ (1 μl of 30% $H_2O_2$) and 200 μM $CuCl_2$ (2.5 μl of 20 mM $CuCl_2$ dissolved in $H_2O$) followed by O.N. incubation at 37° C. Tubes with protein solution only, protein solution with $H_2O_2$ only or $CuCl_2$ only were used as negative controls. The reactions were terminated by adding 1 mM EDTA. Finally the samples were boiled in X2 SAB and analyzed by Coomassie-stained SDS-PAGE.

Results

Polymerization was achieved in both phosphate buffer and water, as displayed in FIG. 29, lanes 3 and 7.

Example 16

Method for Preparation of Spider Silk and Cellulose Whiskers Sponges with/without CBD Materials and Methods Aqueous protein solutions (5 wt %) were mixed with cellulose whiskers in a Teflon mold. After obtaining a homogenous solution, 100% methanol was added to the protein-whiskers mixture to a final concentration of 15% (stirring was manually performed). The mold was placed in a –80° C. freezer for more than 1 hour. The protein-whiskers frozen solution was freeze-dried to generate a sponge. This method is based on Nazarov R et al. Porous 3-D scaffolds from regenerated silk fibroin. Biomacromolecules (2004): 5, 718-726.

Example 17

Preparation of Recombinant a Spider Silk-Cellulose Whisker Sponge

The purified SpS protein was dialyzed against water for 18 hours, changing the water four times (the first change after 12 hours and the following three changes every two hours). After dialysis, the protein aqueous solution was concentrated to 5 wt % (FIG. 30, lanes 2 and 4 vs. 5). The concentrated SpS protein was then mixed with cellulose whiskers in a Teflon mold to yield a desired ratio of 100/0%, 30/70%, 0/100%, respectively.

Example 18

Determination of Tm of Silk-Whisker Composites

Materials and Methods

Sponges, generated according to the methods described in Example 16 and 17, were analyzed by differential scanning calorimetry (DSC). For each run, ~5 mg of sample was used, and the thermogram was recorded from 0-300° C. at a heating rate of 5° C./min, under nitrogen.

Results

The DSC analysis (FIGS. 31A-C) shows three different thermogram profiles. In the composite spider silk-cellulose whiskers thermogram the transition temperature peak 2 of spider silk and cellulose whiskers alone disappeared and a higher peak appeared at 243.69° C. Table 20 summarizes the transition temperature peaks from DSC thermograms of whiskers, silk and 70% whiskers/30% silk sponges. This analysis demonstrates that the silk-whisker combination leads to a significant increase in whiskers transition temperature peak2. Table 20 summarizes the transition temperature peaks from DSC thermograms of whiskers, silk and 70% whiskers/30% silk sponges.

TABLE 20

|  | Transition temp. peak1 (° c.) | Tg (° c.) | Transition temp. peak2 (° c.) |
| --- | --- | --- | --- |
| Cellulose whiskers (FIG. 2A) | 93.04 | — | 193.71 |
| Silk (FIG. 2B) | 81.07 | 175.44 | 267.66 |
| 70% whiskers/30% silk(FIG. 2C) | 87.56 | — | 243.69 |

| Sample | Transition temp. peak1 (° C.) | Transition temp. peak2 (° C.) |
| --- | --- | --- |
| Cellulose whiskers | 93.04 | 193.71 |
| Silk | 81.07 | 175.44 (Tg) |
| 70% whiskers/30% silk | 87.56 | 243.69 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composite comprising resilin and a polysaccharide selected from the group consisting of cellulose, starch, dextran, glucan, chitosan, alginate and hyaluronic acid.

2. A composite comprising a fibrous polypeptide and a polysaccharide, said fibrous polypeptide comprising a heterologous polysaccharide binding domain, the composite being non-immobilized.

3. The composite of claim 1, wherein said resilin comprises a polysaccharide binding domain.

4. The composite of claim 3, wherein said polysaccharide binding domain is a heterologous polysaccharide binding domain.

5. The composite of claim 3, wherein said polysaccharide binding domain is selected from the group consisting of a cellulose binding domain, a chitosan binding domain, an alginate binding domain, a starch binding domain, a dextran binding domain, a glucan binding domain and an hyaluronic acid binding domain.

6. The composite of claim 2, wherein said fibrous polypeptide is selected from the group consisting of mussel byssus protein, resilin, silkworm silk protein, spider silk protein, collagen, elastin and fragments thereof.

7. The composite of claim 1, further comprising an additional fibrous polypeptide being selected from the group consisting of mussel byssus protein, silkworm silk protein, spider silk protein, collagen, elastin and fragments thereof.

8. The composite of claim 1 being crosslinked.

9. The composite of claim 1 being non-crosslinked.

10. A composite comprising at least two non-identical fibrous polypeptides, wherein a first fibrous polypeptide of said at least two non-identical fibrous polypeptides comprises an amino acid sequence encoding a resilin polypeptide attached to a heterologous polysaccharide binding domain.

11. A scaffold comprising the composite of claim 1.

12. A pharmaceutical composition comprising the composite of claim 1.

13. A cosmetic composition comprising the composite of claim 1.

14. A composite comprising resilin and cellulose.

* * * * *

SEQUENCE LISTING

<160> NUMBER OF SEQ ID NOS: 62

<210> SEQ ID NO 1
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 1
ccatgggacc ggagccacca gttaactc                                          28

<210> SEQ ID NO 2
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 2
ggatccttaa ggaccgctgg gaccactg                                          28

<210> SEQ ID NO 3
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 3
ggatccctca tcgttatcgt agtcagcg                                          28

<210> SEQ ID NO 4
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 4
gtctagaaat aattttgttt aactttaaga aggag                                  35

<210> SEQ ID NO 5
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 5
aactggtggc tccggcatat caaatgttgc agaagtagga ttaattattg                  50

<210> SEQ ID NO 6
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 6
ttctgcaaca tttgatccgg agccaccagt taactc                                 36

```
<210> SEQ ID NO 7
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 7
ggatccttac tcatcgttat cgtagtcagc g                              31

<210> SEQ ID NO 8
<211> LENGTH: 15
<212> TYPE: PRT
<213> ORGANISM: Artificial sequence
<220> FEATURE:
<223> OTHER INFORMATION: Elastic repeat unit of resilin

<400> SEQUENCE: 8

Gly Gly Arg Pro Ser Asp Ser Tyr Gly Ala Pro Gly Gly Gly Asn
1               5                   10                  15

<210> SEQ ID NO 9
<211> LENGTH: 325
<212> TYPE: PRT
<213> ORGANISM: Artificial sequence
<220> FEATURE:
<223> OTHER INFORMATION: Minimal resilin polypeptide sequence derived
      from Drosophila

<400> SEQUENCE: 9

Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Gly Arg Pro Ser Asp Ser
                20                  25                  30

Tyr Gly Ala Pro Gly Gly Gly Asn Gly Gly Arg Pro Ser Asp Ser Tyr
            35                  40                  45

Gly Ala Pro Gly Gln Gly Gln Gly Gln Gly Gln Gly Gln Gly Gly Tyr
        50                  55                  60

Ala Gly Lys Pro Ser Asp Thr Tyr Gly Ala Pro Gly Gly Gly Asn Gly
65                  70                  75                  80

Asn Gly Gly Arg Pro Ser Ser Ser Tyr Gly Ala Pro Gly Gly Gly Asn
                85                  90                  95

Gly Gly Arg Pro Ser Asp Thr Tyr Gly Ala Pro Gly Gly Gly Asn Gly
            100                 105                 110

Gly Arg Pro Ser Asp Thr Tyr Gly Ala Pro Gly Gly Gly Gly Asn Gly
        115                 120                 125

Asn Gly Gly Arg Pro Ser Ser Ser Tyr Gly Ala Pro Gly Gln Gly Gln
    130                 135                 140

Gly Asn Gly Asn Gly Gly Arg Ser Ser Ser Ser Tyr Gly Ala Pro Gly
145                 150                 155                 160

Gly Gly Asn Gly Gly Arg Pro Ser Asp Thr Tyr Gly Ala Pro Gly Gly
                165                 170                 175

Gly Asn Gly Gly Arg Pro Ser Asp Thr Tyr Gly Ala Pro Gly Gly Gly
            180                 185                 190

Asn Asn Gly Gly Arg Pro Ser Ser Ser Tyr Gly Ala Pro Gly Gly Gly
        195                 200                 205

Asn Gly Gly Arg Pro Ser Asp Thr Tyr Gly Ala Pro Gly Gly Gly Asn
    210                 215                 220

Gly Asn Gly Ser Gly Gly Arg Pro Ser Ser Ser Tyr Gly Ala Pro Gly
225                 230                 235                 240
```

```
Gln Gly Gln Gly Gly Phe Gly Arg Pro Ser Asp Ser Tyr Gly Ala
            245                 250                 255

Pro Gly Gln Asn Gln Lys Pro Ser Asp Ser Tyr Gly Ala Pro Gly Ser
        260                 265                 270

Gly Asn Gly Asn Gly Gly Arg Pro Ser Ser Ser Tyr Gly Ala Pro Gly
        275                 280                 285

Ser Gly Pro Gly Gly Arg Pro Ser Asp Ser Tyr Gly Pro Pro Ala Ser
    290                 295                 300

Gly Ser Gly Ala Gly Ala Gly Gly Ser Gly Pro Gly Gly Ala Asp
305                 310                 315                 320

Tyr Asp Asn Asp Glu
                325

<210> SEQ ID NO 10
<211> LENGTH: 163
<212> TYPE: PRT
<213> ORGANISM: Artificial sequence
<220> FEATURE:
<223> OTHER INFORMATION: Clostridium cellulovorans derived cellulose
      binding domain (CBD)
<220> FEATURE:
<221> NAME/KEY: misc_feature
<223> OTHER INFORMATION: cellulose binding domain (CBD)

<400> SEQUENCE: 10

Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
            20                  25                  30

Ala Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Gly Asp His Ala Gly
    50                  55                  60

Ala Leu Leu Gly Asn Ser Tyr Val Asp Asn Thr Gly Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Ala Gln Thr Asn Asp Tyr Ser Phe Asp Ala Ser Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro

<210> SEQ ID NO 11
<211> LENGTH: 399
<212> TYPE: PRT
<213> ORGANISM: Artificial sequence
<220> FEATURE:
<223> OTHER INFORMATION: Resilin 17 elastic repeats including the
      native putative chitin binding domain (Res-CHBD)

<400> SEQUENCE: 11

Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Gly Arg Pro Ser Asp Ser
            20                  25                  30
```

```
Tyr Gly Ala Pro Gly Gly Asn Gly Gly Arg Pro Ser Asp Ser Tyr
         35                  40                  45
Gly Ala Pro Gly Gln Gly Gln Gly Gln Gly Gln Gly Gly Tyr
     50                  55                  60
Ala Gly Lys Pro Ser Asp Thr Tyr Gly Ala Pro Gly Gly Asn Gly
65                   70                  75                  80
Asn Gly Gly Arg Pro Ser Ser Tyr Gly Ala Pro Gly Gly Asn
                 85                  90                  95
Gly Gly Arg Pro Ser Asp Thr Tyr Gly Ala Pro Gly Gly Asn Gly
                100                 105                 110
Gly Arg Pro Ser Asp Thr Tyr Gly Ala Pro Gly Gly Gly Asn Gly
             115                 120                 125
Asn Gly Gly Arg Pro Ser Ser Ser Tyr Gly Ala Pro Gly Gln Gly Gln
130                 135                 140
Gly Asn Gly Asn Gly Gly Arg Ser Ser Ser Tyr Gly Ala Pro Gly
145                 150                 155                 160
Gly Gly Asn Gly Gly Arg Pro Ser Asp Thr Tyr Gly Ala Pro Gly Gly
                 165                 170                 175
Gly Asn Gly Gly Arg Pro Ser Asp Thr Tyr Gly Ala Pro Gly Gly Gly
             180                 185                 190
Asn Asn Gly Gly Arg Pro Ser Ser Ser Tyr Gly Ala Pro Gly Gly Gly
             195                 200                 205
Asn Gly Gly Arg Pro Ser Asp Thr Tyr Gly Ala Pro Gly Gly Gly Asn
         210                 215                 220
Gly Asn Gly Ser Gly Gly Arg Pro Ser Ser Ser Tyr Gly Ala Pro Gly
225                 230                 235                 240
Gln Gly Gln Gly Gly Phe Gly Gly Arg Pro Ser Asp Ser Tyr Gly Ala
                 245                 250                 255
Pro Gly Gln Asn Gln Lys Pro Ser Asp Ser Tyr Gly Ala Pro Gly Ser
             260                 265                 270
Gly Asn Gly Asn Gly Gly Arg Pro Ser Ser Ser Tyr Gly Ala Pro Gly
         275                 280                 285
Ser Gly Pro Gly Gly Arg Pro Ser Asp Ser Tyr Gly Pro Pro Ala Ser
     290                 295                 300
Gly Ser Gly Ala Gly Gly Ala Gly Gly Ser Gly Pro Gly Gly Ala Asp
305                 310                 315                 320
Tyr Asp Asn Asp Glu Pro Ala Lys Tyr Glu Phe Asn Tyr Gln Val Glu
                 325                 330                 335
Asp Ala Pro Ser Gly Leu Ser Phe Gly His Ser Glu Met Arg Asp Gly
             340                 345                 350
Asp Phe Thr Thr Gly Gln Tyr Asn Val Leu Leu Pro Asp Gly Arg Lys
         355                 360                 365
Gln Ile Val Glu Tyr Gly Ala Asp Gln Gln Gly Tyr Arg Pro Gln Ile
     370                 375                 380
Arg Tyr Glu Gly Asp Ala Asn Asp Gly Ser Gly Pro Ser Gly Pro
385                 390                 395

<210> SEQ ID NO 12
<211> LENGTH: 503
<212> TYPE: PRT
<213> ORGANISM: Artificial sequence
<220> FEATURE:
<223> OTHER INFORMATION: Clostridium cellulovorans CBD (CBDclos) fused
      to Resilin 17 elastic repeats (CBD-resilin)
```

<400> SEQUENCE: 12

```
Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
                20                  25                  30

Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
50                  55                  60

Ala Leu Leu Gly Asn Ser Tyr Val Asp Asn Thr Gly Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Ala Gln Thr Asn Asp Tyr Ser Phe Asp Ala Ser Ser Thr Pro Val
130                 135                 140

Val Asn Pro Lys Val Thr Gly Tyr Ile Gly Gly Ala Lys Val Leu Gly
145                 150                 155                 160

Thr Ala Pro Gly Pro Asp Val Pro Ser Ser Ile Ile Asn Pro Thr Ser
                165                 170                 175

Ala Thr Phe Asp Pro Glu Pro Pro Val Asn Ser Tyr Leu Pro Pro Ser
            180                 185                 190

Asp Ser Tyr Gly Ala Pro Gly Gln Ser Gly Pro Gly Gly Arg Pro Ser
        195                 200                 205

Asp Ser Tyr Gly Ala Pro Gly Gly Asn Gly Gly Arg Pro Ser Asp
210                 215                 220

Ser Tyr Gly Ala Pro Gly Gln Gly Gln Gly Gln Gly Gln Gly Gln Gly
225                 230                 235                 240

Gly Tyr Ala Gly Lys Pro Ser Asp Thr Tyr Gly Ala Pro Gly Gly Gly
                245                 250                 255

Asn Gly Asn Gly Gly Arg Pro Ser Ser Tyr Gly Ala Pro Gly Gly
            260                 265                 270

Gly Asn Gly Gly Arg Pro Ser Asp Thr Tyr Gly Ala Pro Gly Gly Gly
        275                 280                 285

Asn Gly Gly Arg Pro Ser Asp Thr Tyr Gly Ala Pro Gly Gly Gly
290                 295                 300

Asn Gly Asn Gly Gly Arg Pro Ser Ser Tyr Gly Ala Pro Gly Gln
305                 310                 315                 320

Gly Gln Gly Asn Gly Asn Gly Gly Arg Ser Ser Ser Tyr Gly Ala
                325                 330                 335

Pro Gly Gly Gly Asn Gly Gly Arg Pro Ser Asp Thr Tyr Gly Ala Pro
            340                 345                 350

Gly Gly Gly Asn Gly Gly Arg Pro Ser Asp Thr Tyr Gly Ala Pro Gly
        355                 360                 365

Gly Gly Asn Asn Gly Gly Arg Pro Ser Ser Tyr Gly Ala Pro Gly
370                 375                 380

Gly Gly Asn Gly Gly Arg Pro Ser Asp Thr Tyr Gly Ala Pro Gly Gly
385                 390                 395                 400

Gly Asn Gly Asn Gly Ser Gly Gly Arg Pro Ser Ser Tyr Gly Ala
                405                 410                 415
```

-continued

```
Pro Gly Gln Gly Gln Gly Gly Phe Gly Gly Arg Pro Ser Asp Ser Tyr
            420                 425                 430

Gly Ala Pro Gly Gln Asn Gln Lys Pro Ser Asp Ser Tyr Gly Ala Pro
            435                 440                 445

Gly Ser Gly Asn Gly Asn Gly Gly Arg Pro Ser Ser Tyr Gly Ala
        450                 455                 460

Pro Gly Ser Gly Pro Gly Arg Pro Ser Asp Ser Tyr Gly Pro Pro
465                 470                 475                 480

Ala Ser Gly Ser Gly Ala Gly Gly Ala Gly Gly Ser Gly Pro Gly Gly
                485                 490                 495

Ala Asp Tyr Asp Asn Asp Glu
            500
```

<210> SEQ ID NO 13
<211> LENGTH: 494
<212> TYPE: PRT
<213> ORGANISM: Artificial sequence
<220> FEATURE:
<223> OTHER INFORMATION: Resilin fused to CBD through a linker
      polypeptide

<400> SEQUENCE: 13

```
Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Arg Pro Ser Asp Ser
            20                  25                  30

Tyr Gly Ala Pro Gly Gly Asn Gly Gly Arg Pro Ser Asp Ser Tyr
            35                  40                  45

Gly Ala Pro Gly Gln Gly Gln Gly Gln Gly Gln Gly Gly Tyr
        50                  55                  60

Ala Gly Lys Pro Ser Asp Thr Tyr Gly Ala Pro Gly Gly Asn Gly
65              70                  75                  80

Asn Gly Gly Arg Pro Ser Ser Ser Tyr Gly Ala Pro Gly Gly Asn
                85                  90                  95

Gly Gly Arg Pro Ser Asp Thr Tyr Gly Ala Pro Gly Gly Asn Gly
            100                 105                 110

Gly Arg Pro Ser Asp Thr Tyr Gly Ala Pro Gly Gly Gly Asn Gly
        115                 120                 125

Asn Gly Gly Arg Pro Ser Ser Ser Tyr Gly Ala Pro Gly Gln Gly Gln
130                 135                 140

Gly Asn Gly Asn Gly Gly Arg Ser Ser Ser Tyr Gly Ala Pro Gly
145                 150                 155                 160

Gly Gly Asn Gly Gly Arg Pro Ser Asp Thr Tyr Gly Ala Pro Gly Gly
                165                 170                 175

Gly Asn Gly Gly Arg Pro Ser Asp Thr Tyr Gly Ala Pro Gly Gly
            180                 185                 190

Asn Asn Gly Gly Arg Pro Ser Ser Ser Tyr Gly Ala Pro Gly Gly Gly
                195                 200                 205

Asn Gly Gly Arg Pro Ser Asp Thr Tyr Gly Ala Pro Gly Gly Gly Asn
    210                 215                 220

Gly Asn Gly Ser Gly Gly Arg Pro Ser Ser Ser Tyr Gly Ala Pro Gly
225                 230                 235                 240

Gln Gly Gln Gly Gly Phe Gly Gly Arg Pro Ser Asp Ser Tyr Gly Ala
                245                 250                 255

Pro Gly Gln Asn Gln Lys Pro Ser Asp Ser Tyr Gly Ala Pro Gly Ser
            260                 265                 270
```

```
Gly Asn Gly Asn Gly Gly Arg Pro Ser Ser Tyr Gly Ala Pro Gly
            275                 280                 285

Ser Gly Pro Gly Gly Arg Pro Ser Asp Ser Tyr Gly Pro Pro Ala Ser
290                 295                 300

Gly Ser Gly Ala Gly Gly Ala Gly Gly Ser Gly Pro Gly Gly Ala Asp
305                 310                 315                 320

Tyr Asp Asn Asp Glu Gly Ile Pro Asp Pro Gly Met Ala Ala Thr Ser
                325                 330                 335

Ser Met Ser Val Glu Phe Tyr Asn Ser Asn Lys Ser Ala Gln Thr Asn
                340                 345                 350

Ser Ile Thr Pro Ile Ile Lys Ile Thr Asn Thr Ser Asp Ser Asp Leu
            355                 360                 365

Asn Leu Asn Asp Val Lys Val Arg Tyr Tyr Thr Ser Asp Gly Thr
370                 375                 380

Gln Gly Gln Thr Phe Trp Cys Asp His Ala Gly Ala Leu Leu Gly Asn
385                 390                 395                 400

Ser Tyr Val Asp Asn Thr Ser Lys Val Thr Ala Asn Phe Val Lys Glu
                405                 410                 415

Thr Ala Ser Pro Thr Ser Thr Tyr Asp Thr Tyr Val Glu Phe Gly Phe
                420                 425                 430

Ala Ser Gly Arg Ala Thr Leu Lys Lys Gly Gln Phe Ile Thr Ile Gln
            435                 440                 445

Gly Arg Ile Thr Lys Ser Asp Trp Ser Asn Tyr Thr Gln Thr Asn Asp
            450                 455                 460

Tyr Ser Phe Asp Ala Ser Ser Thr Pro Val Val Asn Pro Lys Val
465                 470                 475                 480

Thr Gly Tyr Ile Gly Gly Ala Lys Val Leu Gly Thr Ala Pro
                485                 490

<210> SEQ ID NO 14
<211> LENGTH: 329
<212> TYPE: PRT
<213> ORGANISM: Artificial sequence
<220> FEATURE:
<223> OTHER INFORMATION: Resilin fused to a C' linker polypeptide
      (Elvin)

<400> SEQUENCE: 14

Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Gly Arg Pro Ser Asp Ser
            20                  25                  30

Tyr Gly Ala Pro Gly Gly Gly Asn Gly Gly Arg Pro Ser Asp Ser Tyr
        35                  40                  45

Gly Ala Pro Gly Gln Gly Gln Gly Gln Gly Gln Gly Gln Gly Gly Tyr
50                  55                  60

Ala Gly Lys Pro Ser Asp Thr Tyr Gly Ala Pro Gly Gly Gly Asn Gly
65                  70                  75                  80

Asn Gly Gly Arg Pro Ser Ser Tyr Gly Ala Pro Gly Gly Asn
            85                  90                  95

Gly Gly Arg Pro Ser Asp Thr Tyr Gly Ala Pro Gly Gly Gly Asn Gly
                100                 105                 110

Gly Arg Pro Ser Asp Thr Tyr Gly Ala Pro Gly Gly Gly Asn Gly
            115                 120                 125

Asn Gly Gly Arg Pro Ser Ser Ser Tyr Gly Ala Pro Gly Gln Gly Gln
130                 135                 140
```

Gly Asn Gly Asn Gly Gly Arg Ser Ser Ser Tyr Gly Ala Pro Gly
145                 150                 155                 160

Gly Gly Asn Gly Gly Arg Pro Ser Asp Thr Tyr Gly Ala Pro Gly Gly
            165                 170                 175

Gly Asn Gly Gly Arg Pro Ser Asp Thr Tyr Gly Ala Pro Gly Gly Gly
        180                 185                 190

Asn Asn Gly Gly Arg Pro Ser Ser Tyr Gly Ala Pro Gly Gly Gly
        195                 200                 205

Asn Gly Gly Arg Pro Ser Asp Thr Tyr Gly Ala Pro Gly Gly Gly Asn
    210                 215                 220

Gly Asn Gly Ser Gly Gly Arg Pro Ser Ser Tyr Gly Ala Pro Gly
225                 230                 235                 240

Gln Gly Gln Gly Gly Phe Gly Gly Arg Pro Ser Asp Ser Tyr Gly Ala
            245                 250                 255

Pro Gly Gln Asn Gln Lys Pro Ser Asp Ser Tyr Gly Ala Pro Gly Ser
        260                 265                 270

Gly Asn Gly Asn Gly Arg Pro Ser Ser Tyr Gly Ala Pro Gly
    275                 280                 285

Ser Gly Pro Gly Gly Arg Pro Ser Asp Ser Tyr Gly Pro Pro Ala Ser
    290                 295                 300

Gly Ser Gly Ala Gly Gly Ala Gly Gly Ser Gly Pro Gly Gly Ala Asp
305                 310                 315                 320

Tyr Asp Asn Asp Glu Gly Ser Asn His
                325

<210> SEQ ID NO 15
<211> LENGTH: 1007
<212> TYPE: DNA
<213> ORGANISM: Artificial sequence
<220> FEATURE:
<223> OTHER INFORMATION: Resilin fused a linker polynucleotide sequence

<400> SEQUENCE: 15
ccatgggacc ggagccacca gttaactcgt atctacctcc gtccgatagc tatggagcac      60
cgggtcagag tggtcccggc ggcaggccgt cggattccta tggagctcct ggtggtggaa     120
acggtggacg gccctcagac agctatggcg ctccaggcca gggtcaagga cagggacaag     180
gacaaggtgg atatgcaggc aagccctcag ataccatgg agctcctggt ggtggaaatg     240
gcaacggagg tcgtccatcg agcagctatg gcgctcctgg cggtggaaac ggtggtcgtc     300
cttcggatac ctacggtgct cctggtggcg gaaatggtgg acgccatcg gacacttatg     360 gtgctcctgg tggtggtgga atggcaacg gcggacgacc ttcaagcagc tatggagctc     420
ctggtcaagg acaaggcaac ggaaatggcg gtcgctcatc gagcagctat ggtgctcctg     480
gcggtggaaa cggcggtcgt ccttcggata cctacggtgc tcccggtggt ggaaacggtg     540
gtcgtccttc ggatacttac ggcgctcctg gtggcggcaa taatggcggt cgtccctcaa     600
gcagctacgg cgctcctggt ggtggaaacg gtggtcgtcc atctgacacc tatggcgctc     660
ctggtggcgg taacggaaac ggcagcggtg gtcgtccttc aagcagctat ggagctcctg     720
gtcagggcca aggtggattt ggtggtcgtc catcggactc ctatggtgct cctggtcaga     780
accaaaaacc atcagattca tatggcgccc ctggtagcgg caatggcaac ggcggacgtc     840
cttcgagcag ctatggagct ccaggctcag gacctggtgg ccgaccctcc gactcctacg     900 gaccccagc ttctgatcg ggagcaggt gcgctgagg cagtggaccc ggcggcgctg     960
actacgataa cgatgaggga tccaatcact agtgaattcg cggccgc                1007

<210> SEQ ID NO 16
<211> LENGTH: 513
<212> TYPE: PRT
<213> ORGANISM: Artificial sequence
<220> FEATURE:
<223> OTHER INFORMATION: 15 sps spider silk polypeptide

<400> SEQUENCE: 16

```
Ser Gly Arg Gly Gly Leu Gly Gly Gln Gly Ala Gly Ala Ala Ala
1               5                   10                  15

Ala Gly Gly Ala Gly Gln Gly Gly Tyr Gly Gly Leu Gly Ser Gln Gly
                20                  25                  30

Thr Ser Gly Arg Gly Gly Leu Gly Gly Gln Gly Ala Gly Ala Ala Ala
            35                  40                  45

Ser Ala Gly Gly Ala Gly Gln Gly Gly Tyr Gly Gly Leu Gly Ser Gln
50                  55                  60

Gly Thr Ser Gly Arg Gly Gly Leu Gly Gly Gln Gly Ala Gly Ala Ala
65                  70                  75                  80

Ala Ala Ala Gly Gly Ala Gly Gln Gly Gly Tyr Gly Gly Leu Gly Ser
                85                  90                  95

Gln Gly Thr Ser Gly Arg Gly Gly Leu Gly Gly Gln Gly Ala Gly Ala
            100                 105                 110

Ala Ala Ala Ala Gly Gly Ala Gly Gln Gly Gly Tyr Gly Gly Leu Gly
        115                 120                 125

Ser Gln Gly Thr Ala Ser Gly Arg Gly Gly Leu Gly Gly Gln Gly Ala
130                 135                 140

Gly Ala Ala Ala Ala Gly Gly Ala Gly Gln Gly Gly Tyr Gly Gly
145                 150                 155                 160

Leu Gly Ser Gln Gly Thr Ala Ser Gly Arg Gly Gly Leu Gly Gly Gln
                165                 170                 175

Gly Ala Gly Ala Ala Ala Ala Gly Gly Ala Gly Gln Gly Gly Tyr
            180                 185                 190

Gly Gly Leu Gly Ser Gln Gly Thr Ala Ser Gly Arg Gly Gly Leu Gly
        195                 200                 205

Gly Gln Gly Ala Gly Ala Ala Ala Ala Gly Gly Ala Gly Gln Gly
210                 215                 220

Gly Tyr Gly Gly Leu Gly Ser Gln Gly Thr Ala Ser Gly Arg Gly Gly
225                 230                 235                 240

Leu Gly Gly Gln Gly Ala Gly Ala Ala Ala Ala Gly Gly Ala Gly
                245                 250                 255

Gln Gly Gly Tyr Gly Gly Leu Gly Ser Gln Gly Thr Ala Ser Gly Arg
            260                 265                 270

Gly Gly Leu Gly Gly Gln Gly Ala Gly Ala Ala Ala Ala Gly Gly
        275                 280                 285

Ala Gly Gln Gly Gly Tyr Gly Gly Leu Gly Ser Gln Gly Thr Ala Ser
290                 295                 300

Gly Arg Gly Gly Leu Gly Gly Gln Gly Ala Gly Ala Ala Ala Ala
305                 310                 315                 320

Gly Gly Ala Gly Gln Gly Gly Tyr Gly Gly Leu Gly Ser Gln Gly Thr
                325                 330                 335

Ala Ser Gly Arg Gly Gly Leu Gly Gly Gln Gly Ala Gly Ala Ala
            340                 345                 350

Ala Ala Gly Gly Ala Gly Gln Gly Gly Tyr Gly Gly Leu Gly Ser Gln
        355                 360                 365

Gly Thr Ala Ser Gly Arg Gly Gly Leu Gly Gly Gln Gly Ala Gly Ala
370                 375                 380
```

Ala Ala Ala Ala Gly Gly Ala Gly Gln Gly Gly Tyr Gly Gly Leu Gly
385                 390                 395                 400

Ser Gln Gly Thr Ala Ser Gly Arg Gly Gly Leu Gly Gly Gln Gly Ala
            405                 410                 415

Gly Ala Ala Ala Ala Gly Gly Ala Gly Gln Gly Gly Tyr Gly Gly
        420                 425                 430

Leu Gly Ser Gln Gly Thr Ala Ser Gly Arg Gly Gly Leu Gly Gly Gln
        435                 440                 445

Gly Ala Gly Ala Ala Ala Ala Gly Gly Ala Gly Gln Gly Gly Tyr
    450                 455                 460

Gly Gly Leu Gly Ser Gln Gly Thr Ala Ser Gly Arg Gly Gly Leu Gly
465                 470                 475                 480

Gly Gln Gly Ala Gly Ala Ala Ala Ala Gly Gly Ala Gly Gln Gly
            485                 490                 495

Gly Tyr Gly Gly Leu Gly Ser Gln Gly Thr Ser Gly Ser Ala Arg Ala
            500                 505                 510

Arg

<210> SEQ ID NO 17
<211> LENGTH: 1208
<212> TYPE: DNA
<213> ORGANISM: Artificial sequence
<220> FEATURE:
<223> OTHER INFORMATION: Resilin 17 elastic repeats including the
      native putative chitin binding domain (Res-CHBD) polynucleotide
      sequence

<400> SEQUENCE: 17
ccatgggacc ggagccacca gttaactcgt atctacctcc gtccgatagc tatggagcac      60
cgggtcagag tggtcccggc ggcaggccgt cggattccta tggagctcct ggtggtggaa    120
acggtggacg gccctcagac agctatggcg ctccaggcca gggtcaagga cagggacaag    180
gacaaggtgg atatgcaggc aagccctcag ataccatgg agctcctggt ggtggaaatg     240
gcaacggagg tcgtccatcg agcagctatg gcgctcctgg cggtggaaac ggtggtcgtc    300
cttcggatac ctacggtgct cctggtggcg gaaatggtgg acgccatcg gacacttatg     360 gtgctcctgg tggtggtgga atggcaacg gcggacgacc ttcaagcagc tatggagctc    420
ctggtcaagg acaaggcaac ggaaatggcg gtcgctcatc gagcagctat ggtgctcctg    480
gcggtggaaa cggcggtcgt ccttcggata cctacggtgc tcccggtggt ggaaacggtg    540
gtcgtccttc ggatacttac ggcgctcctg gtggcggcaa taatggcggt cgtccctcaa    600
gcagctacgg cgctcctggt ggtggaaacg gtggtcgtcc atctgacacc tatggcgctc    660
ctggtggcgg taacggaaac ggcagcgtg tcgtccttc aagcagctat ggagctcctg     720
gtcagggcca aggtggattt ggtggtcgtc catcggactc ctatggtgct cctggtcaga    780
accaaaaacc atcagattca tatggcgccc ctggtagcgg caatggcaac ggcggacgtc    840
cttcgagcag ctatggagct ccaggctcag gacctgtgg ccgaccctcc gactcctacg     900
gacccccagc ttctggatcg ggagcaggtg cgctggagg cagtggaccc ggcggcgctg    960
actacgataa cgatgagccc gccaagtacg aatttaatta ccaggttgag acgcgcccca   1020
gcggactctc gttcgggcat tcagagatgc gcgacggtga cttcaccacc ggccagtaca    1080
atgtcctgtt gcccgacgga aggaagcaaa ttgtggagta tgaagccgac cagcagggct    1140
accggccaca gatccgctac gaaggcgatg ccaacgatgg cagtggtccc agcggtcctt    1200
aaggatcc                                                              1208

```
<210> SEQ ID NO 18
<211> LENGTH: 1584
<212> TYPE: DNA
<213> ORGANISM: Artificial sequence
<220> FEATURE:
<223> OTHER INFORMATION: Clostridium cellulovorans CBD (CBDclos) fused
      to Resilin 17 elastic repeats (CBD-resilin) polynucleotide
      sequence

<400> SEQUENCE: 18
gattgtgagc ggataacaat tcccctctag aaataatttt gtttaacttt aagaaggaga     60
tataccatgg cagcgacatc atcaatgtca gttgaatttt acaactctaa caaagcagca    120
caaacaaact caattacacc aataatcaaa attactaaca cagctgacag tgatttaaat    180
ttaaatgacg taaaagttag atattattac acaagtgatg gtacacaagg acaaactttc    240
tggggtgatc atgctggtgc attattagga aatagctatg ttgataacac tggcaaagtg    300
acagcaaact tcgttaaaga aacagcaagc ccaacatcaa cctatgatac atatgttgaa    360
tttggatttg caagcggagc agctactctt aaaaaaggac aatttataac tattcaagga    420
agaataacaa aatcagactg gtcaaactac gctcagacaa tgactattc atttgatgca    480 agtagttcaa caccagttgt aaatccaaaa gttacaggat ataggtgg agctaaagta    540 cttggtacag caccaggtcc agatgtacca tcttcaataa ttaatcctac ttctgcaaca    600
tttgatccgg agccaccagt taactcgtat ctacctccgt ccgatagcta tggagcaccg    660
ggtcagagtg gtcccggcgg caggccgtcg gattcctatg agctcctgg tggtggaaac    720 ggtgacggc cctcagacag ctatggcgct ccaggccagg tcaaggaca gggacaagga    780 caaggtggat atgcaggcaa gccctcagat acctatggag ctcctggtgg tggaaatggc    840
aacggaggtc gtccatcgag cagctatggc gctcctggcg gtggaaacgg tggtcgtcct    900
tcggatacct acggtgctcc tggtggcgga atggtggac gcccatcgga cacttatggt    960
gctcctggtg gtggtggaaa tggcaacggc ggacgacctt caagcagcta tggagctcct   1020
ggtcaaggac aaggcaacgg aaatggcggt cgctcatcga gcagctatgg tgctcctggc   1080 ggtgaaacg gcggtcgtcc ttcggatacc tacggtgctc ccggtggtgg aaacggtggt   1140
cgtccttcgg atacttacgg cgctcctggt ggcggcaata tggcggtcg tccctcaagc   1200 agctacggcg ctcctggtgg tggaaacggt ggtcgtccat ctgacaccta tggcgctcct   1260
ggtggcggta acggaaacgg cagcggtggt cgtccttcaa gcagctatgg agctcctggt   1320
cagggccaag gtggatttgg tggtcgtcca tcggactcct atggtgctcc tggtcagaac   1380
caaaaaccat cagattcata tggcgcccct ggtagcggca atggcaacgg cggacgtcct   1440
tcgagcagct atggagctcc aggctcagga cctggtggcc gaccctccga ctcctacgga   1500
cccccagctt ctggatcggg agcaggtggc gctggaggca gtggacccgg cggcgctgac   1560
tacgataacg atgagtaagg atcc                                          1584

<210> SEQ ID NO 19
<211> LENGTH: 1504
<212> TYPE: DNA
<213> ORGANISM: Artificial sequence
<220> FEATURE:
<223> OTHER INFORMATION: Resilin fused to CBD through a linker coding
      sequence

<400> SEQUENCE: 19
ccatgggacc ggagccacca gttaactcgt atctacctcc gtccgatagc tatggagcac     60
cgggtcagag tggtcccggc ggcaggccgt cggattccta tggagctcct ggtggtggaa    120
```

| | |
|---|---|
| acggtggacg gccctcagac agctatggcg ctccaggcca gggtcaagga cagggacaag | 180 |
| gacaaggtgg atatgcaggc aagccctcag atacctatgg agctcctggt ggtggaaatg | 240 |
| gcaacggagg tcgtccatcg agcagctatg gcgctcctgg cggtggaaac ggtggtcgtc | 300 |
| cttcggatac ctacggtgct cctggtggcg gaaatggtgg acgccatcg gacacttatg | 360 |
| gtgctcctgg tggtggtgga atggcaacg gcggacgacc ttcaagcagc tatggagctc | 420 |
| ctggtcaagg acaaggcaac ggaaatggcg gtcgctcatc gagcagctat ggtgctcctg | 480 |
| gcggtggaaa cggcggtcgt ccttcggata cctacggtgc tcccggtggt ggaaacggtg | 540 |
| gtcgtccttc ggatacttac ggcgctcctg gtggcggcaa taatggcggt cgtccctcaa | 600 |
| gcagctacgg cgctcctggt ggtggaaacg gtggtcgtcc atctgacacc tatggcgctc | 660 |
| ctggtggcgt aacggaaac ggcagcgtg gtcgtccttc aagcagctat ggagctcctg | 720 |
| gtcagggcca aggtggattt ggtggtcgtc catcggactc ctatggtgct cctggtcaga | 780 |
| accaaaaacc atcagattca tatgcgcccc tggtagcgg caatggcaac ggcggacgtc | 840 |
| cttcgagcag ctatggagct ccaggctcag gacctggtgg ccgaccctcc gactcctacg | 900 |
| gaccccagc ttctggatcg ggagcaggt gcgctgagg cagtggaccc ggcggcgctg | 960 |
| actacgataa cgatgagggg atccccgacc ccggcatggc agcgacatca tcaatgtcag | 1020 |
| ttgaatttta caactctaac aaatcagcac aaacaaactc aattcacca ataatcaaaa | 1080 |
| ttactaacac atctgacagt gatttaaatt taaatgacgt aaaagttaga tattattaca | 1140 |
| caagtgatgg tacacaagga caaactttct ggtgtgacca tgctggtgca ttattaggaa | 1200 |
| atagctatgt tgataacact agcaaagtga cagcaaactt cgttaaagaa acagcaagcc | 1260 |
| caacatcaac ctatgataca tatgttgaat ttggatttgc aagcggacga gctactctta | 1320 |
| aaaaaggaca atttataact attcaaggaa gaataacaaa atcagactgg tcaaactaca | 1380 |
| ctcaaacaaa tgactattca tttgatgcaa gtagttcaac accagttgta aatccaaaag | 1440 |
| ttacaggata tataggtgga gctaaagtac ttggtacagc accataggat cgatccagat | 1500 |
| gtac | 1504 |

<210> SEQ ID NO 20
<211> LENGTH: 1523
<212> TYPE: DNA
<213> ORGANISM: Artificial sequence
<220> FEATURE:
<223> OTHER INFORMATION: CBD-resilin fusion construct, codon optimized for expression in plants

<400> SEQUENCE: 20

| | |
|---|---|
| caattggcag cgacatcatc aatgtcagtt gaattttaca actctaacaa agcagcacaa | 60 |
| acaaactcaa ttcaccaat aatcaaaatt actaacacag ctgacagtga tttaaattta | 120 |
| aatgacgtaa aagttagata ttattacaca agtgatggta cacaaggaca aactttctgg | 180 |
| ggtgatcatg ctggtgcatt attaggaaat agctatgttg ataacactgg caaagtgaca | 240 |
| gcaaacttcg ttaaagaaac agcaagccca acatcaacct atgatacata tgttgaattt | 300 |
| ggatttgcaa gcggagcagc tactcttaaa aaaggacaat ttataactat tcaaggaaga | 360 |
| ataacaaaat cagactggtc aaactacgct cagacaaatg actattcatt tgatgcaagt | 420 |
| agttcaacac cagttgtaaa tccaaaagtt acaggatata taggtggagc taaagtactt | 480 |
| ggtacagcac caggtccaga tgtaccatct tcaataatta atcctacttc tgcaacattt | 540 |
| gatccggagc accagttaa ctcgtatcta cctccgtccg atagctatgg agcaccgggt | 600 |
| cagagtggtc ccggcggcag gccgtcggat tcctatggag ctcctggtgg tggaaacggt | 660 |

```
ggacggccct cagacagcta tggcgctcca ggccagggtc aaggacaggg acaaggacaa      720
ggtggatatg caggcaagcc ctcagatacc tatggagctc ctggtggtgg aaatggcaac      780
ggaggtcgtc catcgagcag ctatggcgct cctggcggtg aaacggtggt cgtccttcg      840 gatacctacg gtgctcctgg tggcggaaat ggtggacgcc catcggacac ttatggtgct      900
cctggtggtg gtggaaatgg caacggcgga cgaccttcaa gcagctatgg agctcctggt      960
caaggacaag gcaacggaaa tggcggtcgc tcatcgagca gctatggtgc tcctggcggt     1020
ggaaacggcg tcgtccttc ggatacctac ggtgctcccg gtggtggaaa cggtggtcgt     1080
ccttcggata cttacggcgc tcctggtggc ggcaataatg gcggtcgtcc ctcaagcagc     1140
tacggcgctc tggtggtgg aaacggtggt cgtccatctg acacctatgg cgctcctggt     1200
ggcggtaacg gaaacggcag cggtggtcgt ccttcaagca gctatggagc tcctggtcag     1260
ggccaaggtg gatttggtgg tcgtccatcg gactcctatg gtgctcctgg tcagaaccaa     1320
aaaccatcag attcatatgg cgcccctggt agcggcaatg gcaacggcgg acgtccttcg     1380
agcagctatg gagctccagg ctcaggacct ggtggccgac cctccgactc ctacggaccc     1440
ccagcttctg gatcgggagc aggtggcgct ggaggcagtg gaccccggcgg cgctgactac     1500 gataacgatg agtaagcggc cgc                                             1523

<210> SEQ ID NO 21
<211> LENGTH: 1492
<212> TYPE: DNA
<213> ORGANISM: Artificial sequence
<220> FEATURE:
<223> OTHER INFORMATION: Resilin-CBD fusion construct, codon optimized
      for expression in plants

<400> SEQUENCE: 21
caattgccgg agccaccagt taactcgtat ctacctccgt ccgatagcta tggagcaccg       60
ggtcagagtg gtcccggcgg caggccgtcg gattcctatg gagctcctgg tggtggaaac      120
ggtggacggc cctcagacag ctatggcgct ccaggccagg gtcaaggaca gggacaagga      180
caaggtggat atgcaggcaa gccctcagat acctatggag ctcctggtgg tggaaatggc      240
aacggaggtc gtccatcgag cagctatggc gctcctggcg gtggaaacgg tggtcgtcct      300
tcggatacct acggtgctcc tggtggcgga atggtggac gcccatcgga cacttatggt      360
gctcctggtg gtggtggaaa tggcaacggc ggacgacctt caagcagcta tggagctcct      420
ggtcaaggac aaggcaacgg aaatggcggt cgctcatcga gcagctatgg tgctcctggc      480
ggtggaaacg gcgtcgtcc ttcggatacc tacggtgctc ccggtggtgg aaacggtggt      540
cgtccttcgg atacttacgg cgctcctggt ggcggcaata atggcggtcg tccctcaagc      600
agctacggcg ctcctggtgg tggaaacggt ggtcgtccat ctgacaccta tggcgctcct      660
ggtggcggta acgaaacgg cagcggtggt cgtccttcaa gcagctatgg agctcctggt      720
cagggccaag gtggatttgg tggtcgtcca tcggactcct atggtgctcc tggtcagaac      780
caaaaaccat cagattcata tggcgcccct ggtagcggca atggcaacgg cggacgtcct      840
tcgagcagct atggagctcc aggctcagga cctggtggcc gaccctccga ctcctacgga      900 ccccagctt ctggatcggg agcaggtggc gctggaggca gtggacccgg cggcgctgac      960
tacgataacg atgaggggat ccccgacccc ggcatgcag cgacatcatc aatgtcagtt     1020 gaatttttaca actctaacaa atcagcacaa acaaactcaa ttacaccaat aatcaaaatt     1080
actaacacat ctgacagtga tttaaattta aatgacgtaa aagttagata ttattacaca     1140
agtgatggta cacaaggaca aactttctgg tgtgaccatg ctggtgcatt attaggaaat     1200
```

| | |
|---|---|
| agctatgttg ataacactag caaagtgaca gcaaacttcg ttaaagaaac agcaagccca | 1260 |
| acatcaacct atgatacata tgttgaattt ggatttgcaa gcggacgagc tactcttaaa | 1320 |
| aaaggacaat ttataactat tcaaggaaga ataacaaaat cagactggtc aaactacact | 1380 |
| caaacaaatg actattcatt tgatgcaagt agttcaacac cagttgtaaa tccaaaagtt | 1440 |
| acaggatata taggtggagc taaagtactt ggtacagcac catagcggcc gc | 1492 |

<210> SEQ ID NO 22
<211> LENGTH: 1208
<212> TYPE: DNA
<213> ORGANISM: Artificial sequence
<220> FEATURE:
<223> OTHER INFORMATION: Resilin including the native putative chitin
binding domain, codon optimized for expression in plants,
polynucleotide sequence

<400> SEQUENCE: 22

| | |
|---|---|
| caattgccgg agccaccagt taactcgtat ctacctccgt ccgatagcta tggagcaccg | 60 |
| ggtcagagtg gtcccggcgg caggccgtcg gattcctatg gagctcctgg tggtggaaac | 120 |
| ggtggacggc cctcagacag ctatggcgct ccaggccagg gtcaaggaca gggacaagga | 180 |
| caaggtggat atgcaggcaa gccctcagat acctatggag ctcctggtgg tggaaatggc | 240 |
| aacggaggtc gtccatcgag cagctatggc gctcctggcg gtggaaacgg tggtcgtcct | 300 |
| tcggatacct acggtgctcc tggtggcgga aatggtggac gcccatcgga cacttatggt | 360 |
| gctcctggtg gtggtggaaa tggcaacggc ggacgacctt caagcagcta tggagctcct | 420 |
| ggtcaaggac aaggcaacgg aaatggcggt cgctcatcga gcagctatgg tgctcctggc | 480 |
| ggtgaaacgg gcggtcgtcc ttcggatacc tacggtgctc cggtggtgg aaacggtggt | 540 |
| cgtccttcgg atacttacgg cgctcctggt ggcggcaata atggcggtcg tccctcaagc | 600 |
| agctacggcg ctcctggtgg tggaaacggt ggtcgtccat ctgacaccta tggcgctcct | 660 |
| ggtggcggta acggaaacgg cagcggtggt cgtccttcaa gcagctatgg agctcctggt | 720 |
| cagggccaag gtggatttgg tggtcgtcca tcggactcct atggtgctcc tggtcagaac | 780 |
| caaaaaccat cagattcata tggcgcccct ggtagcggca atggcaacgg cggacgtcct | 840 |
| tcgagcagct atggagctcc aggctcagga cctggtggcc gaccctccga ctcctacgga | 900 |
| ccccagcctt ctggatcggg agcaggtggc gctgaaggca gtggacccgg cggcgctgac | 960 |
| tacgataacg atgagcccgc caagtacgaa tttaattacc aggttgagga cgcgcccagc | 1020 |
| ggactctcgt tcgggcattc agagatgcgc gacggtgact tcaccaccgg ccagtacaat | 1080 |
| gtcctgttgc ccgacggaag gaagcaaatt gtggagtatg aagccgacca gcagggctac | 1140 |
| cggccacaga tccgctacga aggcgatgcc aacgatggca gtggtcccag cggtccttaa | 1200 |
| gcggccgc | 1208 |

<210> SEQ ID NO 23
<211> LENGTH: 1485
<212> TYPE: DNA
<213> ORGANISM: Artificial sequence
<220> FEATURE:
<223> OTHER INFORMATION: 15 sps spider silk synthetic gene

<400> SEQUENCE: 23

| | |
|---|---|
| agcggtcgtg gcggtctggg tggccagggt gcaggtgctg ctgcggcagc aggcggtgct | 60 |
| ggccaaggtg gctacggtgg cctgggttct caggtgtacta gcggtcgtgg cggtctgggt | 120 |
| ggccagggtg caggtgctgc tgcggcagca ggcggtgctg gccaaggtgg ctacggtggc | 180 |

```
ctgggttctc agggtactag cggtcgtggc ggtctgggtg gccagggtgc aggtgctgct    240
gcggcagcag gcggtgctgg ccaaggtggc tacggtggcc tgggttctca gggtactagc    300
ggtcgtggcg gtctgggtgg ccagggtgca ggtgctgctg cggcagcagg cggtgctggc    360
caaggtggct acggtggcct gggttctcag ggtactagcg gtcgtggcgg tctgggtggc    420
cagggtgcag gtgctgctgc ggcagcaggc ggtgctggcc aaggtggcta cggtggcctg    480
ggttctcagg gtactagcgg tcgtggcggt ctgggtggcc agggtgcagg tgctgctgcg    540
gcagcaggcg gtgctggcca aggtggctac ggtggcctgg gttctcaggg tactagcggt    600
cgtggcggtc tgggtggcca gggtgcaggt gctgctgcgg cagcaggcgg tgctggccaa    660
ggtggctacg gtggcctggg ttctcagggt actagcggtc gtggcggtct gggtggccag    720
ggtgcaggtg ctgctgcggc agcaggcggt gctggccaag gtggctacgg tggcctgggt    780
tctcagggta ctagcggtcg tggcggtctg ggtggccagg gtgcaggtgc tgctgcggca    840
gcaggcggtg ctggccaagg tggctacggt ggcctgggtt ctcagggtac tagcggtcgt    900
ggcggtctgg gtggccaggg tgcaggtgct gctgcgcag caggcggtgc tggccaaggt    960
ggctacggtg gcctgggttc tcagggtact agcggtcgtg gcggtctggg tggccagggt    1020
gcaggtgctg ctgcggcagc aggcggtgct ggccaaggtg ctacggtgg cctgggttct    1080 cagggtacta gcggtcgtgg cggtctgggt ggccagggtg caggtgctgc tgcggcagca    1140
ggcggtgctg gccaaggtgg ctacggtggc ctgggttctc agggtactag cggtcgtggc    1200
ggtctgggtg ccagggtgc aggtgctgct gcggcagcag gcggtgctgg ccaaggtggc    1260
tacggtggcc tgggttctca gggtactagc ggtcgtggcg gtctgggtgg ccagggtgca    1320
ggtgctgctg cggcagcagg cggtgctggc caaggtggct acggtggcct gggttctcag    1380
ggtactagcg gtcgtggcgg tctgggtggc cagggtgcag gtgctgctgc ggcagcaggc    1440
ggtgctggcc aaggtggcta cggtggcctg ggttctcagg gtact          1485

<210> SEQ ID NO 24
<211> LENGTH: 2034
<212> TYPE: DNA
<213> ORGANISM: Artificial sequence
<220> FEATURE:
<223> OTHER INFORMATION: 15 sps spider silk fused to CBD polynucleotide
      sequence

<400> SEQUENCE: 24
agcggtcgtg gcggtctggg tggccagggt gcaggtgctg ctgcggcagc aggcggtgct     60
ggccaaggtg gctacggtgg cctgggttct cagggtacta gcggtcgtgg cggtctgggt    120
ggccagggtg caggtgctgc tgcggcagca ggcggtgctg gccaaggtgg ctacggtggc    180
ctgggttctc agggtactag cggtcgtggc ggtctgggtg gccagggtgc aggtgctgct    240
gcggcagcag gcggtgctgg ccaaggtggc tacggtggcc tgggttctca gggtactagc    300
ggtcgtggcg gtctgggtgg ccagggtgca ggtgctgctg cggcagcagg cggtgctggc    360
caaggtggct acggtggcct gggttctcag gtactagcg gtcgtggcgg tctgggtggc    420
cagggtgcag gtgctgctgc ggcagcaggc ggtgctggcc aaggtggcta cggtggcctg    480
ggttctcagg gtactagcgg tcgtggcggt ctgggtggcc agggtgcagg tgctgctgcg    540
gcagcaggcg gtgctggcca aggtggctac ggtggcctgg gttctcaggg tactagcggt    600
cgtggcggtc tgggtggcca gggtgcaggt gctgctgcgg cagcaggcgg tgctggccaa    660
ggtggctacg gtggcctggg ttctcagggt actagcggtc gtggcggtct gggtggccag    720
ggtgcaggtg ctgctgcggc agcaggcggt gctggccaag gtggctacgg tggcctgggt    780
```

```
tctcagggta ctagcggtcg tggcggtctg ggtggccagg gtgcaggtgc tgctgcggca      840
gcaggcggtg ctggccaagg tggctacggt ggcctgggtt ctcagggtac tagcggtcgt      900
ggcggtctgg gtggccaggg tgcaggtgct gctgcggcag caggcggtgc tggccaaggt      960
ggctacggtg gcctgggttc tcagggtact agcggtcgtg gcggtctggg tggccagggt     1020
gcaggtgctg ctgcggcagc aggcggtgct ggccaaggtg gctacggtgg cctgggttct     1080
cagggtacta gcggtcgtgg cggtctgggt ggccagggtg caggtgctgc tgcggcagca     1140
ggcggtgctg gccaaggtgg ctacggtggc ctgggttctc agggtactag cggtcgtggc     1200
ggtctgggtg ccagggtgc aggtgctgct gcggcagcag gcggtgctgg ccaaggtggc     1260
tacggtggcc tgggttctca gggtactagc ggtcgtggcg gtctgggtgg ccagggtgca     1320
ggtgctgctg cggcagcagg cggtgctggc caaggtggct acggtggcct gggttctcag     1380
ggtactagcg gtcgtggcgg tctgggtggc cagggtgcag gtgctgctgc ggcagcaggc     1440
ggtgctggcc aaggtggcta cggtggcctg ggttctcagg gtactagtat ggcagcgaca     1500
tcatcaatgt cagttgaatt ttacaactct aacaaagcag cacaaacaaa ctcaattaca     1560
ccaataatca aaattactaa cacagctgac agtgatttaa atttaaatga cgtaaaagtt     1620
agatattatt acacaagtga tggtacacaa ggacaaactt ctggggtga tcatgctggt     1680 gcattattag aaatagcta tgttgataac actggcaaag tgacagcaaa cttcgttaaa     1740
gaaacagcaa gcccaacatc aacctatgat acatatgttg aatttggatt tgcaagcgga     1800
gcagctactc ttaaaaaagg acaatttata actattcaag gaagaataac aaaatcagac     1860 tggtcaaaact acgctcagac aaatgactat tcatttgatg caagtagttc aacaccagtt     1920
gtaaatccaa aagttacagg atatataggt ggagctaaag tacttggtac agcaccaggt     1980
ccagatgtac catcttcaat aattaatcct acttctgcaa catttgatct cgag           2034

<210> SEQ ID NO 25
<211> LENGTH: 542
<212> TYPE: DNA
<213> ORGANISM: Clostridium cellulovorans
<220> FEATURE:
<221> NAME/KEY: misc_feature
<223> OTHER INFORMATION: Clostridium cellulovorans CBD (CBDclos)
      polynucleotide sequence

<400> SEQUENCE: 25
ccatggcagc gacatcatca atgtcagttg aattttacaa ctctaacaaa gcagcacaaa       60
caaactcaat taccaata atcaaaatta ctaacacagc tgacagtgat ttaaatttaa      120
atgacgtaaa agttagatat tattacacaa gtgatggtac acaaggacaa actttctggg      180
gtgatcatgc tggtgcatta ttaggaaata gctatgttga taacactggc aaagtgacag      240
caaacttcgt taagaaaca gcaagcccaa catcaaccta tgatacatat gttgaatttg      300
gatttgcaag cggagcagct actcttaaaa aaggacaatt tataactatt caaggaagaa      360
taacaaaatc agactggtca aactacgctc agacaaatga ctattcattt gatgcaagta      420
gttcaacacc agttgtaaat ccaaaagtta caggatatat aggtggagct aaagtacttg      480
gtacagcacc aggtccagat gtaccatctt caataattaa tcctacttct gcaacatttg      540
at                                                                    542

<210> SEQ ID NO 26
<211> LENGTH: 39
<212> TYPE: PRT
<213> ORGANISM: Artificial sequence
```

<220> FEATURE:
<223> OTHER INFORMATION: Spider silk repeated unit

<400> SEQUENCE: 26

Gly Pro Gly Gly Gln Gly Pro Tyr Gly Pro Gly Ala Ser Ala Ala Ala
1               5                   10                  15

Ala Ala Ala Gly Gly Tyr Gly Pro Gly Tyr Gly Gln Gln Gly Pro Gly
            20                  25                  30

Gln Gln Gly Pro Gly Gln Gln
        35

<210> SEQ ID NO 27
<211> LENGTH: 734
<212> TYPE: DNA
<213> ORGANISM: Artificial sequence
<220> FEATURE:
<223> OTHER INFORMATION: Synthetic spider silk repeating unit (GENEART)
      polynucleotide sequence

<400> SEQUENCE: 27
gaattcaggc ctccaggcgc ccatatggct gctacttctt ctatgtctgt tgagttctac      60
aactccaaca aggctgctca gaccaactct attactccaa tcattaagat taccaacact    120
gccgattccg atttgaactt gaacgatgtt aaagttcgtt actactacac ttccgatgga    180
actcaaggtc aaactttctg gggtgatcat gctaccatgg cttctatgac tggtggtcag    240
cagatgggta gaattggatc cccaccaggt cccgggccag gtggtcaagg accttatggt    300
ccaggagctt ctgcagctgc tgcagccgct ggaggttatg gaccaggttc tggtcaacaa    360
ggtccaggac aacagggtcc tggtcaacaa gccggctctt ctgttccagt tgcttccgct    420
gttgcttcta gattgtcctc tccagctgct tcttccagag tttcctctgc tgtttcttct    480
ttggtttctt ctggtccaac taagcacgct gctttgtcca acactatttc ttccgttgtt    540
tctcaggttt ccgcttccaa tcctggtctt tctggttgtg atgttttggt tcaggctttg    600
ttggaagtgg tgtctgcttt ggtgtctatc ttgggctctt cctctattgg tcaaatcaac    660
tacggtgcct ctgctcagta tactcagatg gttggccaat ctgttgctca agctctagca    720
gcggccgcaa gctt                                                      734

<210> SEQ ID NO 28
<211> LENGTH: 2411
<212> TYPE: DNA
<213> ORGANISM: Artificial sequence
<220> FEATURE:
<223> OTHER INFORMATION: CBDclos fused to 12sps Spider silk
      polynucleotide sequence

<400> SEQUENCE: 28
gaattcaggc ctccaggcgc ccatatggct gctacttctt ctatgtctgt tgagttctac      60
aactccaaca aggctgctca gaccaactct attactccaa tcattaagat taccaacact    120
gccgattccg atttgaactt gaacgatgtt aaagttcgtt actactacac ttccgatgga    180
actcaaggtc aaactttctg gggtgatcat gctggtgcat tattaggaaa tagctatgtt    240
gataacactg gcaaagtgac agcaaacttc gttaaagaaa cagcaagccc aacatcaacc    300
tatgatacat atgttgaatt tggatttgca agcggagcag ctactcttaa aaaggacaa     360 tttataacta ttcaaggaag aataacaaaa tcagactggt caaactacgc tcagacaaat    420
gactattcat ttgatgcaag tagttcaaca ccagttgtaa atccaaaagt tacaggatat    480
ataggtggag ctaaagtact tggtacagca ccaggtccag atgtaccatc ttcaataatt    540

```
aatcctactt ctgcaacatt tgatcccggt accatggctt ctatgactgg tggtcagcag    600
atgggtagaa ttggatcccc accaggtccc gggccaggtg gtcaaggacc ttatggtcca    660
ggagcttctg cagctgctgc agccgctgga ggttatggac caggttctgg tcaacaaggt    720
ccaggacaac agggtcctgg tcaacaagcc gggccaggtg gtcaaggacc ttatggtcca    780
ggagcttctg cagctgctgc agccgctgga ggttatggac caggttctgg tcaacaaggt    840
ccaggacaac agggtcctgg tcaacaagcc gggccaggtg gtcaaggacc ttatggtcca    900
ggagcttctg cagctgctgc agccgctgga ggttatggac caggttctgg tcaacaaggt    960
ccaggacaac agggtcctgg tcaacaagcc gggccaggtg gtcaaggacc ttatggtcca   1020
ggagcttctg cagctgctgc agccgctgga ggttatggac caggttctgg tcaacaaggt   1080
ccaggacaac agggtcctgg tcaacaagcc gggccaggtg gtcaaggacc ttatggtcca   1140
ggagcttctg cagctgctgc agccgctgga ggttatggac caggttctgg tcaacaaggt   1200
ccaggacaac agggtcctgg tcaacaagcc gggccaggtg gtcaaggacc ttatggtcca   1260
ggagcttctg cagctgctgc agccgctgga ggttatggac caggttctgg tcaacaaggt   1320
ccaggacaac agggtcctgg tcaacaagcc gggccaggtg gtcaaggacc ttatggtcca   1380
ggagcttctg cagctgctgc agccgctgga ggttatggac caggttctgg tcaacaaggt   1440
ccaggacaac agggtcctgg tcaacaagcc gggccaggtg gtcaaggacc ttatggtcca   1500
ggagcttctg cagctgctgc agccgctgga ggttatggac caggttctgg tcaacaaggt   1560
ccaggacaac agggtcctgg tcaacaagcc gggccaggtg gtcaaggacc ttatggtcca   1620
ggagcttctg cagctgctgc agccgctgga ggttatggac caggttctgg tcaacaaggt   1680
ccaggacaac agggtcctgg tcaacaagcc gggccaggtg gtcaaggacc ttatggtcca   1740
ggagcttctg cagctgctgc agccgctgga ggttatggac caggttctgg tcaacaaggt   1800
ccaggacaac agggtcctgg tcaacaagcc gggccaggtg gtcaaggacc ttatggtcca   1860
ggagcttctg cagctgctgc agccgctgga ggttatggac caggttctgg tcaacaaggt   1920
ccaggacaac agggtcctgg tcaacaagcc gggccaggtg gtcaaggacc ttatggtcca   1980
ggagcttctg cagctgctgc agccgctgga ggttatggac caggttctgg tcaacaaggt   2040
ccaggacaac agggtcctgg tcaacaagcc ggctcttctg ttccagttgc ttccgctgtt   2100
gcttctagat tgtcctctcc agctgcttct tccagagttt cctctgctgt ttcttctttg   2160
gtttcttctg gtccaactaa gcacgctgct ttgtccaaca ctatttcttc cgttgtttct   2220
caggtttccg cttccaatcc tggtctttct ggttgtgatg ttttggttca ggctttgttg   2280
gaagtggtgt ctgctttggt gtctatcttg ggctcttcct ctattggtca aatcaactac   2340
ggtgcctctg ctcagtatac tcagatggtt ggccaatctg ttgctcaagc tctagcagcg   2400
gccgcaagct t                                                        2411
```

<210> SEQ ID NO 29
<211> LENGTH: 2411
<212> TYPE: DNA
<213> ORGANISM: Artificial sequence
<220> FEATURE:
<223> OTHER INFORMATION: Spider silk 6sps-CBD-6sps construct
      polynucleotide sequence

<400> SEQUENCE: 29

```
gaattcaggg ggccaggtgg tcaaggacct tatggtccag gagcttctgc agctgctgca     60
gccgctggag gttatggacc aggttctggt caacaaggtc caggacaaca gggtcctggt    120
```

| | |
|---|---|
| caacaagccg ggccaggtgg tcaaggacct tatggtccag gagcttctgc agctgctgca | 180 |
| gccgctggag gttatggacc aggttctggt caacaaggtc caggacaaca gggtcctggt | 240 |
| caacaagccg ggccaggtgg tcaaggacct tatggtccag gagcttctgc agctgctgca | 300 |
| gccgctggag gttatggacc aggttctggt caacaaggtc caggacaaca gggtcctggt | 360 |
| caacaagccg ggccaggtgg tcaaggacct tatggtccag gagcttctgc agctgctgca | 420 |
| gccgctggag gttatggacc aggttctggt caacaaggtc caggacaaca gggtcctggt | 480 |
| caacaagccg ggccaggtgg tcaaggacct tatggtccag gagcttctgc agctgctgca | 540 |
| gccgctggag gttatggacc aggttctggt caacaaggtc caggacaaca gggtcctggt | 600 |
| caacaagccg ggccaggtgg tcaaggacct tatggtccag gagcttctgc agctgctgca | 660 |
| gccgctggag gttatggacc aggttctggt caacaaggtc caggacaaca gggtcctggt | 720 |
| caacaagccc ctccaggcgc ccatatggct gctacttctt ctatgtctgt tgagttctac | 780 |
| aactccaaca aggctgctca gaccaactct attactccaa tcattaagat taccaacact | 840 |
| gccgattccg atttgaactt gaacgatgtt aaagttcgtt actactacac ttccgatgga | 900 |
| actcaaggtc aaactttctg gggtgatcat gctggtgcat tattaggaaa tagctatgtt | 960 |
| gataacactg gcaaagtgac agcaaacttc gttaaagaaa cagcaagccc aacatcaacc | 1020 |
| tatgatacat atgttgaatt tggatttgca agcggagcag ctactcttaa aaaggacaa | 1080 |
| tttataacta ttcaaggaag aataacaaaa tcagactggt caaactacgc tcagacaaat | 1140 |
| gactattcat ttgatgcaag tagttcaaca ccagttgtaa atccaaaagt tacaggatat | 1200 |
| ataggtggag ctaaagtact tggtacagca ccaggtccag atgtaccatc ttcaataatt | 1260 |
| aatcctactt ctgcaacatt tgatcccggt accatggctt ctatgactgg tggtcagcag | 1320 |
| atgggtagaa ttggatcccc accaggtccc gggccaggtg gtcaaggacc ttatggtcca | 1380 |
| ggagcttctg cagctgctgc agccgctgga ggttatggac caggttctgg tcaacaaggt | 1440 |
| ccaggacaac agggtcctgg tcaacaagcc gggccaggtg gtcaaggacc ttatggtcca | 1500 |
| ggagcttctg cagctgctgc agccgctgga ggttatggac caggttctgg tcaacaaggt | 1560 |
| ccaggacaac agggtcctgg tcaacaagcc gggccaggtg gtcaaggacc ttatggtcca | 1620 |
| ggagcttctg cagctgctgc agccgctgga ggttatggac caggttctgg tcaacaaggt | 1680 |
| ccaggacaac agggtcctgg tcaacaagcc gggccaggtg gtcaaggacc ttatggtcca | 1740 |
| ggagcttctg cagctgctgc agccgctgga ggttatggac caggttctgg tcaacaaggt | 1800 |
| ccaggacaac agggtcctgg tcaacaagcc gggccaggtg gtcaaggacc ttatggtcca | 1860 |
| ggagcttctg cagctgctgc agccgctgga ggttatggac caggttctgg tcaacaaggt | 1920 |
| ccaggacaac agggtcctgg tcaacaagcc gggccaggtg gtcaaggacc ttatggtcca | 1980 |
| ggagcttctg cagctgctgc agccgctgga ggttatggac caggttctgg tcaacaaggt | 2040 |
| ccaggacaac agggtcctgg tcaacaagcc ggctcttctg ttccagttgc ttccgctgtt | 2100 |
| gcttctagat tgtcctctcc agctgcttct tccagagttt cctctgctgt ttcttctttg | 2160 |
| gtttcttctg tccaactaa gcacgctgct tgtccaaca ctatttcttc cgttgtttct | 2220 |
| caggtttccg cttccaatcc tggtctttct ggttgtgatg ttttggttca ggctttgttg | 2280 |
| gaagtggtgt ctgctttggt gtctatcttg ggctcttcct ctattggtca aatcaactac | 2340 |
| ggtgcctctg ctcagtatac tcagatggtt ggccaatctg ttgctcaagc tctagcagcg | 2400 |
| gccgcaagct t | 2411 |

<210> SEQ ID NO 30
<211> LENGTH: 1017
<212> TYPE: DNA
<213> ORGANISM: Artificial sequence
<220> FEATURE:
<223> OTHER INFORMATION: Rubisco's small subunit cassette including promoter and 5' UTR

<400> SEQUENCE: 30

```
aaatggcgcg ccaagcttag acaaacaccc cttgttatac aaagaatttc gctttacaaa      60
atcaaattcg agaaaataat atatgcacta ataagatca ttcggatcca atctaaccaa      120
ttacgatacg ctttgggtac acttgatttt tgtttcagta gttacatata tcttgtttta    180
tatgctatct ttaaggatct tcactcaaag actatttgtt gatgttcttg atggggctcg    240
gaagatttga tatgatacac tctaatcttt aggagatacc agccaggatt atattcagta    300
agacaatcaa attttacgtg ttcaaactcg ttatcttttc atttaatgga tgagccagaa    360
tctctataga atgattgcaa tcgagaatat gttcggccga tatcccttg ttggcttcaa     420
tattctacat atcacacaag aatcgaccgt attgtaccct ctttccataa aggaacacac    480
agtatgcaga tgcttttttc ccacatgcag taacataggt attcaaaaat ggctaaaaga    540
agttggataa caaattgaca actatttcca tttctgttat ataaatttca caacacacaa    600
aagcccgtaa tcaagagtct gcccatgtac gaaataactt ctattatttg gtattgggcc    660
taagcccagc tcagagtacg tgggggtacc acatatagga aggtaacaaa atactgcaag    720
atagccccat aacgtaccag cctctcctta ccacgaagag ataagatata agacccaccc    780
tgccacgtgt cacatcgtca tggtggttaa tgataaggga ttacatcctt ctatgtttgt    840
ggacatgatg catgtaatgt catgagccac atgatccaat ggccacagga acgtaagaat    900
gtagatagat ttgattttgt ccgttagata gcaaacaaca ttataaaagg tgtgtatcaa    960
tacgaactaa ttcactcatt ggattcatag aagtccattc ctcctaagta tctaaac      1017
```

<210> SEQ ID NO 31
<211> LENGTH: 975
<212> TYPE: DNA
<213> ORGANISM: Artificial sequence
<220> FEATURE:
<223> OTHER INFORMATION: Rubisco's small subunit cassette including 3' UTR and terminator

<400> SEQUENCE: 31

```
aaaaggatcc gcggccgcat aagtttact atttaccaag acttttgaat attaaccttc       60
ttgtaacgag tcggttaaat ttgattgttt agggttttgt attattttt tttggtcttt      120
taattcatca ctttaattcc ctaattgtct gttcatttcg ttgtttgttt ccggatcgat     180
aatgaaatgt aagagatatc atatataaat aataaattgt cgtttcatat ttgcaatctt    240
tttttacaaa cctttaatta attgtatgta tgacattttc ttcttgttat attagggga     300
aataatgtta aataaaagta caaaataaac tacagtacat cgtactgaat aaattaccta    360
gccaaaaagt acacctttcc atatacttcc tacatgaagg cattttcaac attttcaaat    420
aaggaatgct acaaccgcat aataacatcc acaaattttt ttataaaata acatgtcaga    480
cagtgattga aagattttat tatagtttcg ttatcttctt ttctcattaa gcgaatcact    540
acctaacacg tcattttgtg aaatatttt tgaatgtttt tatatagttg tagcattcct     600
cttttcaaat tagggtttgt ttgagatagc atttcagccg gttcatacaa cttaaaagca    660
tactctaatg ctggaaaaaa gactaaaaaa tcttgtaagt tagcgcagaa tattgaccca    720
aattatatac acacatgacc ccatatagag actaattaca cttttaacca ctaataatta    780
```

```
ttactgtatt ataacatcta ctaattaaac ttgtgagttt tgctagaat tattatcata    840 tatactaaaa ggcaggaacg caaacattgc cccggtactg tagcaactac ggtagacgca    900
ttaattgtct atagtggacg cattaattaa ccaaaaccgc ctctttcccc ttcttcttga    960
agcttgagct ctttt                                                     975
```

```
<210> SEQ ID NO 32
<211> LENGTH: 687
<212> TYPE: PRT
<213> ORGANISM: Artificial sequence
<220> FEATURE:
<223> OTHER INFORMATION: 15 sps spider silk fused to CBD

<400> SEQUENCE: 32
```

```
Ser Gly Arg Gly Gly Leu Gly Gly Gln Gly Ala Gly Ala Ala Ala
1               5                   10                  15

Ala Gly Gly Ala Gly Gln Gly Gly Tyr Gly Gly Leu Gly Ser Gln Gly
            20                  25                  30

Thr Ser Gly Arg Gly Gly Leu Gly Gly Gln Gly Ala Gly Ala Ala Ala
        35                  40                  45

Ser Ala Gly Gly Ala Gly Gln Gly Gly Tyr Gly Gly Leu Gly Ser Gln
    50                  55                  60

Gly Thr Ser Gly Arg Gly Gly Leu Gly Gly Gln Gly Ala Gly Ala Ala
65                  70                  75                  80

Ala Ala Ala Gly Gly Ala Gly Gln Gly Gly Tyr Gly Gly Leu Gly Ser
                85                  90                  95

Gln Gly Thr Ser Gly Arg Gly Gly Leu Gly Gly Gln Gly Ala Gly Ala
            100                 105                 110

Ala Ala Ala Ala Gly Gly Ala Gly Gln Gly Gly Tyr Gly Gly Leu Gly
        115                 120                 125

Ser Gln Gly Thr Ala Ser Gly Arg Gly Gly Leu Gly Gly Gln Gly Ala
130                 135                 140

Gly Ala Ala Ala Ala Ala Gly Ala Gly Gln Gly Gly Tyr Gly Gly
145                 150                 155                 160

Leu Gly Ser Gln Gly Thr Ala Ser Gly Arg Gly Gly Leu Gly Gly Gln
            165                 170                 175

Gly Ala Gly Ala Ala Ala Ala Ala Gly Gly Ala Gly Gln Gly Gly Tyr
        180                 185                 190

Gly Gly Leu Gly Ser Gln Gly Thr Ala Ser Gly Arg Gly Gly Leu Gly
    195                 200                 205

Gly Gln Gly Ala Gly Ala Ala Ala Ala Gly Gly Ala Gly Gln Gly
210                 215                 220

Gly Tyr Gly Gly Leu Gly Ser Gln Gly Thr Ala Ser Gly Arg Gly Gly
225                 230                 235                 240

Leu Gly Gly Gln Gly Ala Gly Ala Ala Ala Ala Gly Gly Ala Gly
            245                 250                 255

Gln Gly Gly Tyr Gly Gly Leu Gly Ser Gln Gly Thr Ala Ser Gly Arg
        260                 265                 270

Gly Gly Leu Gly Gly Gln Gly Ala Gly Ala Ala Ala Ala Gly Gly
    275                 280                 285

Ala Gly Gln Gly Gly Tyr Gly Gly Leu Gly Ser Gln Gly Thr Ala Ser
    290                 295                 300

Gly Arg Gly Gly Leu Gly Gly Gln Gly Ala Gly Ala Ala Ala Ala Ala
305                 310                 315                 320
```

```
Gly Gly Ala Gly Gln Gly Gly Tyr Gly Gly Leu Gly Ser Gln Gly Thr
            325                 330                 335

Ala Ser Gly Arg Gly Gly Leu Gly Gly Gln Gly Ala Gly Ala Ala Ala
            340                 345                 350

Ala Ala Gly Gly Ala Gly Gln Gly Gly Tyr Gly Gly Leu Gly Ser Gln
            355                 360                 365

Gly Thr Ala Ser Gly Arg Gly Gly Leu Gly Gly Gln Gly Ala Gly Ala
        370                 375                 380

Ala Ala Ala Ala Gly Gly Ala Gly Gln Gly Gly Tyr Gly Gly Leu Gly
385                 390                 395                 400

Ser Gln Gly Thr Ala Ser Gly Arg Gly Gly Leu Gly Gly Gln Gly Ala
            405                 410                 415

Gly Ala Ala Ala Ala Gly Gly Ala Gly Gln Gly Gly Tyr Gly Gly
            420                 425                 430

Leu Gly Ser Gln Gly Thr Ala Ser Gly Arg Gly Gly Leu Gly Gly Gln
            435                 440                 445

Gly Ala Gly Ala Ala Ala Ala Gly Gly Ala Gly Gln Gly Gly Tyr
            450                 455                 460

Gly Gly Leu Gly Ser Gln Gly Thr Ala Ser Gly Arg Gly Gly Leu Gly
465                 470                 475                 480

Gly Gln Gly Ala Gly Ala Ala Ala Ala Gly Gly Ala Gly Gln Gly
            485                 490                 495

Gly Tyr Gly Gly Leu Gly Ser Gln Gly Thr Ser Met Ala Ala Thr Ser
            500                 505                 510

Ser Met Ser Val Glu Phe Tyr Asn Ser Asn Lys Ala Ala Gln Thr Asn
            515                 520                 525

Ser Ile Thr Pro Ile Ile Lys Ile Thr Asn Thr Ala Asp Ser Asp Leu
            530                 535                 540

Asn Leu Asn Asp Val Lys Val Arg Tyr Tyr Thr Ser Asp Gly Thr
545                 550                 555                 560

Gln Gly Gln Thr Phe Trp Gly Asp His Ala Gly Ala Leu Leu Gly Asn
            565                 570                 575

Ser Tyr Val Asp Asn Thr Gly Lys Val Thr Ala Asn Phe Val Lys Glu
            580                 585                 590

Thr Ala Ser Pro Thr Ser Thr Tyr Asp Thr Tyr Val Glu Phe Gly Phe
            595                 600                 605

Ala Ser Gly Ala Ala Thr Leu Lys Lys Gly Gln Phe Ile Thr Ile Gln
            610                 615                 620

Gly Arg Ile Thr Lys Ser Asp Trp Ser Asn Tyr Ala Gln Thr Asn Asp
625                 630                 635                 640

Tyr Ser Phe Asp Ala Ser Ser Ser Thr Pro Val Val Asn Pro Lys Val
            645                 650                 655

Thr Gly Tyr Ile Gly Gly Ala Lys Val Leu Gly Thr Ala Pro Gly Pro
            660                 665                 670

Asp Val Pro Ser Ser Ile Ile Asn Pro Thr Ser Ala Thr Phe Asp
            675                 680                 685

<210> SEQ ID NO 33
<211> LENGTH: 570
<212> TYPE: PRT
<213> ORGANISM: Artificial sequence
<220> FEATURE:
<223> OTHER INFORMATION: 6His tagged 15sps spider silk polypeptide
```

```
<400> SEQUENCE: 33

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Ser Gly
        35                  40                  45

Arg Gly Gly Leu Gly Gly Gln Gly Ala Gly Ala Ala Ala Ala Gly
    50                  55                  60

Gly Ala Gly Gln Gly Gly Tyr Gly Gly Leu Gly Ser Gln Gly Thr Ser
65                  70                  75                  80

Gly Arg Gly Gly Leu Gly Gly Gln Gly Ala Gly Ala Ala Ala Ser Ala
                85                  90                  95

Gly Gly Ala Gly Gln Gly Gly Tyr Gly Gly Leu Gly Ser Gln Gly Thr
            100                 105                 110

Ser Gly Arg Gly Gly Leu Gly Gly Gln Gly Ala Gly Ala Ala Ala Ala
        115                 120                 125

Ala Gly Gly Ala Gly Gln Gly Gly Tyr Gly Gly Leu Gly Ser Gln Gly
    130                 135                 140

Thr Ser Gly Arg Gly Gly Leu Gly Gly Gln Gly Ala Gly Ala Ala Ala
145                 150                 155                 160

Ala Ala Gly Gly Ala Gly Gln Gly Gly Tyr Gly Gly Leu Gly Ser Gln
                165                 170                 175

Gly Thr Ala Ser Gly Arg Gly Gly Leu Gly Gly Gln Gly Ala Gly Ala
            180                 185                 190

Ala Ala Ala Ala Gly Gly Ala Gly Gln Gly Gly Tyr Gly Gly Leu Gly
        195                 200                 205

Ser Gln Gly Thr Ala Ser Gly Arg Gly Gly Leu Gly Gly Gln Gly Ala
    210                 215                 220

Gly Ala Ala Ala Ala Gly Gly Ala Gly Gln Gly Gly Tyr Gly Gly
225                 230                 235                 240

Leu Gly Ser Gln Gly Thr Ala Ser Gly Arg Gly Gly Leu Gly Gly Gln
                245                 250                 255

Gly Ala Gly Ala Ala Ala Ala Gly Gly Ala Gly Gln Gly Gly Tyr
            260                 265                 270

Gly Gly Leu Gly Ser Gln Gly Thr Ala Ser Gly Arg Gly Gly Leu Gly
        275                 280                 285

Gly Gln Gly Ala Gly Ala Ala Ala Ala Gly Gly Ala Gly Gln Gly
    290                 295                 300

Gly Tyr Gly Gly Leu Gly Ser Gln Gly Thr Ala Ser Gly Arg Gly Gly
305                 310                 315                 320

Leu Gly Gly Gln Gly Ala Gly Ala Ala Ala Ala Gly Gly Ala Gly
                325                 330                 335

Gln Gly Gly Tyr Gly Gly Leu Gly Ser Gln Gly Thr Ala Ser Gly Arg
            340                 345                 350

Gly Gly Leu Gly Gly Gln Gly Ala Gly Ala Ala Ala Ala Gly Gly
        355                 360                 365

Ala Gly Gln Gly Gly Tyr Gly Gly Leu Gly Ser Gln Gly Thr Ala Ser
    370                 375                 380

Gly Arg Gly Gly Leu Gly Gly Gln Gly Ala Gly Ala Ala Ala Ala
385                 390                 395                 400

Gly Gly Ala Gly Gln Gly Gly Tyr Gly Gly Leu Gly Ser Gln Gly Thr
                405                 410                 415
```

```
Ala Ser Gly Arg Gly Gly Leu Gly Gly Gln Gly Ala Gly Ala Ala Ala
            420                 425                 430

Ala Ala Gly Gly Ala Gly Gln Gly Gly Tyr Gly Gly Leu Gly Ser Gln
            435                 440                 445

Gly Thr Ala Ser Gly Arg Gly Gly Leu Gly Gly Gln Gly Ala Gly Ala
    450                 455                 460

Ala Ala Ala Ala Gly Gly Ala Gly Gln Gly Gly Tyr Gly Gly Leu Gly
465                 470                 475                 480

Ser Gln Gly Thr Ala Ser Gly Arg Gly Gly Leu Gly Gly Gln Gly Ala
            485                 490                 495

Gly Ala Ala Ala Ala Gly Gly Ala Gly Gln Gly Gly Tyr Gly Gly
            500                 505                 510

Leu Gly Ser Gln Gly Thr Ala Ser Gly Arg Gly Gly Leu Gly Gly Gln
            515                 520                 525

Gly Ala Gly Ala Ala Ala Ala Gly Gly Ala Gly Gln Gly Gly Tyr
            530                 535                 540

Gly Gly Leu Gly Ser Gln Gly Thr Ser Gly Ser Ala Arg Ala Arg Ala
545                 550                 555                 560

Ala Ala Leu Glu His His His His His His
            565                 570

<210> SEQ ID NO 34
<211> LENGTH: 741
<212> TYPE: PRT
<213> ORGANISM: Artificial sequence
<220> FEATURE:
<223> OTHER INFORMATION: 6His tagged 15sps spider silk CBD fusion
      polypeptide

<400> SEQUENCE: 34

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Ser Gly
        35                  40                  45

Arg Gly Gly Leu Gly Gly Gln Gly Ala Gly Ala Ala Ala Ala Gly
    50                  55                  60

Gly Ala Gly Gln Gly Gly Tyr Gly Gly Leu Gly Ser Gln Gly Thr Ser
65                  70                  75                  80

Gly Arg Gly Gly Leu Gly Gly Gln Gly Ala Gly Ala Ala Ala Ser Ala
            85                  90                  95

Gly Gly Ala Gly Gln Gly Gly Tyr Gly Gly Leu Gly Ser Gln Gly Thr
            100                 105                 110

Ser Gly Arg Gly Gly Leu Gly Gly Gln Gly Ala Gly Ala Ala Ala Ala
            115                 120                 125

Ala Gly Gly Ala Gly Gln Gly Gly Tyr Gly Gly Leu Gly Ser Gln Gly
    130                 135                 140

Thr Ser Gly Arg Gly Gly Leu Gly Gly Gln Gly Ala Gly Ala Ala Ala
145                 150                 155                 160

Ala Ala Gly Gly Ala Gly Gln Gly Gly Tyr Gly Gly Leu Gly Ser Gln
            165                 170                 175

Gly Thr Ala Ser Gly Arg Gly Gly Leu Gly Gly Gln Gly Ala Gly Ala
        180                 185                 190

Ala Ala Ala Ala Gly Gly Ala Gly Gln Gly Gly Tyr Gly Gly Leu Gly
            195                 200                 205
```

-continued

Ser Gln Gly Thr Ala Ser Gly Arg Gly Gly Leu Gly Gln Gly Ala
    210                 215                 220

Gly Ala Ala Ala Ala Gly Gly Ala Gly Gln Gly Gly Tyr Gly Gly
225                 230                 235                 240

Leu Gly Ser Gln Gly Thr Ala Ser Gly Arg Gly Gly Leu Gly Gln
                245                 250                 255

Gly Ala Gly Ala Ala Ala Ala Gly Gly Ala Gly Gln Gly Gly Tyr
        260                 265                 270

Gly Gly Leu Gly Ser Gln Gly Thr Ala Ser Gly Arg Gly Gly Leu Gly
    275                 280                 285

Gly Gln Gly Ala Gly Ala Ala Ala Ala Gly Ala Gly Gln Gly
    290                 295                 300

Gly Tyr Gly Gly Leu Gly Ser Gln Gly Thr Ala Ser Gly Arg Gly
305                 310                 315                 320

Leu Gly Gly Gln Gly Ala Gly Ala Ala Ala Ala Gly Gly Ala Gly
                325                 330                 335

Gln Gly Gly Tyr Gly Gly Leu Gly Ser Gln Gly Thr Ala Ser Gly Arg
        340                 345                 350

Gly Gly Leu Gly Gly Gln Gly Ala Gly Ala Ala Ala Ala Gly Gly
    355                 360                 365

Ala Gly Gln Gly Gly Tyr Gly Gly Leu Gly Ser Gln Gly Thr Ala Ser
370                 375                 380

Gly Arg Gly Gly Leu Gly Gly Gln Gly Ala Gly Ala Ala Ala Ala
385                 390                 395                 400

Gly Gly Ala Gly Gln Gly Gly Tyr Gly Gly Leu Gly Ser Gln Gly Thr
        405                 410                 415

Ala Ser Gly Arg Gly Gly Leu Gly Gly Gln Gly Ala Gly Ala Ala Ala
        420                 425                 430

Ala Ala Gly Gly Ala Gly Gln Gly Gly Tyr Gly Gly Leu Gly Ser Gln
        435                 440                 445

Gly Thr Ala Ser Gly Arg Gly Gly Leu Gly Gly Gln Gly Ala Gly Ala
    450                 455                 460

Ala Ala Ala Ala Gly Gly Ala Gly Gln Gly Gly Tyr Gly Gly Leu Gly
465                 470                 475                 480

Ser Gln Gly Thr Ala Ser Gly Arg Gly Gly Leu Gly Gly Gln Gly Ala
                485                 490                 495

Gly Ala Ala Ala Ala Gly Gly Ala Gly Gln Gly Gly Tyr Gly Gly
        500                 505                 510

Leu Gly Ser Gln Gly Thr Ala Ser Gly Arg Gly Gly Leu Gly Gly Gln
    515                 520                 525

Gly Ala Gly Ala Ala Ala Ala Gly Gly Ala Gly Gln Gly Gly Tyr
        530                 535                 540

Gly Gly Leu Gly Ser Gln Gly Thr Ser Met Ala Ala Thr Ser Ser Met
545                 550                 555                 560

Ser Val Glu Phe Tyr Asn Ser Asn Lys Ala Ala Gln Thr Asn Ser Ile
                565                 570                 575

Thr Pro Ile Ile Lys Ile Thr Asn Thr Ala Asp Ser Asp Leu Asn Leu
                580                 585                 590

Asn Asp Val Lys Val Arg Tyr Tyr Tyr Thr Ser Asp Gly Thr Gln Gly
                595                 600                 605

Gln Thr Phe Trp Gly Asp His Ala Gly Ala Leu Leu Gly Asn Ser Tyr
    610                 615                 620

Val Asp Asn Thr Gly Lys Val Thr Ala Asn Phe Val Lys Glu Thr Ala
625                 630                 635                 640

```
Ser Pro Thr Ser Thr Tyr Asp Thr Tyr Val Glu Phe Gly Phe Ala Ser
            645                 650                 655

Gly Ala Ala Thr Leu Lys Lys Gly Gln Phe Ile Thr Ile Gln Gly Arg
            660                 665                 670

Ile Thr Lys Ser Asp Trp Ser Asn Tyr Ala Gln Thr Asn Asp Tyr Ser
            675                 680                 685

Phe Asp Ala Ser Ser Thr Pro Val Val Asn Pro Lys Val Thr Gly
            690                 695                 700

Tyr Ile Gly Gly Ala Lys Val Leu Gly Thr Ala Pro Gly Pro Asp Val
705                 710                 715                 720

Pro Ser Ser Ile Ile Asn Pro Thr Ser Ala Thr Phe Asp Leu Glu His
            725                 730                 735

His His His His His
            740

<210> SEQ ID NO 35
<211> LENGTH: 774
<212> TYPE: PRT
<213> ORGANISM: Artificial sequence
<220> FEATURE:
<223> OTHER INFORMATION: CBDclos 12sps spider silk fusion polypeptide

<400> SEQUENCE: 35

Asn Ser Ile Thr Pro Ile Ile Lys Ile Thr Asn Thr Ala Asp Ser Asp
1               5                   10                  15

Leu Asn Leu Asn Asp Val Lys Val Arg Tyr Tyr Tyr Thr Ser Asp Gly
            20                  25                  30

Thr Gln Gly Gln Thr Phe Trp Gly Asp His Ala Gly Ala Leu Leu Gly
            35                  40                  45

Asn Ser Tyr Val Asp Asn Thr Gly Lys Val Thr Ala Asn Phe Val Lys
        50                  55                  60

Glu Thr Ala Ser Pro Thr Ser Thr Tyr Asp Thr Tyr Val Glu Phe Gly
65              70                  75                  80

Phe Ala Ser Gly Ala Ala Thr Leu Lys Lys Gly Gln Phe Ile Thr Ile
                85                  90                  95

Gln Gly Arg Ile Thr Lys Ser Asp Trp Ser Asn Tyr Ala Gln Thr Asn
            100                 105                 110

Asp Tyr Ser Phe Asp Ala Ser Ser Thr Pro Val Val Asn Pro Lys
        115                 120                 125

Val Thr Gly Tyr Ile Gly Gly Ala Lys Val Leu Gly Thr Ala Pro Gly
            130                 135                 140

Pro Asp Val Pro Ser Ser Ile Ile Asn Pro Thr Ser Ala Thr Phe Asp
145                 150                 155                 160

Pro Gly Thr Met Ala Ser Met Thr Gly Gly Gln Gln Met Gly Arg Ile
                165                 170                 175

Gly Ser Pro Pro Gly Pro Gly Pro Gly Gln Gly Pro Tyr Gly Pro
            180                 185                 190

Gly Ala Ser Ala Ala Ala Ala Ala Gly Gly Tyr Gly Pro Gly Ser
            195                 200                 205

Gly Gln Gln Gly Pro Gln Gln Gly Pro Gln Gln Ala Gly Pro
            210                 215                 220

Gly Gly Gln Gly Pro Tyr Gly Pro Gly Ala Ser Ala Ala Ala Ala
225                 230                 235                 240

Ala Gly Gly Tyr Gly Pro Gly Ser Gly Gln Gln Gly Pro Gly Gln Gln
                245                 250                 255
```

-continued

Gly Pro Gly Gln Gln Ala Gly Pro Gly Gln Gly Pro Tyr Gly Pro
           260                 265                 270

Gly Ala Ser Ala Ala Ala Ala Ala Gly Gly Tyr Gly Pro Gly Ser
           275                 280                 285

Gly Gln Gln Gly Pro Gly Gln Gln Gly Pro Gly Gln Gln Ala Gly Pro
           290                 295                 300

Gly Gly Gln Gly Pro Tyr Gly Pro Gly Ala Ser Ala Ala Ala Ala
305                 310                 315                 320

Ala Gly Gly Tyr Gly Pro Gly Ser Gly Gln Gln Gly Pro Gly Gln Gln
                    325                 330                 335

Gly Pro Gly Gln Gln Ala Gly Pro Gly Gly Gln Gly Pro Tyr Gly Pro
           340                 345                 350

Gly Ala Ser Ala Ala Ala Ala Ala Gly Gly Tyr Gly Pro Gly Ser
           355                 360                 365

Gly Gln Gln Gly Pro Gly Gln Gln Gly Pro Gly Gln Gln Ala Gly Pro
           370                 375                 380

Gly Gly Gln Gly Pro Tyr Gly Pro Gly Ala Ser Ala Ala Ala Ala
385                 390                 395                 400

Ala Gly Gly Tyr Gly Pro Gly Ser Gly Gln Gln Gly Pro Gly Gln Gln
                    405                 410                 415

Gly Pro Gly Gln Gln Ala Gly Pro Gly Gly Gln Gly Pro Tyr Gly Pro
           420                 425                 430

Gly Ala Ser Ala Ala Ala Ala Ala Gly Gly Tyr Gly Pro Gly Ser
           435                 440                 445

Gly Gln Gln Gly Pro Gly Gln Gln Gly Pro Gly Gln Gln Ala Gly Pro
           450                 455                 460

Gly Gly Gln Gly Pro Tyr Gly Pro Gly Ala Ser Ala Ala Ala Ala
465                 470                 475                 480

Ala Gly Gly Tyr Gly Pro Gly Ser Gly Gln Gln Gly Pro Gly Gln Gln
                    485                 490                 495

Gly Pro Gly Gln Gln Ala Gly Pro Gly Gly Gln Gly Pro Tyr Gly Pro
           500                 505                 510

Gly Ala Ser Ala Ala Ala Ala Ala Gly Gly Tyr Gly Pro Gly Ser
           515                 520                 525

Gly Gln Gln Gly Pro Gly Gln Gln Gly Pro Gly Gln Gln Ala Gly Pro
           530                 535                 540

Gly Gly Gln Gly Pro Tyr Gly Pro Gly Ala Ser Ala Ala Ala Ala
545                 550                 555                 560

Ala Gly Gly Tyr Gly Pro Gly Ser Gly Gln Gln Gly Pro Gly Gln Gln
                    565                 570                 575

Gly Pro Gly Gln Gln Ala Gly Pro Gly Gly Gln Gly Pro Tyr Gly Pro
           580                 585                 590

Gly Ala Ser Ala Ala Ala Ala Ala Gly Gly Tyr Gly Pro Gly Ser
           595                 600                 605

Gly Gln Gln Gly Pro Gly Gln Gln Gly Pro Gly Gln Gln Ala Gly Pro
           610                 615                 620

Gly Gly Gln Gly Pro Tyr Gly Pro Gly Ala Ser Ala Ala Ala Ala
625                 630                 635                 640

Ala Gly Gly Tyr Gly Pro Gly Ser Gly Gln Gln Gly Pro Gly Gln Gln
                    645                 650                 655

Gly Pro Gly Gln Gln Ala Gly Ser Ser Val Pro Val Ala Ser Ala Val
           660                 665                 670

Ala Ser Arg Leu Ser Ser Pro Ala Ala Ser Ser Arg Val Ser Ser Ala
           675                 680                 685

```
Val Ser Ser Leu Val Ser Ser Gly Pro Thr Lys His Ala Ala Leu Ser
    690                 695                 700

Asn Thr Ile Ser Ser Val Val Ser Gln Val Ser Ala Ser Asn Pro Gly
705                 710                 715                 720

Leu Ser Gly Cys Asp Val Leu Val Gln Ala Leu Leu Glu Val Val Ser
                725                 730                 735

Ala Leu Val Ser Ile Leu Gly Ser Ser Ser Ile Gly Gln Ile Asn Tyr
            740                 745                 750

Gly Ala Ser Ala Gln Tyr Thr Gln Met Val Gly Gln Ser Val Ala Gln
        755                 760                 765

Ala Leu Ala Ala Ala Ala
    770

<210> SEQ ID NO 36
<211> LENGTH: 803
<212> TYPE: PRT
<213> ORGANISM: Artificial sequence
<220> FEATURE:
<223> OTHER INFORMATION: 6sps-CBD-6sps fusion polypeptide

<400> SEQUENCE: 36

Met Gln Phe Arg Gly Pro Gly Gly Gln Gly Pro Tyr Gly Pro Gly Ala
1               5                   10                  15

Ser Ala Ala Ala Ala Ala Gly Gly Tyr Gly Pro Gly Ser Gly Gln
            20                  25                  30

Gln Gly Pro Gly Gln Gln Gly Pro Gly Gln Gln Ala Gly Pro Gly Gly
        35                  40                  45

Gln Gly Pro Tyr Gly Pro Gly Ala Ser Ala Ala Ala Ala Ala Ala Gly
    50                  55                  60

Gly Tyr Gly Pro Gly Ser Gly Gln Gln Gly Pro Gly Gln Gln Gly Pro
65                  70                  75                  80

Gly Gln Gln Ala Gly Pro Gly Gln Gly Pro Tyr Gly Pro Gly Ala
            85                  90                  95

Ser Ala Ala Ala Ala Ala Ala Gly Gly Tyr Gly Pro Gly Ser Gly Gln
            100                 105                 110

Gln Gly Pro Gly Gln Gln Gly Pro Gly Gln Gln Ala Gly Pro Gly Gly
        115                 120                 125

Gln Gly Pro Tyr Gly Pro Gly Ala Ser Ala Ala Ala Ala Ala Ala Gly
    130                 135                 140

Gly Tyr Gly Pro Gly Ser Gly Gln Gln Gly Pro Gly Gln Gln Gly Pro
145                 150                 155                 160

Gly Gln Gln Ala Gly Pro Gly Gln Gly Pro Tyr Gly Pro Gly Ala
            165                 170                 175

Ser Ala Ala Ala Ala Ala Ala Gly Gly Tyr Gly Pro Gly Ser Gly Gln
            180                 185                 190

Gln Gly Pro Gly Gln Gln Gly Pro Gly Gln Gln Ala Gly Pro Gly Gly
        195                 200                 205

Gln Gly Pro Tyr Gly Pro Gly Ala Ser Ala Ala Ala Ala Ala Ala Gly
    210                 215                 220

Gly Tyr Gly Pro Gly Ser Gly Gln Gln Gly Pro Gly Gln Gln Gly Pro
225                 230                 235                 240

Gly Gln Gln Ala Pro Pro Gly Ala His Met Ala Ala Thr Ser Ser Met
            245                 250                 255

Ser Val Glu Phe Tyr Asn Ser Asn Lys Ala Ala Gln Thr Asn Ser Ile
            260                 265                 270
```

```
          Thr Pro Ile Ile Lys Ile Thr Asn Thr Ala Asp Ser Asp Leu Asn Leu
              275                 280                 285

Asn Asp Val Lys Val Arg Tyr Tyr Thr Ser Asp Gly Thr Gln Gly
          290                 295                 300

Gln Thr Phe Trp Gly Asp His Ala Gly Ala Leu Leu Gly Asn Ser Tyr
          305                 310                 315                 320

Val Asp Asn Thr Gly Lys Val Thr Ala Asn Phe Val Lys Glu Thr Ala
                          325                 330                 335

Ser Pro Thr Ser Thr Tyr Asp Thr Tyr Val Glu Phe Gly Phe Ala Ser
                          340                 345                 350

Gly Ala Ala Thr Leu Lys Lys Gly Gln Phe Ile Thr Ile Gln Gly Arg
                  355                 360                 365

Ile Thr Lys Ser Asp Trp Ser Asn Tyr Ala Gln Thr Asn Asp Tyr Ser
          370                 375                 380

Phe Asp Ala Ser Ser Thr Pro Val Val Asn Pro Lys Val Thr Gly
          385                 390                 395                 400

Tyr Ile Gly Gly Ala Lys Val Leu Gly Thr Ala Pro Gly Pro Asp Val
                              405                 410                 415

Pro Ser Ser Ile Ile Asn Pro Thr Ser Ala Thr Phe Asp Pro Gly Thr
                          420                 425                 430

Met Ala Ser Met Thr Gly Gly Gln Gln Met Gly Arg Ile Gly Ser Pro
                  435                 440                 445

Pro Gly Pro Gly Pro Gly Gly Gln Pro Tyr Gly Pro Gly Ala Ser
                  450                 455                 460

Ala Ala Ala Ala Ala Ala Gly Gly Tyr Gly Pro Gly Ser Gly Gln Gln
          465                 470                 475                 480

Gly Pro Gly Gln Gln Gly Pro Gly Gln Gln Ala Gly Pro Gly Gln
                              485                 490                 495

Gly Pro Tyr Gly Pro Gly Ala Ser Ala Ala Ala Ala Ala Gly Gly
                          500                 505                 510

Tyr Gly Pro Gly Ser Gly Gln Gln Gly Pro Gly Gln Gln Gly Pro Gly
                          515                 520                 525

Gln Gln Ala Gly Pro Gly Gly Gln Gly Pro Tyr Gly Pro Gly Ala Ser
          530                 535                 540

Ala Ala Ala Ala Ala Ala Gly Gly Tyr Gly Pro Gly Ser Gly Gln Gln
          545                 550                 555                 560

Gly Pro Gly Gln Gln Gly Pro Gly Gln Gln Ala Gly Pro Gly Gly Gln
                              565                 570                 575

Gly Pro Tyr Gly Pro Gly Ala Ser Ala Ala Ala Ala Ala Gly Gly
                          580                 585                 590

Tyr Gly Pro Gly Ser Gly Gln Gln Gly Pro Gly Gln Gln Gly Pro Gly
                          595                 600                 605

Gln Gln Ala Gly Pro Gly Gly Gln Gly Pro Tyr Gly Pro Gly Ala Ser
          610                 615                 620

Ala Ala Ala Ala Ala Ala Gly Gly Tyr Gly Pro Gly Ser Gly Gln Gln
          625                 630                 635                 640

Gly Pro Gly Gln Gln Gly Pro Gly Gln Gln Ala Gly Pro Gly Gly Gln
                              645                 650                 655

Gly Pro Tyr Gly Pro Gly Ala Ser Ala Ala Ala Ala Ala Gly Gly
                          660                 665                 670

Tyr Gly Pro Gly Ser Gly Gln Gln Gly Pro Gly Gln Gln Gly Pro Gly
                          675                 680                 685

Gln Gln Ala Gly Ser Ser Val Pro Val Ala Ser Ala Val Ala Ser Arg
          690                 695                 700
```

-continued

```
Leu Ser Ser Pro Ala Ala Ser Ser Arg Val Ser Ser Ala Val Ser Ser
705                 710                 715                 720

Leu Val Ser Ser Gly Pro Thr Lys His Ala Ala Leu Ser Asn Thr Ile
            725                 730                 735

Ser Ser Val Val Ser Gln Val Ser Ala Ser Asn Pro Gly Leu Ser Gly
        740                 745                 750

Cys Asp Val Leu Val Gln Ala Leu Leu Glu Val Val Ser Ala Leu Val
            755                 760                 765

Ser Ile Leu Gly Ser Ser Ser Ile Gly Gln Ile Asn Tyr Gly Ala Ser
        770                 775                 780

Ala Gln Tyr Thr Gln Met Val Gly Gln Ser Val Ala Gln Ala Leu Ala
785                 790                 795                 800

Ala Ala Ala

<210> SEQ ID NO 37
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 37
gactagtatg gcagcgacat catcaatgtc                                       30

<210> SEQ ID NO 38
<211> LENGTH: 212
<212> TYPE: PRT
<213> ORGANISM: Artificial sequence
<220> FEATURE:
<223> OTHER INFORMATION: Synthetic spider silk repeating unit (GENEART)
      polypeptide

<400> SEQUENCE: 38

Ile Ile Lys Ile Thr Asn Thr Ala Asp Ser Asp Leu Asn Leu Asn Asp
1               5                   10                  15

Val Lys Val Arg Tyr Tyr Tyr Thr Ser Asp Gly Thr Gln Gly Gln Thr
            20                  25                  30

Phe Trp Gly Asp His Ala Thr Met Ala Ser Met Thr Gly Gly Gln Gln
        35                  40                  45

Met Gly Arg Ile Gly Ser Pro Pro Gly Pro Gly Pro Gly Gly Gln Gly
    50                  55                  60

Pro Tyr Gly Pro Gly Ala Ser Ala Ala Ala Ala Ala Gly Gly Tyr
65                  70                  75                  80

Gly Pro Gly Ser Gly Gln Gln Gly Pro Gly Gln Gln Gly Pro Gly Gln
                85                  90                  95

Gln Ala Gly Ser Ser Val Pro Val Ala Ser Ala Val Ala Ser Arg Leu
            100                 105                 110

Ser Ser Pro Ala Ala Ser Ser Arg Val Ser Ser Ala Val Ser Ser Leu
        115                 120                 125

Val Ser Ser Gly Pro Thr Lys His Ala Ala Leu Ser Asn Thr Ile Ser
    130                 135                 140

Ser Val Val Ser Gln Val Ser Ala Ser Asn Pro Gly Leu Ser Gly Cys
145                 150                 155                 160

Asp Val Leu Val Gln Ala Leu Leu Glu Val Val Ser Ala Leu Val Ser
                165                 170                 175

Ile Leu Gly Ser Ser Ser Ile Gly Gln Ile Asn Tyr Gly Ala Ser Ala
            180                 185                 190
```

```
Gln Tyr Thr Gln Met Val Gly Gln Ser Val Ala Gln Ala Leu Ala Ala
        195                 200                 205

Ala Ala Ser Leu
    210

<210> SEQ ID NO 39
<211> LENGTH: 74
<212> TYPE: PRT
<213> ORGANISM: Drosophila melanogaster
<220> FEATURE:
<221> NAME/KEY: misc_feature
<223> OTHER INFORMATION: Resilin Chitin binding domain

<400> SEQUENCE: 39

Pro Ala Lys Tyr Glu Phe Asn Tyr Gln Val Glu Asp Ala Pro Ser Gly
1               5                   10                  15

Leu Ser Phe Gly His Ser Glu Met Arg Asp Gly Asp Phe Thr Thr Gly
            20                  25                  30

Gln Tyr Asn Val Leu Leu Pro Asp Gly Arg Lys Gln Ile Val Glu Tyr
        35                  40                  45

Glu Ala Asp Gln Gln Gly Tyr Arg Pro Gln Ile Arg Tyr Glu Gly Asp
    50                  55                  60

Ala Asn Asp Gly Ser Gly Pro Ser Gly Pro
65                  70

<210> SEQ ID NO 40
<211> LENGTH: 42
<212> TYPE: PRT
<213> ORGANISM: Arabidopsis thaliana
<220> FEATURE:
<221> NAME/KEY: misc_feature
<223> OTHER INFORMATION: Basic endochitinase B Chitin binding domain

<400> SEQUENCE: 40

Glu Gln Cys Gly Arg Gln Ala Gly Gly Ala Leu Cys Pro Asn Gly Leu
1               5                   10                  15

Cys Cys Ser Glu Phe Gly Trp Cys Gly Asn Thr Glu Pro Tyr Cys Lys
            20                  25                  30

Gln Pro Gly Cys Gln Ser Gln Cys Thr Pro
        35                  40

<210> SEQ ID NO 41
<211> LENGTH: 112
<212> TYPE: PRT
<213> ORGANISM: Aspergillus niger
<220> FEATURE:
<221> NAME/KEY: misc_feature
<223> OTHER INFORMATION: Glucoamylase starch-binding domain

<400> SEQUENCE: 41

Ser Ser Thr Ser Cys Thr Thr Pro Thr Ala Val Ala Val Thr Phe Asp
1               5                   10                  15

Leu Thr Ala Thr Thr Thr Tyr Gly Glu Asn Ile Tyr Leu Val Gly Ser
            20                  25                  30

Ile Ser Gln Leu Gly Asp Trp Asp Thr Ser Asp Gly Ile Ala Leu Ser
        35                  40                  45

Ala Asp Lys Tyr Thr Ser Ser Asn Pro Leu Trp Tyr Val Thr Val Thr
    50                  55                  60

Leu Pro Ala Gly Glu Ser Phe Glu Tyr Lys Phe Ile Arg Ile Glu Ser
65                  70                  75                  80
```

```
Asp Asp Ser Val Glu Trp Glu Ser Asp Pro Asn Arg Glu Tyr Thr Val
                85                  90                  95

Pro Gln Val Cys Gly Glu Ser Thr Ala Thr Val Thr Asp Thr Trp Arg
            100                 105                 110
```

<210> SEQ ID NO 42
<211> LENGTH: 116
<212> TYPE: PRT
<213> ORGANISM: Streptococcus mutans
<220> FEATURE:
<221> NAME/KEY: misc_feature
<223> OTHER INFORMATION: Dextran binding domain

<400> SEQUENCE: 42

```
Leu Gly Ile Asn Gly Asp Gln Val Trp Thr Tyr Ala Lys Lys Gly Asn
1               5                   10                  15

Asp Phe Arg Thr Ile Gln Leu Leu Asn Leu Met Gly Ile Thr Ser Asp
            20                  25                  30

Trp Lys Asn Glu Asp Gly Tyr Glu Asn Lys Thr Pro Asp Glu Gln
        35                  40                  45

Thr Asn Leu Leu Val Thr Tyr Pro Leu Thr Gly Val Ser Met Ala Glu
    50                  55                  60

Ala Asp Arg Ile Ala Lys Gln Val Tyr Leu Thr Ser Pro Asp Asp Trp
65                  70                  75                  80

Leu Gln Ser Ser Met Ile Ser Leu Ala Thr Gln Ile Lys Thr Asn Glu
                85                  90                  95

Asn Gly Asp Pro Val Leu Tyr Ile Gln Val Pro Arg Leu Thr Leu Trp
            100                 105                 110

Asp Met Ile Tyr
            115
```

<210> SEQ ID NO 43
<211> LENGTH: 347
<212> TYPE: PRT
<213> ORGANISM: Sphingomonas sp.
<220> FEATURE:
<221> NAME/KEY: misc_feature
<223> OTHER INFORMATION: Alginate binding domain

<400> SEQUENCE: 43

```
Lys Glu Ala Thr Trp Val Thr Asp Lys Pro Leu Thr Leu Lys Ile His
1               5                   10                  15

Met His Phe Arg Asp Lys Trp Val Trp Asp Glu Asn Trp Pro Val Ala
            20                  25                  30

Lys Glu Ser Phe Arg Leu Thr Asn Val Lys Leu Gln Ser Val Ala Asn
            35                  40                  45

Lys Ala Ala Thr Asn Ser Gln Glu Gln Phe Asn Leu Met Met Ala Ser
    50                  55                  60

Gly Asp Leu Pro Asp Val Val Gly Gly Asp Asn Leu Lys Asp Lys Phe
65                  70                  75                  80

Ile Gln Tyr Gly Gln Glu Gly Ala Phe Val Pro Leu Asn Lys Leu Ile
                85                  90                  95

Asp Gln Tyr Ala Pro His Ile Lys Ala Phe Phe Lys Ser His Pro Glu
            100                 105                 110

Val Glu Arg Ala Ile Lys Ala Pro Asp Gly Asn Ile Tyr Phe Ile Pro
            115                 120                 125

Tyr Val Pro Asp Gly Val Val Ala Arg Gly Tyr Phe Ile Arg Glu Asp
            130                 135                 140
```

```
Trp Leu Lys Lys Leu Asn Leu Lys Pro Pro Gln Asn Ile Asp Glu Leu
145                 150                 155                 160

Tyr Thr Val Leu Lys Ala Phe Lys Glu Lys Asp Pro Asn Gly Asn Gly
                165                 170                 175

Lys Ala Asp Glu Val Pro Phe Ile Asp Arg His Pro Asp Glu Val Phe
            180                 185                 190

Arg Leu Val Asn Phe Trp Gly Ala Arg Ser Ser Gly Ser Asp Asn Tyr
        195                 200                 205

Met Asp Phe Tyr Ile Asp Asn Gly Arg Val Lys His Pro Trp Ala Glu
210                 215                 220

Thr Ala Phe Arg Asp Gly Met Lys His Val Ala Gln Trp Tyr Lys Glu
225                 230                 235                 240

Gly Leu Ile Asp Lys Glu Ile Phe Thr Arg Lys Ala Lys Ala Arg Glu
                245                 250                 255

Gln Met Phe Gly Gly Asn Leu Gly Gly Phe Thr His Asp Trp Phe Ala
            260                 265                 270

Ser Thr Met Thr Phe Asn Glu Gly Leu Ala Lys Thr Val Pro Gly Phe
        275                 280                 285

Lys Leu Ile Pro Ile Ala Pro Pro Thr Asn Ser Lys Gly Gln Arg Trp
290                 295                 300

Glu Glu Asp Ser Arg Gln Lys Val Arg Pro Asp Gly Trp Ala Ile Thr
305                 310                 315                 320

Val Lys Asn Lys Asn Pro Val Glu Thr Ile Lys Phe Phe Asp Phe Tyr
                325                 330                 335

Phe Ser Arg Pro Gly Arg Asp Ile Ser Asn Phe
            340                 345

<210> SEQ ID NO 44
<211> LENGTH: 105
<212> TYPE: PRT
<213> ORGANISM: Rattus norvegicus
<220> FEATURE:
<221> NAME/KEY: misc_feature
<223> OTHER INFORMATION: Hyaluronic acid binding domain

<400> SEQUENCE: 44

Gly Lys Arg Asp Phe Glu Arg Tyr Gly Ser Ser Asp Lys Ala Asn Arg
1               5                   10                  15

Met Glu Asp Ser Met Gly Gly Cys Gly Val Arg Thr Trp Gly Ser Gly
            20                  25                  30

Lys Asp Thr Ser Asp Thr Glu Pro Pro Ala Pro Met Glu Glu Thr Ser
        35                  40                  45

Met Met Glu Glu Cys Gln Gly Val Leu Asp Glu Ser Ala Ser Lys
50                  55                  60

Val Pro Glu Leu Glu Val Glu Glu Asn Gln Val Gln Glu Met Thr
65                  70                  75                  80

Leu Asp Glu Trp Lys Asn Leu Gln Glu Gln Thr Arg Pro Lys Pro Glu
                85                  90                  95

Phe Asn Ile Arg Lys Pro Glu Ser Thr
            100                 105

<210> SEQ ID NO 45
<211> LENGTH: 7
<212> TYPE: PRT
<213> ORGANISM: Artificial sequence
<220> FEATURE:
<223> OTHER INFORMATION: Repeating amino acid sequence in resilin
```

```
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 45

Ser Xaa Xaa Tyr Gly Xaa Pro
1               5

<210> SEQ ID NO 46
<211> LENGTH: 5
<212> TYPE: PRT
<213> ORGANISM: Artificial sequence
<220> FEATURE:
<223> OTHER INFORMATION: Repeating amino acid sequence in elastin

<400> SEQUENCE: 46

Gly Val Gly Val Pro
1               5

<210> SEQ ID NO 47
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 47
ctcgagatca aatgttgcag aagtaggatt aattattg                              38

<210> SEQ ID NO 48
<211> LENGTH: 138
<212> TYPE: DNA
<213> ORGANISM: Artificial sequence
<220> FEATURE:
<223> OTHER INFORMATION: Vacuolar sorting signal coding polynucleotide

<400> SEQUENCE: 48
atggctcacg ctcgtgttct cctcctcgct ctcgctgttt tggcaacagc tgctgtggct      60
gtggcttcta gttcttcttt tgctgattca aaccctatta gacctgttac tgatagagca    120
gcttccactt tgcaattg                                                  138

<210> SEQ ID NO 49
<211> LENGTH: 46
<212> TYPE: PRT
<213> ORGANISM: Artificial sequence
<220> FEATURE:
<223> OTHER INFORMATION: Vacuolar sorting signal polypeptide

<400> SEQUENCE: 49

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Gln Leu
        35                  40                  45

<210> SEQ ID NO 50
<211> LENGTH: 127
<212> TYPE: DNA
<213> ORGANISM: Artificial sequence
```

```
<220> FEATURE:
<223> OTHER INFORMATION: Apoplast sorting signal coding polynucleotide

<400> SEQUENCE: 50
gccatggcta ggaagtcttt gattttccca gtgattcttc ttgctgtgct tctttctct      60 ccacctattt actctgctgg acacgattat agggatgctc ttaggaagtc atctatggct    120
caattgc                                                              127

<210> SEQ ID NO 51
<211> LENGTH: 41
<212> TYPE: PRT
<213> ORGANISM: Artificial sequence
<220> FEATURE:
<223> OTHER INFORMATION: apoplast sorting signal polypeptide

<400> SEQUENCE: 51

Met Ala Arg Lys Ser Leu Ile Phe Pro Val Ile Leu Leu Ala Val Leu
1               5                   10                  15

Leu Phe Ser Pro Pro Ile Tyr Ser Ala Gly His Asp Tyr Arg Asp Ala
            20                  25                  30

Leu Arg Lys Ser Ser Met Ala Gln Leu
        35                  40

<210> SEQ ID NO 52
<211> LENGTH: 17
<212> TYPE: PRT
<213> ORGANISM: Artificial sequence
<220> FEATURE:
<223> OTHER INFORMATION: Polypeptide used as linker between CBD and
      resilin

<400> SEQUENCE: 52

Gly Pro Asp Val Pro Ser Ser Ile Ile Asn Pro Thr Ser Ala Thr Phe
1               5                   10                  15

Asp

<210> SEQ ID NO 53
<211> LENGTH: 6
<212> TYPE: PRT
<213> ORGANISM: Artificial sequence
<220> FEATURE:
<223> OTHER INFORMATION: Polypeptide used as linker between resilin and
      CBD

<400> SEQUENCE: 53

Gly Ile Pro Asp Pro Gly
1               5

<210> SEQ ID NO 54
<211> LENGTH: 324
<212> TYPE: DNA
<213> ORGANISM: Artificial sequence
<220> FEATURE:
<223> OTHER INFORMATION: pHIS-Parallel3 fragment including Lac operator,
      6XHis tag, a spacer region, rTEV cleavge site and a multiple
      cloning site

<400> SEQUENCE: 54
gaaattaata cgactcacta tagggggaatt gtgagcggat aacaattccc ctctagaaat     60
aattttgttt aactttaaga aggagatata catatgtcgt actaccatca ccatcaccat    120
cacgattacg atatcccaac gaccgaaaac ctgtattttc agggcgccat ggggatccgg    180
aattcaaagg cctacgtcga cgagctcaac tagtgcggcc gctttcgaat ctagagcctg    240
```

```
cagtctcgag caccaccacc accaccactg agatccggct gctaacaaag cccgaaagga    300
agctgagttg gctgctgcca ccgc                                          324
```

<210> SEQ ID NO 55
<211> LENGTH: 424
<212> TYPE: PRT
<213> ORGANISM: Artificial sequence
<220> FEATURE:
<223> OTHER INFORMATION: 6H-Res-ChBD

<400> SEQUENCE: 55

```
Met Ser Tyr Tyr His His His His His Asp Tyr Asp Ile Pro Thr
1               5                   10                  15

Thr Glu Asn Leu Tyr Phe Gln Gly Ala Met Gly Pro Glu Pro Val
                20                  25                  30

Asn Ser Tyr Leu Pro Pro Ser Asp Ser Tyr Gly Ala Pro Gly Gln Ser
            35                  40                  45

Gly Pro Gly Gly Arg Pro Ser Asp Ser Tyr Gly Ala Pro Gly Gly Gly
        50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
                85                  90                  95

Tyr Gly Ala Pro Gly Gly Gly Asn Gly Asn Gly Arg Pro Ser Ser
            100                 105                 110

Ser Tyr Gly Ala Pro Gly Gly Gly Asn Gly Gly Arg Pro Ser Asp Thr
        115                 120                 125

Tyr Gly Ala Pro Gly Gly Gly Asn Gly Gly Arg Pro Ser Asp Thr Tyr
    130                 135                 140

Gly Ala Pro Gly Gly Gly Asn Gly Asn Gly Arg Pro Ser Ser
145                 150                 155                 160

Ser Tyr Gly Ala Pro Gly Gln Gly Gln Gly Asn Gly Asn Gly Arg
                165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
        195                 200                 205

Asp Thr Tyr Gly Ala Pro Gly Gly Gly Asn Asn Gly Gly Arg Pro Ser
    210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gln Asn Gln Lys Pro
        275                 280                 285

Ser Asp Ser Tyr Gly Ala Pro Gly Ser Gly Asn Gly Asn Gly Arg
    290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Ala
                325                 330                 335

Gly Gly Ser Gly Pro Gly Gly Ala Asp Tyr Asp Asn Asp Glu Pro Ala
            340                 345                 350
```

```
Lys Tyr Glu Phe Asn Tyr Gln Val Glu Asp Ala Pro Ser Gly Leu Ser
            355                 360                 365

Phe Gly His Ser Glu Met Arg Asp Gly Asp Phe Thr Thr Gly Gln Tyr
370                 375                 380

Asn Val Leu Leu Pro Asp Gly Arg Lys Gln Ile Val Glu Tyr Glu Ala
385                 390                 395                 400

Asp Gln Gln Gly Tyr Arg Pro Gln Ile Arg Tyr Glu Gly Asp Ala Asn
                405                 410                 415

Asp Gly Ser Gly Pro Ser Gly Pro
            420

<210> SEQ ID NO 56
<211> LENGTH: 354
<212> TYPE: PRT
<213> ORGANISM: Artificial sequence
<220> FEATURE:
<223> OTHER INFORMATION: 6H-Resilin

<400> SEQUENCE: 56

Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
                85                  90                  95

Tyr Gly Ala Pro Gly Gly Gly Asn Gly Asn Gly Arg Pro Ser Ser
                100                 105                 110

Ser Tyr Gly Ala Pro Gly Gly Gly Asn Gly Arg Pro Ser Asp Thr
        115                 120                 125

Tyr Gly Ala Pro Gly Gly Gly Asn Gly Arg Pro Ser Asp Thr Tyr
                130                 135                 140

Gly Ala Pro Gly Gly Gly Asn Gly Asn Gly Arg Pro Ser Ser
145                 150                 155                 160

Ser Tyr Gly Ala Pro Gly Gln Gly Gln Gly Asn Gly Asn Gly Arg
                165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
        195                 200                 205

Asp Thr Tyr Gly Ala Pro Gly Gly Gly Asn Asn Gly Gly Arg Pro Ser
    210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
        275                 280                 285
```

-continued

```
Ser Asp Ser Tyr Gly Ala Pro Gly Ser Gly Asn Gly Asn Gly Gly Arg
    290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
                325                 330                 335

Gly Gly Ser Gly Pro Gly Gly Ala Asp Tyr Asp Asn Asp Glu Gly Ser
            340                 345                 350

Asn His

<210> SEQ ID NO 57
<211> LENGTH: 528
<212> TYPE: PRT
<213> ORGANISM: Artificial sequence
<220> FEATURE:
<223> OTHER INFORMATION: 6H-CBD-resilin

<400> SEQUENCE: 57

Met Ser Tyr Tyr His His His His His Asp Tyr Asp Ile Pro Thr
1               5                   10                  15

Thr Glu Asn Leu Tyr Phe Gln Gly Ala Met Ala Ala Thr Ser Ser Met
                20                  25                  30

Ser Val Glu Phe Tyr Asn Ser Asn Lys Ala Ala Gln Thr Asn Ser Ile
            35                  40                  45

Thr Pro Ile Ile Lys Ile Thr Asn Thr Ala Asp Ser Asp Leu Asn Leu
    50                  55                  60

Asn Asp Val Lys Val Arg Tyr Tyr Tyr Thr Ser Asp Gly Thr Gln Gly
65                  70                  75                  80

Gln Thr Phe Trp Gly Asp His Ala Gly Ala Leu Leu Gly Asn Ser Tyr
                85                  90                  95

Val Asp Asn Thr Gly Lys Val Thr Ala Asn Phe Val Lys Glu Thr Ala
            100                 105                 110

Ser Pro Thr Ser Thr Tyr Asp Thr Tyr Val Glu Phe Gly Phe Ala Ser
    115                 120                 125

Gly Ala Ala Thr Leu Lys Lys Gly Gln Phe Ile Thr Ile Gln Gly Arg
    130                 135                 140

Ile Thr Lys Ser Asp Trp Ser Asn Tyr Ala Gln Thr Asn Asp Tyr Ser
145                 150                 155                 160

Phe Asp Ala Ser Ser Ser Thr Pro Val Val Asn Pro Lys Val Thr Gly
                165                 170                 175

Tyr Ile Gly Gly Ala Lys Val Leu Gly Thr Ala Pro Gly Pro Asp Val
            180                 185                 190

Pro Ser Ser Ile Ile Asn Pro Thr Ser Ala Thr Phe Asp Pro Glu Pro
    195                 200                 205

Pro Val Asn Ser Tyr Leu Pro Pro Ser Asp Ser Tyr Gly Ala Pro Gly
    210                 215                 220

Gln Ser Gly Pro Gly Gly Arg Pro Ser Asp Ser Tyr Gly Ala Pro Gly
225                 230                 235                 240

Gly Gly Asn Gly Gly Arg Pro Ser Asp Ser Tyr Gly Ala Pro Gly Gln
                245                 250                 255

Gly Gln Gly Gln Gly Gln Gly Gln Gly Gly Tyr Ala Gly Lys Pro Ser
            260                 265                 270

Asp Thr Tyr Gly Ala Pro Gly Gly Asn Gly Asn Gly Gly Arg Pro
    275                 280                 285

Ser Ser Ser Tyr Gly Ala Pro Gly Gly Asn Gly Gly Arg Pro Ser
    290                 295                 300
```

-continued

```
Asp Thr Tyr Gly Ala Pro Gly Gly Asn Gly Gly Arg Pro Ser Asp
305                 310                 315                 320

Thr Tyr Gly Ala Pro Gly Gly Gly Asn Asn Gly Gly Arg Pro
        325                 330                 335

Ser Ser Tyr Gly Ala Pro Gly Gln Gly Gln Gly Asn Gly Asn Gly
            340                 345                 350

Gly Arg Ser Ser Ser Tyr Gly Ala Pro Gly Gly Asn Gly Gly
        355                 360                 365

Arg Pro Ser Asp Thr Tyr Gly Ala Pro Gly Gly Asn Gly Gly Arg
    370                 375                 380

Pro Ser Asp Thr Tyr Gly Ala Pro Gly Gly Asn Asn Gly Gly Arg
385                 390                 395                 400

Pro Ser Ser Ser Tyr Gly Ala Pro Gly Gly Asn Gly Gly Arg Pro
        405                 410                 415

Ser Asp Thr Tyr Gly Ala Pro Gly Gly Asn Gly Asn Gly Ser Gly
            420                 425                 430

Gly Arg Pro Ser Ser Ser Tyr Gly Ala Pro Gly Gln Gly Gln Gly
        435                 440                 445

Phe Gly Gly Arg Pro Ser Asp Ser Tyr Gly Ala Pro Gly Gln Asn Gln
450                 455                 460

Lys Pro Ser Asp Ser Tyr Gly Ala Pro Gly Ser Gly Asn Gly Asn Gly
465                 470                 475                 480

Gly Arg Pro Ser Ser Ser Tyr Gly Ala Pro Gly Ser Gly Pro Gly Gly
            485                 490                 495

Arg Pro Ser Asp Ser Tyr Gly Pro Pro Ala Ser Gly Ser Gly Ala Gly
                500                 505                 510

Gly Ala Gly Gly Ser Gly Pro Gly Ala Asp Tyr Asp Asn Asp Glu
        515                 520                 525
```

<210> SEQ ID NO 58
<211> LENGTH: 519
<212> TYPE: PRT
<213> ORGANISM: Artificial sequence
<220> FEATURE:
<223> OTHER INFORMATION: 6H-resilin-CBD

<400> SEQUENCE: 58

```
Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
            85                  90                  95

Tyr Gly Ala Pro Gly Gly Asn Gly Asn Gly Arg Pro Ser Ser
        100                 105                 110

Ser Tyr Gly Ala Pro Gly Gly Asn Gly Gly Arg Pro Ser Asp Thr
            115                 120                 125

Tyr Gly Ala Pro Gly Gly Asn Gly Gly Arg Pro Ser Asp Thr Tyr
        130                 135                 140
```

```
Gly Ala Pro Gly Gly Gly Asn Gly Asn Gly Gly Arg Pro Ser Ser
145                 150                 155                 160

Ser Tyr Gly Ala Pro Gly Gln Gly Gln Asn Gly Asn Gly Gly Arg
            165                 170                 175

Ser Ser Ser Ser Tyr Gly Ala Pro Gly Gly Asn Gly Gly Arg Pro
        180                 185                 190

Ser Asp Thr Tyr Gly Ala Pro Gly Gly Asn Gly Gly Arg Pro Ser
        195                 200                 205

Asp Thr Tyr Gly Ala Pro Gly Gly Asn Asn Gly Gly Arg Pro Ser
        210                 215                 220

Ser Ser Tyr Gly Ala Pro Gly Gly Asn Gly Gly Arg Pro Ser Asp
225                 230                 235                 240

Thr Tyr Gly Ala Pro Gly Gly Asn Gly Asn Gly Ser Gly Gly Arg
            245                 250                 255

Pro Ser Ser Ser Tyr Gly Ala Pro Gly Gln Gly Gln Gly Phe Gly
        260                 265                 270

Gly Arg Pro Ser Asp Ser Tyr Gly Ala Pro Gly Gln Asn Gln Lys Pro
        275                 280                 285

Ser Asp Ser Tyr Gly Ala Pro Gly Ser Gly Asn Gly Asn Gly Arg
290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Ala
            325                 330                 335

Gly Gly Ser Gly Pro Gly Gly Ala Asp Tyr Asp Asn Asp Glu Gly Ile
        340                 345                 350

Pro Asp Pro Gly Met Ala Ala Thr Ser Ser Met Ser Val Glu Phe Tyr
        355                 360                 365

Asn Ser Asn Lys Ser Ala Gln Thr Asn Ser Ile Thr Pro Ile Ile Lys
370                 375                 380

Ile Thr Asn Thr Ser Asp Ser Asp Leu Asn Leu Asn Asp Val Lys Val
385                 390                 395                 400

Arg Tyr Tyr Tyr Thr Ser Asp Gly Thr Gln Gly Gln Thr Phe Trp Cys
            405                 410                 415

Asp His Ala Gly Ala Leu Leu Gly Asn Ser Tyr Val Asp Asn Thr Ser
            420                 425                 430

Lys Val Thr Ala Asn Phe Val Lys Glu Thr Ala Ser Pro Thr Ser Thr
            435                 440                 445

Tyr Asp Thr Tyr Val Glu Phe Gly Phe Ala Ser Gly Arg Ala Thr Leu
            450                 455                 460

Lys Lys Gly Gln Phe Ile Thr Ile Gln Gly Arg Ile Thr Lys Ser Asp
465                 470                 475                 480

Trp Ser Asn Tyr Thr Gln Thr Asn Asp Tyr Ser Phe Asp Ala Ser Ser
            485                 490                 495

Ser Thr Pro Val Val Asn Pro Lys Val Thr Gly Tyr Ile Gly Gly Ala
            500                 505                 510

Lys Val Leu Gly Thr Ala Pro
        515
```

<210> SEQ ID NO 59
<211> LENGTH: 1520
<212> TYPE: DNA
<213> ORGANISM: Artificial sequence
<220> FEATURE:
<223> OTHER INFORMATION: 6H-Res-ChBD expressing sequence -continued

<400> SEQUENCE: 59

| | | | | | |
|---|---|---|---|---|---|
| gaaattaata | cgactcacta | tagggggaatt | gtgagcggat | aacaattccc | ctctagaaat | 60 |
| aattttgttt | aactttaaga | aggagatata | catatgtcgt | actaccatca | ccatcaccat | 120 |
| cacgattacg | atatcccaac | gaccgaaaac | ctgtattttc | agggcgccat | gggaccggag | 180 |
| ccaccagtta | actcgtatct | acctccgtcc | gatagctatg | gagcaccggg | tcagagtggt | 240 |
| cccggcggca | ggccgtcgga | ttcctatgga | gctcctggtg | gtggaaacgg | tggacggccc | 300 |
| tcagacagct | atggcgctcc | aggccagggt | caaggacagg | gacaaggaca | aggtggatat | 360 |
| gcaggcaagc | cctcagatac | ctatggagct | cctggtggtg | gaaatggcaa | cggaggtcgt | 420 |
| ccatcgagca | gctatggcgc | tcctggcggt | ggaaacggtg | gtcgtccttc | ggatacctac | 480 |
| ggtgctcctg | gtgcggaaaa | tggtggacgc | ccatcggaca | cttatggtgc | tcctggtggt | 540 |
| ggtggaaatg | gcaacggcgg | acgaccttca | agcagctatg | gagctcctgg | tcaaggacaa | 600 |
| ggcaacggaa | atggcggtcg | ctcatcgagc | agctatggtg | ctcctggcgg | tggaaacggc | 660 |
| ggtcgtcctt | cggataccta | cggtgctccc | ggtggtggaa | acggtggtcg | tccttcggat | 720 |
| acttacggcg | ctcctggtgg | cggcaataat | ggcggtcgtc | cctcaagcag | ctacggcgct | 780 |
| cctggtggtg | gaaacggtgg | tcgtccatct | gacacctatg | gcgctcctgg | tggcggtaac | 840 |
| ggaaacggca | gcggtggtcg | tccttcaagc | agctatggag | ctcctggtca | gggccaaggt | 900 |
| ggatttggtg | gtcgtccatc | ggactcctat | ggtgctcctg | gtcagaacca | aaaaccatca | 960 |
| gattcatatg | gcgcccctgg | tagcggcaat | ggcaacggcg | gacgtccttc | gagcagctat | 1020 |
| ggagctccag | gctcaggacc | tggtggccga | ccctccgact | cctacggacc | cccagcttct | 1080 |
| ggatcgggag | caggtggcgc | tggaggcagt | ggacccggcg | gcgctgacta | cgataacgat | 1140 |
| gagcccgcca | agtacgaatt | taattaccag | gttgaggacg | cgcccagcgg | actctcgttc | 1200 |
| gggcattcag | agatgcgcga | cggtgacttc | accaccggcc | agtacaatgt | cctgttgccc | 1260 |
| gacggaagga | agcaaattgt | ggagtatgaa | gccgaccagc | agggctaccg | gccacagatc | 1320 |
| cgctacgaag | gcgatgccaa | cgatggcagt | ggtcccagcg | gtccttaagg | atccggaatt | 1380 |
| caaaggccta | cgtcgacgag | ctcaactagt | gcggccgctt | tcgaatctag | agcctgcagt | 1440 |
| ctcgagcacc | accaccacca | ccactgagat | ccggctgcta | acaaagcccg | aaaggaagct | 1500 |
| gagttggctg | ctgccaccgc | | | | | 1520 |

<210> SEQ ID NO 60
<211> LENGTH: 1275
<212> TYPE: DNA
<213> ORGANISM: Artificial sequence
<220> FEATURE:
<223> OTHER INFORMATION: 6H-Resilin expressing sequence

<400> SEQUENCE: 60

| | | | | | |
|---|---|---|---|---|---|
| gaaattaata | cgactcacta | tagggggaatt | gtgagcggat | aacaattccc | ctctagaaat | 60 |
| aattttgttt | aactttaaga | aggagatata | catatgtcgt | actaccatca | ccatcaccat | 120 |
| cacgattacg | atatcccaac | gaccgaaaac | ctgtattttc | agggcgccat | gggaccggag | 180 |
| ccaccagtta | actcgtatct | acctccgtcc | gatagctatg | gagcaccggg | tcagagtggt | 240 |
| cccggcggca | ggccgtcgga | ttcctatgga | gctcctggtg | gtggaaacgg | tggacggccc | 300 |
| tcagacagct | atggcgctcc | aggccagggt | caaggacagg | gacaaggaca | aggtggatat | 360 |
| gcaggcaagc | cctcagatac | ctatggagct | cctggtggtg | gaaatggcaa | cggaggtcgt | 420 |
| ccatcgagca | gctatggcgc | tcctggcggt | ggaaacggtg | gtcgtccttc | ggatacctac | 480 |

| | |
|---|---|
| ggtgctcctg gtggcggaaa tggtggacgc ccatcggaca cttatggtgc tcctggtggt | 540 |
| ggtggaaatg gcaacggcgg acgaccttca agcagctatg gagctcctgg tcaaggacaa | 600 |
| ggcaacggaa atggcggtcg ctcatcgagc agctatggtg ctcctggcgg tggaaacggc | 660 |
| ggtcgtcctt cggatacccta cggtgctccc ggtggtggaa acggtggtcg tccttcggat | 720 |
| acttacggcg ctcctggtgg cggcaataat ggcggtcgtc cctcaagcag ctacggcgct | 780 |
| cctggtggtg gaaacggtgg tcgtccatct gacacctatg gcgctcctgg tggcggtaac | 840 |
| ggaaacggca gcggtggtcg tccttcaagc agctatggag ctcctggtca gggccaaggt | 900 |
| ggatttggtg gtcgtccatc ggactccatt ggtgctcctg gtcagaacca aaaaccatca | 960 |
| gattcatatg gcgcccctgg tagcggcaat ggcaacggcg gacgtccttc gagcagctat | 1020 |
| ggagctccag gctcaggacc tggtggccga ccctccgact cctacggacc cccagcttct | 1080 |
| ggatcgggag caggtggcgc tggaggcagt ggacccggcg gcgctgacta cgataacgat | 1140 |
| gagggatcca atcactagtg aattcgcggc cgctttcgaa tctagagcct gcagtctcga | 1200 |
| gcaccaccac caccaccact gagatccggc tgctaacaaa gcccgaaagg aagctgagtt | 1260 |
| ggctgctgcc accgc | 1275 |

<210> SEQ ID NO 61
<211> LENGTH: 1832
<212> TYPE: DNA
<213> ORGANISM: Artificial sequence
<220> FEATURE:
<223> OTHER INFORMATION: 6H-CBD-resilin expressing sequence

<400> SEQUENCE: 61

| | |
|---|---|
| gaaattaata cgactcacta tagggggaatt gtgagcggat aacaattccc ctctagaaat | 60 |
| aattttgttt aactttaaga aggagatata catatgtcgt actaccatca ccatcaccat | 120 |
| cacgattacg atatcccaac gaccgaaaac ctgtattttc agggcgccat ggcagcgaca | 180 |
| tcatcaatgt cagttgaatt ttacaactct aacaaagcag cacaaacaaa ctcaattaca | 240 |
| ccaataatca aaattactaa cacagctgac agtgattta atttaaatga cgtaaaagtt | 300 |
| agatattatt acacaagtga tggtacacaa ggacaaactt tctggggtga tcatgctggt | 360 |
| gcattattag gaaatagcta tgttgataac actggcaaag tgacagcaaa cttcgttaaa | 420 |
| gaaacagcaa gcccaacatc aacctatgat acatatgttg aatttggatt tgcaagcgga | 480 |
| gcagctactc ttaaaaaagg acaatttata actattcaag gaagaataac aaaatcagac | 540 |
| tggtcaaaact acgctcagac aaatgactat tcatttgatg caagtagttc aacaccagtt | 600 |
| gtaaatccaa aagttacagg atatataggt ggagctaaag tacttggtac agcaccaggt | 660 |
| ccagatgtac catcttcaat aattaatcct acttctgcaa catttgatcc ggagccacca | 720 |
| gttaactcgt atctacctcc gtccgatagc tatggagcac cgggtcagag tggtcccggc | 780 |
| ggcaggccgt cggattccta tggagctcct ggtggtggaa acggtggacg ccctcagac | 840 |
| agctatggcg ctccaggcca gggtcaagga cagggacaag acaaggtgg atatgcaggc | 900 |
| aagccctcag ataccctatgg agctcctggt ggtggaaatg gcaacggagg tcgtccatcg | 960 |
| agcagctatg gcgctcctgg cggtggaaac ggtggtcgtc cttcggatac ctacggtgct | 1020 |
| cctggtggcg gaaatggtgg acgcccatcg gacacttatg gtgctcctgg tggtggtgga | 1080 |
| aatggcaacg gcggacgacc ttcaagcagc tatggagctc ctggtcaagg acaaggcaac | 1140 |
| ggaaatggcg gtcgctcatc gagcagctat ggtgctcctg gcggtggaaa cggcggtcgt | 1200 |
| ccttcggata cctacggtgc tcccggtggt ggaaacggtg gtcgtccttc ggatacttac | 1260 |

```
ggcgctcctg gtggcggcaa taatggcggt cgtccctcaa gcagctacgg cgctcctggt    1320
ggtggaaacg gtggtcgtcc atctgacacc tatggcgctc ctggtggcgg taacggaaac    1380
ggcagcggtg gtcgtccttc aagcagctat ggagctcctg gtcagggcca aggtggattt    1440
ggtggtcgtc catcggactc ctatggtgct cctggtcaga accaaaaacc atcagattca    1500
tatggcgccc ctggtagcgg caatggcaac ggcggacgtc cttcgagcag ctatggagct    1560
ccaggctcag gacctggtgg ccgaccctcc gactcctacg accccccagc ttctggatcg    1620
ggagcaggtg gcgctggagg cagtggaccc ggcggcgctg actacgataa cgatgagtaa    1680
ggatccggaa ttcaaaggcc tacgtcgacg agctcaacta gtgcggccgc tttcgaatct    1740
agagcctgca gtctcgagca ccaccaccac caccactgag atccggctgc taacaaagcc    1800
cgaaaggaag ctgagttggc tgctgccacc gc                                   1832
```

<210> SEQ ID NO 62
<211> LENGTH: 1666
<212> TYPE: DNA
<213> ORGANISM: Artificial sequence
<220> FEATURE:
<223> OTHER INFORMATION: 6H-resilin-CBD expressing sequence

<400> SEQUENCE: 62

```
gaaattaata cgactcacta tagggggaatt gtgagcggat aacaattccc ctctagaaat      60
aattttgttt aactttaaga aggagatata catatgtcgt actaccatca ccatcaccat     120
cacgattacg atatcccaac gaccgaaaac ctgtattttc agggcgccat gggaccggag     180
ccaccagtta actcgtatct acctccgtcc gatagctatg agcaccgggt cagagtggt      240 cccggcggca ggccgtcgga ttcctatgga gctcctggtg gtggaaacgg tggacggccc     300
tcagacagct atggcgctcc aggccagggt caaggacagg acaaggaca aggtggatat      360 gcaggcaagc cctcagatac ctatggagct cctggtggtg aaatggcaa cggaggtcgt      420 ccatcgagca gctatggcgc tcctggcggt ggaaacggtg gtcgtccttc ggatacctac     480
ggtgctcctg gtggcggaaa tggtggacgc catcggaca cttatggtgc tcctggtggt     540
ggtggaaatg gcaacggcgg acgaccttca agcagctatg agctcctgg tcaaggacaa      600 ggcaacggaa atggcggtcg ctcatcgagc agctatggtg ctcctggcgg tggaaacggc     660
ggtcgtcctt cggatacccta cggtgctccc ggtggtggaa acggtggtcg tccttcggat     720
acttacggcg ctcctggtgg cggcaataat ggcggtcgtc cctcaagcag ctacggcgct     780
cctggtggtg aaacggtgg tcgtccatct gacacctatg cgctcctgg tggcggtaac     840 ggaaacggca gcggtggtcg tccttcaagc agctatggag ctcctggtca gggccaaggt     900
ggatttggtg gtcgtccatc ggactcctat ggtgctcctg gtcagaacca aaaaccatca     960
gattcatatg gcgccctgg tagcggcaat ggcaacggcg gacgtccttc gagcagctat    1020
ggagctccag gctcaggacc tggtggccga ccctccgact cctacggacc cccagcttct    1080
ggatcgggag caggtggcgc tggaggcagt ggacccggcg gcgctgacta cgataacgat    1140
gaggggatcc ccgaccccgg catggcagcg acatcatcaa tgtcagttga attttacaac    1200
tctaacaaat cagcacaaac aaactcaatt acaccaataa tcaaaattac taacacatct    1260
gacagtgatt taaatttaaa tgacgtaaaa gttagatatt attacacaag tgatggtaca    1320
caaggacaaa cttttctggtg tgaccatgct ggtgcattat taggaaatag ctatgttgat    1380
aacactagca agtgacagc aaacttcgtt aaagaaacag caagcccaac atcaacctat    1440
gatacatatg ttgaatttgg atttgcaagc ggacgagcta ctcttaaaaa aggacaattt    1500
```

```
ataactattc aaggaagaat aacaaaatca gactggtcaa actacactca aacaaatgac    1560
tattcatttg atgcaagtag ttcaacacca gttgtaaatc caaaagttac aggatatata    1620
ggtggagcta aagtacttgg tacagcacca taggatcgat ccagat                   1666
```